(12) United States Patent
Lu et al.

(10) Patent No.: US 7,402,586 B2
(45) Date of Patent: Jul. 22, 2008

(54) HETEROARYL AMINOGUANIDINES AND ALKOXYGUANIDINES AND THEIR USE AS PROTEASE INHIBITORS

(75) Inventors: Tianbao Lu, Collegeville, PA (US); Bruce Tomczuk, Collegeville, PA (US); Thomas P. Markotan, Morgantown, PA (US); Colleen Siedem, Kennett Square, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 11/254,086

(22) Filed: Oct. 19, 2005

(65) Prior Publication Data

US 2006/0211719 A1 Sep. 21, 2006

Related U.S. Application Data

(62) Division of application No. 10/714,988, filed on Nov. 17, 2003, now Pat. No. 7,029,654, which is a division of application No. 10/400,073, filed on Mar. 27, 2003, now Pat. No. 6,706,021, which is a division of application No. 10/241,513, filed on Sep. 12, 2002, now Pat. No. 6,566,379, which is a division of application No. 10/012,445, filed on Dec. 12, 2001, now Pat. No. 6,472,399, which is a division of application No. 09/827,292, filed on Apr. 6, 2001, now Pat. No. 6,350,764, which is a division of application No. 09/482,540, filed on Jan. 14, 2000, now Pat. No. 6,245,763, which is a division of application No. 09/199,167, filed on Nov. 25, 1998, now Pat. No. 6,037,356.

(60) Provisional application No. 60/079,107, filed on Mar. 23, 1998, provisional application No. 60/067,324, filed on Dec. 5, 1997, provisional application No. 60/066,475, filed on Nov. 26, 1997.

(51) Int. Cl.
C07D 239/54 (2006.01)
A61K 31/513 (2006.01)

(52) U.S. Cl. .................. 514/269; 544/309; 544/319

(58) Field of Classification Search ............ 544/309, 544/319; 514/269
See application file for complete search history.

(56) References Cited

U.S. PATENT DOCUMENTS

| | | | |
|---|---|---|---|
| 4,097,472 A | 6/1978 | Okamoto et al. | 424/177 |
| 4,418,052 A | 11/1983 | Wong | 424/1.1 |
| 4,980,148 A | 12/1990 | Dean | 424/9 |
| 5,011,686 A | 4/1991 | Pang | 424/94.1 |
| 5,024,829 A | 6/1991 | Berger et al. | 424/1.1 |
| 5,466,811 A | 11/1995 | Alexander | 546/283 |
| 5,656,600 A | 8/1997 | ABelman et al. | 514/13 |
| 5,656,645 A | 8/1997 | Tamura et al. | 514/349 |
| 5,658,885 A | 8/1997 | Lee et al. | 514/19 |
| 5,658,930 A | 8/1997 | Tamura et al. | 514/318 |
| 5,891,909 A | 4/1999 | Soll et al. | 514/517 |
| 6,037,356 A | 3/2000 | Lu et al. | 514/349 |
| 6,204,263 B1 | 3/2001 | Lu et al. | 514/235.8 |
| 6,235,778 B1 | 5/2001 | Tomczuk et al. | 514/517 |
| 6,245,763 B1 | 6/2001 | Lu et al. | 514/247 |
| 6,326,492 B1 | 12/2001 | Wang et al. | 544/63 |
| 6,350,764 B2 | 2/2002 | Lu et al. | 514/349 |

(Continued)

FOREIGN PATENT DOCUMENTS

EP 0 363 284 A2 4/1990

(Continued)

OTHER PUBLICATIONS

Majerus et al., Anticoagulant, Thrombolytic, And Antiplatelet Drugs, Goodman & Gilman's The Pharmacological Basis of Therapeutics, Ninth Edition, Chapter 54, pp. 1341-1359, 1996.*

(Continued)

*Primary Examiner*—Deepak Rao
(74) *Attorney, Agent, or Firm*—Woodcock Washburn LLP

(57) ABSTRACT

Aminoguanidine and alkoxyguanidine compounds are described, including compounds of the Formula VII:

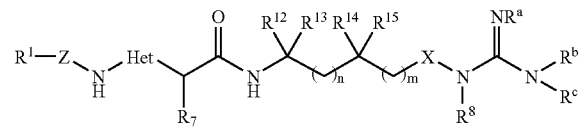

wherein X is O or $NR^9$ and Het, $R^1$, $R^7$, $R^8$, $R^{12}$—$R^{15}$, $R^a$, $R^b$, $R^c$, Z, and n are set forth in the specification, as well as hydrates, solvates or pharmaceutically acceptable salts thereof, that inhibit proteolytic enzymes such as thrombin. Also described are methods for preparing such compounds. The compounds of the invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin. The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents. Additionally, the compounds can be detectably labeled and employed for in vivo imaging of thrombi.

64 Claims, No Drawings

U.S. PATENT DOCUMENTS

| | | | | |
|---|---|---|---|---|
| 6,472,399 | B2 | 10/2002 | Lu et al. | 514/255.05 |
| 6,566,379 | B1 | 5/2003 | Lu et al. | 514/345 |
| 6,706,021 | B2 | 3/2004 | Lu et al. | 604/244 |

FOREIGN PATENT DOCUMENTS

| | | |
|---|---|---|
| SU | 174261 | 2/1966 |
| SU | 328634 | 12/1978 |
| SU | 938739 | 10/1982 |
| WO | WO 95/07291 | 3/1995 |
| WO | WO 96/18644 | 6/1996 |
| WO | WO 97/01338 | 1/1997 |
| WO | WO 97/30708 | 8/1997 |
| WO | WO 98/23565 | 6/1998 |
| WO | WO 01/04117 | 1/2001 |

OTHER PUBLICATIONS

Handin, Bleeding and Thrombosis, Harrisons's Principles of Internal Medicine, Twelfth Edition, pp. 348-353, 1991.*

Rauch et al., Thrombus Formation on Atherosclerotic Plaques: Pathogenesis and Clinical Consequences, Annals of Internal Medicine, vol. 134, No. 3, pp. 224-233, 2001.*

Van Aken et al., Anticoagulation: The Present and Future, Clin. Appl. Thrombosis/Hemostasis, vol. 7, No. 3, pp. 195-204, 2001.*

Hart et al., Atrial Fibrillation and Thromboembolism: A decade of progress in stroke prevention, Ann. Intern. Med. 131:688-695, 1999.*

Peterson et al., Expanding the Scope of Crystal Form Evaluation in Pharmaceutical Science, J Pharm Pharmaceut Sci, 9(3), pp. 317-326, 2006.*

Barrett, A.J., "Proteinase Inhibitors: Potential Drugs?", *Enzyme Inhibitors as Drugs*, 1980, Sandler, M., ed., The Macmillan Press Ltd., London, England, 219-229.

Brown, F.J. et al., "Design of Orally Active, Non Peptidic Inhibitors of Human Leukocyte Elastase", *J. Med. Chem.*, 1994, American Chemical Society, 37, 1259-1261.

Claeson, G., "Synthetic Peptides and Peptidomimetics as Substrates and Inhibitors of Thrombin and Other Proteases in the Blood Coagulation System", *Blood Coagulation and Fibrinolysis*, 1994, 5, 411-436, Rapid Communications.

Coughlin, S.R., "Molecular Mechanisms of Thrombin Signaling", *Seminars in Hematology*, 1994, 31, 270-277, W.B. Saunders Company.

Cuypers, H.T. et al., "Sufhydryl Content of Bovine Eye Lens Leucine Aminopeptidase. Determination of the Reactivity of the Sulfhydryl Groups of the Zinc Metalloenzyme, of the Enzyme Activated by Mg2, Mn2+, and Co2+, and of the Metal-Free Apoenzyme", *J. Biol. Chem.*, 1982, 257, 7086-7091, American Society of Biological Chemists, Inc.

De Roos, A. et al., "Myocardial Infarct Sizing and Assessment of Reperfusion by Magnetic Resonance Imaging: A Review", *Int. J. Cardiac Imaging*, 1991, 7, 133-138.

Edwards, P.D. et al., "Design, Synthesis, and Kinetic Evaluation of a Unique Class of Elastase Inhibitors, the Peptidyl, α-Ketobenzoxazoles, and the X-ray Crystal Structure of the Covalent Complex between Porcine Pancreatic Elastase and Ac-Ala-Pro-Val-2-Benzoxazole", *J. Am. Chem. Soc.*, 1992, 114, 1854-1863, American Chemical Society.

Harker, L.A., "Strategies for Inhibiting the Effects of Thrombin", *Blood Coagulation and Fibrinolysis*, 1994, 5, S47-S58.

Jeong, J.H. et al., "Cyclic Guanidino-Sugars with Low pKa as Transition-State Analog Inhibitors of Glycosidases: Neutral Instead of Charged Species are the Active Forms", *J. Am. Chem. Soc.*, 1996, 118, 4427-4234, American Chemical Society.

Kim, K.S. et al., "Preparation of Argatroban Analog Thrombin Inhibitors with Reduced Basic Guanidine Moiety, and Studies of their Cell Permeability and Antithrombotic Activities", *Med. Chem Res.*, 1996, 6, 377-383.

Lefkovits, J. et al., "Direct hrombin Inhibitors in Cardiovascular Medicine", *Circulation*, 1994, 90, 1522-1536, American Heart Association, Inc.

Mack, H. et al., "Design, Synthesis and Biological Activity of Novel Rigid Amidino-Phenylalanine Derivatives as Inhibitors of Thrombin", *J. Enzyme Inhibition*, 1995, 9, 73-86, Harwood Academic Publishers GmbH.

Powers, W.J. et al., "Indium-111 Plateley Scintigraphy in Cerebrovascular Disease", *Neurology*, 1982, 32, 938-943, American Academy of Neurology.

Saulnier, M.G., et al., "An Efficient Method for the Synthesis of Guanidino Prodrugs", *Bioorg. Med. Chem. Lett.*, 1994, 4, 1985-1990.

Thakur, M.L. et al., "Indium-111 Labeled Platelets: Studies on Preparation and Evaluation of In Vitro and In Vivo Functions", *Thrombosis Res.*, 1976, 9, 345-357, Pergamon Press, Inc.

CAPLUS 127:234621, abstract of Lee, S.-1. et al., "Amidino and Guanidino Substituted Boronic Acid Inhibitors of Trypsin-Like Enzymes", 1997, Accession No. 594514.

Eurasian Search Report for Application No. 200000578/28, for application filed Jun. 26, 2000.

WPINDEX, Accession No. 1993-218199, Derwent WPI English language abstract for SU 174261.

WPINDEX, Accession No. 1978-L1249A, Derwent WPI English language abstract for SU328634.

Caplus abstract Semple Edward et al, *Journal of Medicinal Chemistry*, 1996.

* cited by examiner

HETEROARYL AMINOGUANIDINES AND ALKOXYGUANIDINES AND THEIR USE AS PROTEASE INHIBITORS

This application is a divisional of U.S. application Ser. No. 10/714,988, filed on Nov. 17, 2003, now U.S. Pat. No. 7,029,654, which is a divisional of U.S. application Ser. No. 10/400,073, filed on Mar. 27, 2003, issued as U.S. Pat. No. 6,706,021, which is a divisional of U.S. application Ser. No. 10/241,513 filed on Sep. 12, 2002, issued as U.S. Pat. No. 6,566,379, which is a divisional of U.S. application Ser. No. 10/012,445 filed on Dec. 12, 2001, issued as U.S. Pat. No. 6,472,399, which is a divisional of U.S. application Ser. No. 09/827,292, filed on Apr. 6, 2001, issued as U.S. Pat. No. 6,350,764, which is a divisional of U.S. application Ser. No. 09/482,540 filed on Jan. 14, 2000, issued as U.S. Pat. No. 6,245,763, which is a divisional of U.S. application Ser. No. 09/199,167 filed on Nov. 25, 1998, issued as U.S. Pat. No. 6,037,356, which claims benefit under 35 U.S.C. § 119(e) of U.S. Provisional Application No. 60/079,107, filed Mar. 23, 1998, application Ser. No. 60/067,324, filed Dec. 5, 1997, and application Ser. No. 60/066,475, filed Nov. 26, 1997. The entirety of each of these applications is incorporated by reference herein.

BACKGROUND OF THE INVENTION

1. Field of the Invention

The present invention relates to novel compounds that function as proteolytic enzyme inhibitors, and particularly to a new class of thrombin inhibitors.

2. Related Art

Proteases are enzymes that cleave proteins at single, specific peptide bonds. Proteases can be classified into four generic classes: serine, thiol or cysteinyl, acid or aspartyl, and metalloproteases (Cuypers et al, *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomemlar nephritis. (Barret, in *Enzyme Inhibitors as Drugs*, Sandier, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons. Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4): 270-277 (1994)), and autoamplifies its own production through a feedback mechanism. Thus, inhibitors of thrombin function have therapeutic potential in a host of cardiovascular and non-cardiovascular diseases.

Factor Xa is another serine protease in the coagulation pathway. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5:411-436 (1994); Harker, *Blood Coagulation and Fibrinolysis* 5 (Suppl 1):S47-S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522-1536 (1994); Harker, *Blood Coagulation and Fibrinolysis* 5 (Suppi 1):S47-S58 (1994)).

In vivo diagnostic imaging methods for intravascular thrombi have been previously reported. These imaging methods use compounds that are detectably labeled with radioactive or paramagnetic atoms. For example, platelets labeled with the gamma emitter, In-111, can be employed as an imaging agent for detecting thrombi (Thakur, M. L. et al., *Thromb Res.* 9:345 (1976); Powers et al., *Neurology* 32:938 (1982)). The thrombolytic enzyme streptokinase labeled with Tc-99m has been proposed as an imaging agent (Wong, U.S. Pat. No. 4,418,052 (1983)). The fibrin-binding domains of *Staphylococcus aureus* derived protein A labeled with the gamma emitters, I-125 and I-131, have been proposed as imaging agents (Pang, U.S. Pat. No. 5,011,686 (1991)). Monoclonal antibodies having specificity for fibrin (in contrast to fibrinogen) and labeled with Tc-99m have been proposed as imaging agents (Berger et al., U.S. Pat. No. 5,024,829 (1991); Dean et al., U.S. Pat. No. 4,980,148 (1990)). The use of the paramagnetic-contrasting agent, gadolinium diethylenetriaminepentaacetic acid in magnetic resonance imaging of patients treated by thrombolysis for acute myocardial infarction has been reported (De Roos, A. et al, *Int. J. Card. Imaging* 7:133 (1991)). Radiolabeled and paramagnetically labeled alpha-ketoamide derivatives have also been proposed as thrombus imaging agents (Abelman et al., U.S. Pat. No. 5,656,600).

Edwards et al., *J. Amer. Chem. Soc.* 114:1854-63(1992), describes peptidyl α-ketobenzoxazoles that reversibly inhibit the serine proteases human leukocyte elastase and porcine pancreatic elastase.

European Published Application 363 284 describes analogs of peptidase substrates in which the nitrogen atom of the scissile amide group of the substrate peptide has been replaced by hydrogen or a substituted carbonyl moiety.

Australian Published Application 86245677 also describes peptidase inhibitors having an activated electrophilic ketone moiety such as fluoromethylene ketone or α-keto carboxyl derivatives.

Brown et al., *J. Med. Chem.* 37:1259-1261 (1994) describes orally active, non-peptidic inhibitors of human leukocyte elastase which contain trifluoromethylketone and pyridinone moieties.

H. Mack et al., *J. Enzyme Inhibition*, 9:73-86 (1995) describes rigid amidino-phenylalanine thrombin inhibitors which contain a pyridinone moiety as a central core structure.

PCT International Published Application WO 97/01338 describes pyridinone compounds having the formula:

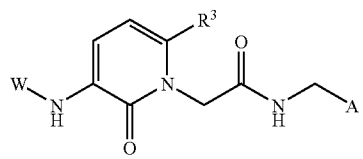

I where W is $R^1$, $R^1OCO$, $R^1CO$, $R^1SO_2$, or $(R^1)_m(CH_2)_n NH_qCO$;

$R^1$ is $R^2(CH_2)_n$, $(R^2)(OR^2)CH(CH_2)_p$, $(R^2)_2CH(CH_2)_n$, and $R^2O(CH_2)_p$;

$R^2$ is hydrogen, optionally substituted phenyl, naphthyl, biphenyl, a mono- or bicyclic heterocyclic ring, $COOR^6$, $C_{1-4}$ linear or branched alkyl, $C_{3-7}$ cycloalkyl, or $C_{7-12}$ bicyclic alkyl;

$R^3$ is hydrogen, $C_{1-4}$ linear or branched alkyl, $C_{3-7}$ cycloalkyl, or trifluoromethyl;

A is one of:

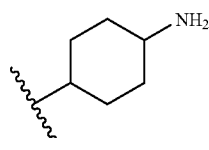

trans

II

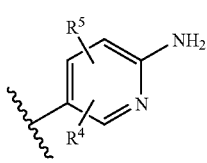

III

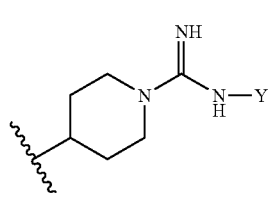

IV where Y is hydrogen, hydroxy, or CN; and
$R^6$ is hydrogen, or $C_{1-4}$ linear or branched alkyl.

PCT International Published Application WO97/30708 discloses pyridinone compounds of the general formula:

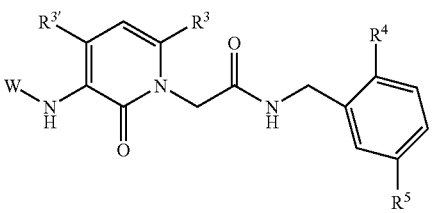

V

The compounds are disclosed to be useful for inhibiting thrombin and associated thrombotic occlusions.

PCT Published Application WO 96/18644 describes compounds having the formula:

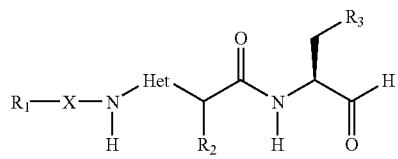

VI wherein
Het is selected from the group consisting of

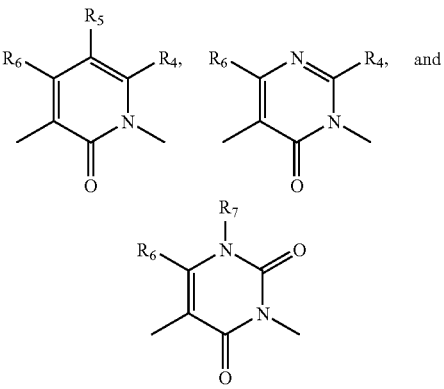

and $R_3$ is selected from the group consisting of:

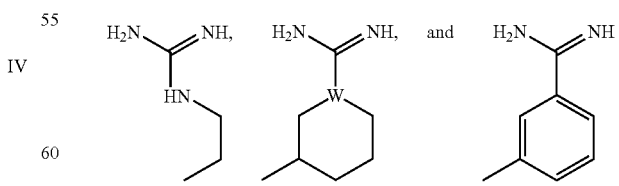

The compounds are described as specific inhibitors of thrombin.

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

SUMMARY OF THE INVENTION

The present invention is directed to novel aminoguanidine and alkoxyguanidine compounds having Formula VII (below). Also provided are processes for preparing compounds of Formula VII. The novel compounds of the present invention are potent inhibitors of proteases, especially trypsin-like serine proteases, such as chymotrypsin, trypsin, thrombin, plasmin and factor Xa Certain of the compounds exhibit antithrombotic activity via direct, selective inhibition of thrombin, or are intermediates useful for forming compounds having antithrombotic activity. Also provided are methods of inhibiting or treating aberrant proteolysis in a mammal and methods of treating thrombosis, ischemia, stroke, restenosis or inflammation in a mammal by administering an effective amount of a compound of Formula VII.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

Also provided are methods of inhibiting or treating aberrant proteolysis in a mammal, and methods for treating myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention provides diagnostic compositions which are useful for in vivo imaging of thrombi in a mammal, comprising a pharmaceutically acceptable carrier and a diagnostically effective amount of a compound or composition of the present invention.

In another aspect, the present invention includes methods which are useful for in vivo imaging or thrombi in a mammal.

DETAILED DESCRIPTION OF THE PREFERRED EMBODIMENTS

Compounds of the present invention include compounds of Formula VII:

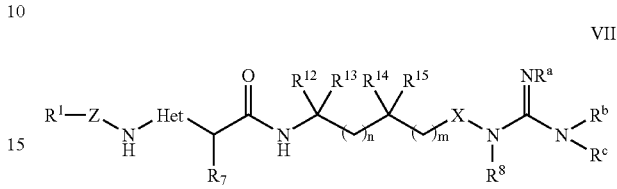

VII or a solvate, hydrate or pharmaceutically acceptable salt thereof; wherein:

$R^1$ is alkyl, cycloalkyl, cycloalkylalkyl, alkenyl, alkynyl, aryl, aralkyl, heterocycle or heterocycloalkyl, any of which may be optionally substituted;

Z is —$SO_2$—, —OCO—, —CO—, —$NR^2CO$— or a covalent bond,
where $R^2$ is hydrogen, alkyl, aralkyl, aryl, hydroxy($C_{2-10}$)alkyl, amino($C_{2-10}$)alkyl, monoalkylamino($C_{2-10}$)alkyl, dialkylamino($C_{2-10}$)alkyl or carboxyalkyl;

Het is selected from the group consisting of

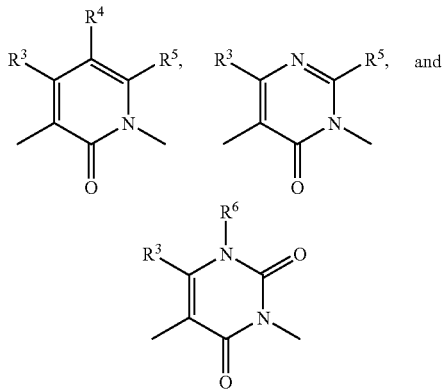

where
$R^3$, $R^4$ and $R^5$ are independently hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, —$CO_2R^x$, —$CH_2OR^x$ or —$OR^x$,
where $R^x$, in each instance, is independently one of hydrogen, alkyl or cycloalkyl wherein said alkyl or cycloalkyl groups may optionally have one or more unsaturations;

$R^6$ is hydrogen, alkyl, aralkyl, aryl, cyano($C_{2-10}$)alkyl, hydroxy($C_{2-10}$)alkyl, alkoxy($C_{2-10}$)alkyl, mono- and di-alkylamino($C_{2-10}$)alkyl, or carboxyalkyl;

$R^7$ is hydrogen, $C_{1-4}$alkyl, or $C_{2-4}$ alkenyl;

$R^8$ is hydrogen, alkyl, alkenyl, aralkyl, aryl, hydroxyalkyl, aminoalkyl, monoalkylamino ($C_{2-10}$)alkyl, dialkylamino ($C_{2-10}$)alkyl or carboxyalkyl;

$R^{12}$, $R^{13}$, $R^{14}$ and $R^{15}$ are independently hydrogen, alkyl, aralkyl, aryl, hydroxyalkyl, aminoalkyl, monoalkylaminoalkyl, dialkyl aminoalkyl or carboxyalkyl;

or $R^{12}$ and $R^{13}$ are taken together to form —$(CH_2)_y$—, where y is 2 to 7, preferably 2 to 5, while $R^{14}$ and $R^{15}$ are defined as above;

or $R^{14}$ and $R^{15}$ are taken together to form —$(CH_2)_q$—, where q is 2 to 7, preferably 2 to 5, while $R^{12}$ and $R^{13}$ are defined as above;

or $R^{12}$ and $R^{14}$ are taken together to form —$(CH_2)_r$—, where r is 0 (a bond) or 1 to 7, preferably 0-4, while $R^{13}$ and $R^{15}$ are defined as above;

X is oxygen or $NR^9$,
where $R^9$ is hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl;

$R^a$, $R^b$ and $R^c$ are independently hydrogen, alkyl, hydroxy, alkoxy, aryloxy, aralkoxy, alkoxycarbonyloxy, cyano or —$CO_2R^w$, where
$R^w$ is alkyl, cycloalkyl, phenyl, benzyl,

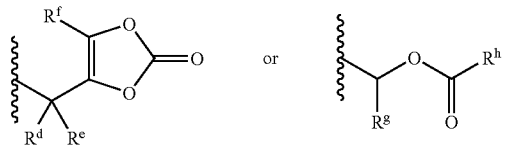

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n is from zero to 8; and m is from zero to 6.

A preferred group of compounds falling within the scope of the present invention include compounds of Formula VII wherein $R^1$ is one of $C_{6-10}$ ar($C_{1-4}$) alkyl, $C_{6-10}$ aryl, $C_{4-7}$ cycloalkyl($C_{1-4}$)alkyl, heterocycle or heterocyclo($C_{1-4}$)alkyl wherein the heterocycle is a 5- to 7-membered mono- or 9- to 10-membered bi-cyclic heterocyclic ring that can be saturated or unsaturated, which contains 1 to 3 heteroatoms selected from N, O and S. Any of these $R^1$ groups can be optionally substituted by 1-5, preferably by one, two or three of hydroxy, nitro, trifluoromethyl, halogen, $C_{1-6}$ alkyl, $C_{2-6}$ alkenyl, $C_{6-10}$ aryl, $C_{1-6}$ alkoxy, $C_{6-10}$ ar($C_{1-6}$)alkoxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, ($C_{1-6}$)alkoxy($C_{2-6}$)alkoxy, mono- and di-$C_{1-4}$ alkylamino ($C_{2-6}$) alkoxy, $C_{2-10}$ mono(carboxyalkyl)amino, bis($C_{2-10}$ carboxyalkyl) amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{6-10}$ arylsulfonyl, $C_{6-10}$ ar($C_1$) alkylsulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, or perfluoroethoxy.

An especially preferred group of compounds include compounds of Formula VII wherein $R^1$ is phenyl, benzyl, naphthyl, naphthylmethyl, pyridyl, pyridylmethyl, thienyl, thienylmethyl, quinolinyl or quinolinylmethyl, any of which is optionally substituted by one, two or three optional substituents listed in the preceding paragraph, especially halo, such as chloro or fluoro, methoxy, methyl, trifluoromethyl, cyano, nitro, methylsulfonyl, amino or dimethylamino.

Useful values of $R^1$ include, for example, benzyl, fluorobenzyl, chlorobenzyl, iodobenzyl, dichlorobenzyl, bromobenzyl, trifluoromethylbenzyl, methylsulfonylbenzyl, di(trifluoromethyl)benzyl, methylbenzyl, t-butylbenzyl, methoxybenzyl, dimethoxybenzyl, hydroxybenzyl, carboxybenzyl, aminobenzyl, methylaminobenzyl, n-butylaminobenzyl, amidinobenzyl, guanidinobenzyl, formyliminoaminobenzyl, acetimidoylamrinobenzyl, methoxycarbonylbenzyl, ethoxycarbonylbenzyl, carboxymethoxybenzyl, naphthylmethyl, hydroxynaphthylmethyl, cyclohexylmethyl, cyclopentylmethyl, phenyl, chlorophenyl, iodophenyl, dichlorophenyl, bromophenyl, trifluoromethylphenyl, methylsulfonylphenyl, di(trifluoromethyl)phenyl, methylphenyl, t-butylphenyl, methoxyphenyl, dimethoxyphenyl, hydroxyphenyl, carboxyphenyl, aminophenyl, methylaminophenyl, n-butylaminophenyl, amidinophenyl, guanidinophenyl, formyliminoaminophenyl, acetimidoylaminophenyl, methoxycarbonylphenyl, ethoxycarbonylphenyl, carboxymethoxyphenyl, naphthyl, hydroxynaphthyl, cyclohexyl, and cyclopentyl. Additional useful values include pyridyl, thienyl, isoquinolinyl, pyridylmethyl, isoquinolinylmethyl, tetrahydroquinolinyl and tetrahydroquinolinylmethyl.

More preferred values of $R^1$ include phenyl, 2-chlorophenyl, 3-chlorophenyl, 4-chlorophenyl, 4-bromophenyl, 4-iodophenyl, 4-methoxyphenyl, 4-methylphenyl, 2-trifluoromethylphenyl, 4-trifluoromethylphenyl, 2-fluorophenyl, 3-fluorophenyl, 4-fluorophenyl, 3,4-dichlorophenyl, 3-chloro-4-fluorophenyl, 3,5-dichlorophenyl, 2-methylphenyl, 3-methylphenyl, 4-ethylphenyl, 2-methylsulfonylphenyl, 4-isopropylphenyl, 3,4-dimethoxyphenyl, 2,4,6-trimethylphenyl, 2,5-dimethylphenyl, 4-vinylphenyl, 2-chloro-6-methylphenyl, 3-bromo-6-methoxyphenyl, 3-chloro-2-methylphenyl, 2-chloro-5-trifluoromethylphenyl, 2,4-dichlorophenyl, 2-butoxy-5-(1,1-dimethylpropyl)phenyl, 3-nitrophenyl, 4-chloro-3-nitrophenyl, 4-methylcarbonylaminophenyl, 4-tert-butylphenyl, 3-cyanophenyl, 4-methylsulfonylphenyl, pentafluorophenyl, 2,5-dichlorophenyl, 2,4-dimethoxyphenyl, 2-methyl-5-nitrophenyl, 3-chloro-2-cyanophenoxy)phenyl, 2-chloro-4-fluorophenyl, 3-chloro-6-methoxyphenyl, 2-methoxy-5-methylphenyl, 4-phenylphenyl, 2-propylbutyl, 5-chloro-2-methoxyphenyl, 2-cyanophenyl, 2-(N-hydroxy)aminophenyl, 2-(4-biphenylmethoxy)phenyl, 2-(3-biphenylmethoxy)phenyl, benzyl, 2-(phenylsulfonyl)phenyl, 2,4-bis(methylsulfonyl)phenyl, 2-chloro-4-methylsulfonylphenyl, benzyl, 3-chlorobenzyl, 3-trifluoromethylbenzyl, 2-trifluoromethylbenzyl, 2-iodobenzyl, 2-chlorobenzyl, 2-bromobenzyl, 3-fluorobenzyl, 4-chlorobenzyl, 2-chloro-6-fluorobenzyl, 2-fluorobenzyl, 2,3-dichlorobenzyl, 3,4-difluorobenzyl, 2,4-dichlorobenzyl, 2,5-dichlorobenzyl, 3,4-dichlorobenzyl, 2-methylbenzyl, 5-chloro-2-methoxybenzyl, 2-cyanobenzyl, 2-(4-biphenylmethoxy)benzyl, 2-(3-biphenylmethoxy)benzyl, 2-(phenylsulfonyl)benzyl, 2,4-bis(methylsulfonyl)benzyl, 3-methylsulfonylbenzyl, 2-chloro-4-methylsulfonylbenzyl, 1-naphthalenylmethyl, 2-naphthalenylmethyl, and 2-naphthalenyl.

Additional preferred values of $R^1$ include dansyl, thien-2-yl, pyridin-2-yl, 3-methylquinolin-1-yl, 1-methylimidazol-4-yl, quinolin-5-yl, quinoline-8-yl, 6-bromonaphthalen-2-yl, 6-chloronaphthalen-2-yl, 5-chlorothien-2-yl, 5-methyl-8- quinolinyl, 8-quinolinylmethyl, 5-methyl-8-quinolinylmethyl, 4-benzo-2,1,3-thiadiazolyl, and 5-chloro-1,3-dimethyl-4-pyrazolyl.

Preferred values of $R^2$ in Formula VII include hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, $C_{2-7}$ carboxyalkyl, mono($C_{1-4}$ alkyl)amino($C_{1-8}$)alkyl, and di($C_{1-4}$ alkyl)amino($C_{1-8}$)alkyl. Suitable values of $R^2$ include hydrogen, methyl, ethyl, propyl, n-butyl, benzyl, phenylethyl, 2-hydroxyethyl, 3-hydroxypropyl, 4-hydroxybutyl, 2-aminoethyl, 2-carboxymethyl, 3-carboxyethyl, 4-carboxypropyl and 2-(dimethylamino)ethyl, with hydrogen being most preferred.

Preferred Het groups include

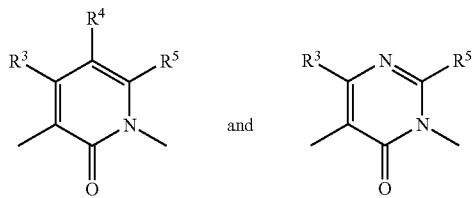

Preferred compounds are those where $R^3$, $R^4$ and $R^5$ are independently hydrogen, $C_{1-4}$ alkyl, $C_{3-7}$ cycloalkyl, $C_{6-14}$ aryl, especially $C_{6-10}$ aryl, $C_{6-10}$ ar($C_{1-4}$)alkyl, trifluoromethyl, halogen, hydroxyalkyl, cyano, nitro, carboxamido, carboxy, alkoxycarbonyl, carboxymethyl, alkoxycarbonylmethyl, or cycloalkyloxycarbonyl.

Useful values of $R^3$, $R^4$ and $R^5$ include hydrogen, methyl, ethyl, propyl, chloro, bromo, trifluoromethyl, hydroxymethyl, methoxy, ethoxy, carboxamido, nitro, phenyl, cyclopropyl, hydroxy, isopropyl, methoxycarbonyl, ethoxycarbonyl and benzyl.

Preferred $R^3$ and $R^4$ groups include hydrogen, $C_{1-12}$ alkyl, and $C_{2-6}$ alkenyl. A most preferred value of $R^3$ and $R^4$ is hydrogen.

Preferred $R^5$ groups include hydrogen, halogen, $C_{1-5}$ alkyl, $C_{3-6}$ alkenyl, $C_{3-5}$ cycloalkyl, trifluoromethyl, and $C_{1-4}$ alkoxy, more preferably $C_{1-4}$ alkyl, such as methyl, ethyl, propyl or isopropyl.

A particularly preferred Het, when $R^3$ and $R^4$ are independently selected to be hydrogen or or methyl, is

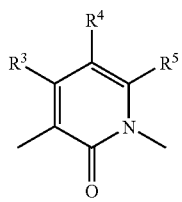

wherein $R^5$ is selected from the group consisting of hydrogen, methyl, ethyl, propenyl, allyl, propyl, isopropyl, butyl, R-sec-butyl, S-sec-butyl, isobutyl, 1-pentyl, R-2-pentyl, S-2-pentyl, 3-pentyl, S-1-(2-methyl)-butyl, R-2-(3-methyl)-butyl, 1-(3-methyl)-butyl, R-1-(2-methyl)-butyl, cyclopentyl, 2-pyrrolyl, 3-pyrrolyl, 1-hexyl, S-2-hexyl, R-2-hexyl, R-3-hexyl, and S-3-hexyl. A particularly preferred Het according to this aspect has hydrogen, methyl, ethyl, propyl or isopropyl as $R^5$.

Preferred values of Z include —$SO_2$— and a covalent bond.

A preferred $R^7$ group is hydrogen.

Preferred compounds are those of Formula VII, where $R^8$ is hydrogen, $C_{1-6}$ alkyl or $C_{6-10}$ aryl ($C_{1-6}$)alkyl.

Preferred compounds when X is $NR^9$ are those wherein $R^9$ is hydrogen or $C_{1-6}$ alkyl, optionally substituted by one, two or three, preferably one, of amino, monoalkylamino, dialkylamino, alkoxy, hydroxy, alkoxycarbonyl, aryloxycarbonyl, aralkoxycarbonyl, carboalkoxy, phenyl, cyano, trifluoromethyl, acetylamino, pyridyl, thiophenyl, furyl, pyrrolyl or imidazolyl.

Suitable values of $R^9$ include hydrogen, methyl, ethyl, propyl, n-butyl, benzyl, phenethyl, 2-hydroxyethyl, 3-hydroxypropyl, 4-hydroxybutyl, carboxymethyl and carboxyethyl.

Most preferred compounds are those where X is oxygen.

Preferred compounds are those of Formula VII, where $R^{12}$, $R^{13}$, $R^{14}$ and $R^{15}$ are independently one of hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl. Useful values of $R^{12}$, $R^{13}$, $R^{14}$ and $R^{15}$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl. Additional preferred compounds are those where $R^{12}$ and $R^{13}$ are taken together to form —$(CH)_y$— where y is 2.

Preferred values of $R^a$, $R^b$ and $R^c$ in Formula VII are independently hydrogen, hydroxy, $C_{1-6}$ alkyl, $C_{1-6}$ alkoxy, cyano or —$CO_2R^w$, where $R^w$, in each instance, is preferably one of $C_{1-4}$alkyl, $C_{4-7}$cycloalkyl or benzyloxycarbonyl. Suitable values of $R^a$, $R^b$ and $R^c$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$. In the most preferred embodiments, $R^a$, $R^b$ and $R^c$ are each hydrogen.

Also preferred at $R^a$, $R^b$ and $R^c$ is the group —$CO_2R^w$, where $R^w$ is one of

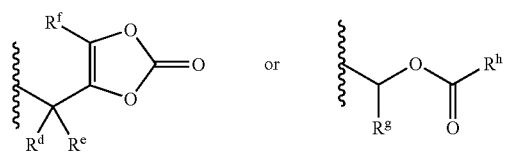

where $R^d$-$R^h$ are defined as above. When $R^a$, $R^b$ and $R^c$ are —CO, $R^w$, where $R^w$ is one of one of these moieties, the resulting compounds are prodrugs that possess desirable formulation and bioavailability characteristics. A preferred value for each of $R^d$, $R^e$ and $R^g$ is hydrogen, $R^f$ is methyl, and preferred values for $R^h$ include benzyl and tert-butyl.

Preferred values of n in Formula VII include from zero to 6 more preferably from zero to 4, and most preferably zero, 1 or 2.

Preferred values of m are from zero to 4, most preferably zero, 1 or 2.

In the most preferred compounds m and n are both zero.

According to a particularly preferred aspect, provided are compounds of Formula VII wherein Z is —SO$_2$—, R$^1$ is substituted or unsubstituted aryl or aralkyl, Het is

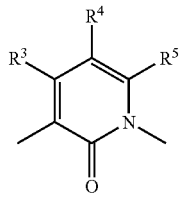

X is O, R$^8$ is hydrogen, C$_{1-6}$ alkyl or C$_{6-10}$ aryl (C$_{1-6}$)alkyl and R$^a$, R$^b$ and R$^c$ are all hydrogen. A very preferred aspect is directed to such compounds where R$^1$ is substituted or unsubstituted benzyl or phenyl, X is O, and R$^8$ is hydrogen, C$_{1-6}$ alkyl, or C$_{6-10}$ aryl (C$_{1-6}$)alkyl, and R$^a$, R$^b$ and R$^c$ are all hydrogen.

A preferred group of compounds has Formula VIII:

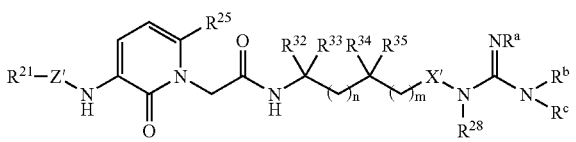

VIII or a solvate, hydrate of pharmaceutically acceptable salt thereof; wherein

Z' is —OCO—, —CO—, —SO$_2$—, —NHCO—, or a covalent bond;

R$^{21}$ is R$^{22}$(CH$_2$)$_k$, where k is 0-4, (R$^{22}$)(OR$^{22}$CH(CH$_2$)$_p$, where p is 1-4, (R$^{22}$)$_2$CH(CH$_2$)$_k$, where k is 0-4 and R$^{22}$ can be the same or different, and wherein (R$^{22}$)$_2$ can also be a ring substituent on CH represented by C$_{3-7}$ cycloalkyl, C$_{7-12}$ bicyclic alkyl, or a 5- to 7-membered mono-, or 9- to 10-membered bicyclic heterocyclic ring which can be saturated or unsaturated, and which contains from one to three heteroatoms selected from the group consisting of N, O and S, and R$^{22}$O(CH$_2$)$_p$, wherein p is 1-4;

R$^{22}$ is hydrogen; phenyl, unsubstituted or substituted with one or more of C$_{1-4}$ alkyl, C$_{1-4}$ alkoxy, halogen, trifluoromethyl, hydroxy, COOH, or CONH$_2$; naphthyl; biphenyl; a 5- to 7-membered mono- or a 9- to 10-membered bicyclic heterocyclic ring which can be saturated or

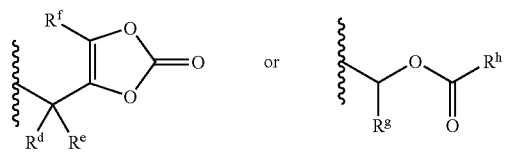

where R$^d$ and R$^e$ are independently hydrogen, C$_{1-6}$ alkyl, C$_{2-6}$ alkenyl or phenyl, R$^f$ is hydrogen, C$_{1-6}$ alkyl, C$_{2-6}$ alkenyl or phenyl, R$^g$ is hydrogen, C$_{1-6}$ alkyl, C$_{2-6}$ alkenyl or phenyl, and R$^h$ is aralkyl or C$_{1-6}$ alkyl;

R$^{32}$, R$^{33}$, R$^{34}$ and R$^{35}$ are independently one of hydrogen, C$_{1-6}$ alkyl, C$_{2-10}$ carboxyalkyl or C$_{2-10}$ hydroxyalkyl, or R$^{32}$ and R$^{33}$ are taken together to form —(CH$_2$)$_y$—, where y is 2 to 5, while R$^{34}$ and R$^{35}$ are defined as above; or R$^{34}$ and R$^{35}$ are taken together to form —(CH$_2$)$_q$—, where q is 2 to 5, while R$^{32}$ and R$^{33}$ are defined as above; or R$^{32}$ and R$^{34}$ are taken together to form —(CH$_2$)$_r$—, where r is 0 (a bond) or 1-4, while R$^{33}$ and R$^{35}$ are defined as above;

R$^{28}$ is hydrogen, C$_{1-4}$ alkyl or C$_{6-10}$ aryl(C$_{1-4}$)alkyl; X' is O;

n is from zero to 4; and m is zero to 2.

A useful class of compounds is the embodiment wherein Z' is a covalent bond or —SO$_2$—. A further useful subclass of compounds is the embodiment wherein R$^{21}$ is R$^{22}$(CH$_2$)$_k$, (R$^{22}$)$_2$CH(CH$_2$)$_k$, phenyl, or (phenyl)$_2$-CH.

Another useful class of compounds is the embodiment wherein R$^{25}$ is C$_{1-4}$ alkyl and particularly wherein R$^{25}$ is methyl, ethyl, propyl or isopropyl.

Another useful class of compounds it's the embodiment wherein R$^{28}$ is hydrogen or C$_{1-4}$ alkyl, and X' is O. Exemplary structures of compounds within the scope of the invention include the following:

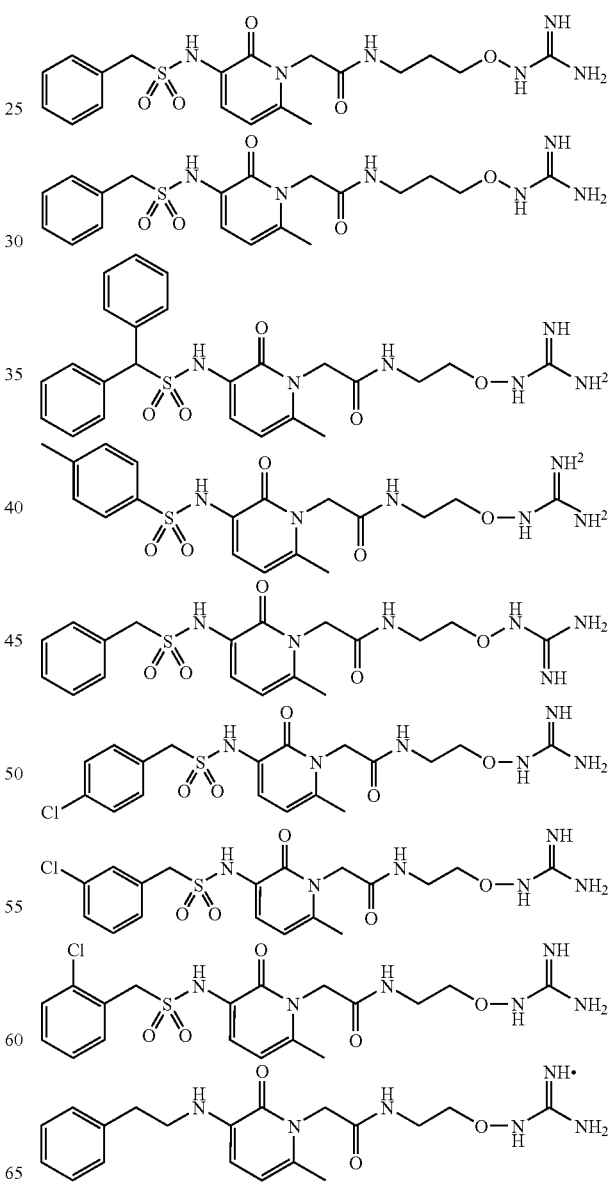

as well as pharmaceutically acceptable salts thereof, for example the hydrochloride and acetate salts thereof.

Examples of novel individual compounds falling within the scope of the present invention include:

3-Benzylsulfonylamino-6-methyl-1-[(3-guanidinooxypropyl)aminocarbonylmethyl]-2-pyridinone trifluoroacetate;

3-Benzylsulfonylamino-6-methyl-1-[(2-guanidinooxyethyl)aminocarbonyhnethyl]-2-pyridinone trifluoroacetate;

3-Benzylsulfonylamino-1-[(2-guanidinooxyethyl)aminocarbonylmethyl]-2-pyridinone trifluoroacetate;

3-(3-Methylphenylsulfonyl)amino-6-methyl-1-[(2-guanidinooxyethyl)aminocarbonylmethyl]-2-pyridinone trifluoroacetate;

3-(Benzyloxycarbonyl)amino-6-methyl-1-[(2-guanidinooxyethyl)aminocarbonylmethyl]-2-pyridinone trifluoroacetate;

3-(Benzylsulfonyl)amino-6-methyl-1-[(1-(1-guanidinooxymethyl)cyclopropyl)aminocarbonylmethyl]-2-pyridinone trifluoroacetate;

3 (Benzylsulfonyl)amino-methyl-1-[(4-guanidinooxy)piperidinylcarbonylmethyl]-2-pyridinone trifluoroacetate;

3-(3-Chlorobenzylsulfonyl)amino-6-methyl-1-[(2-guanidinooxyethyl)aminocarbonylmethyl]-2-pyridinone trifluoroacetate;

3-(3-Trifluoromethylbenzylsulfonyl)amino-6-methyl-1-[(2-guanidinooxyethyl)aminocarbonylmethyl]-2-pyridinone trifluoroacetate;

3-(2-Trifluoromethylbenzyl)sulfonylamino-6-methyl-1-[(2-guanidinooxyethyl)aminocarbonylmethyl]-2-pyridinone trifluoroacetate;

3-(2-Iodobenzylsulfonyl)amino-6-methyl-1-[(2-guanidinooxyethyl)aminocarbonylmethyl]-2-pyridinone trifluoroacetate;

3-(2-Chlorobenzylsulfonyl)amino-6-methyl-1-[(2-guanidinooxyethyl)aminocarbonylmethyl]-2-pyridinone trifluoroacetate;

3-(2-Bromobenzylsulfonyl)amino-6-methyl-1-[(2-guanidinooxyethyl)aminocarbonylmethyl]-2-pyridinone trifluoroacetate;

3-(3-Fluorobenzylsulfonyl)amino-6-methyl-1-[(2-guanidinooxyethyl)aminocarbonylmethyl]-2-pyridinone trifluoroacetate;

3-(4-Chlorobenzylsulfonyl)amino-6-methyl-1-[(2-guanidinooxyethyl)aminocarbonylmethyl]-2-pyridinone trifluoroacetate;

3-((2-Chloro-6-fluoro)benzylsulfonyl)amino-6-methyl-1-[(2-guanidinooxyethyl)aminocarbonylmethyl]-2-pyridinone trifluoroacetate;

3-(2-Fluorobenzylsulfonyl)amino-6-methyl-1-[(2-guanidinooxyethyl)aminocarbonylmethyl]-2-pyridinone trifluoroacetate;

3-(2,3-Dichlorobenzylsulfonyl)amino-6-methyl-1-[(2-guanidinooxyethyl)aminocarbonylmethyl]-2-pyridinone trifluoroacetate;

3-(3,4-Difluorobenzylsulfonyl)amino-6-methyl-1-[(2-guanidinooxyethyl)aminocarbonylmethyl]-2-pyridinone trifluoroacetate;

3-(2,4-Dichlorobenzylsulfonyl)amino-6-methyl-1-[(2-guanidinooxyethyl)aminocarbonylmethyl]-2-pyridinone trifluoroacetate;

3-(2,5-Dichlorobenzylsulfonyl)amino-6-methyl-1-[(2-guanidinooxyethyl)aminocarbonylmethyl]-2-pyridinone trifluoroacetate;

3-(3,4-Dichlorobenzylsulfonyl)amino-6-methyl-1-[(2-guanidinooxyethyl)aminocarbonylmethyl]-2-pyridinone trifluoroacetate;

3-(1-naphthalenylmethylsulfonyl)aminomethyl-1-[(2-guanidinooxyethyl)aminocarbonylmethyl]-2-pyridinone trifluoroacetate;

3-(2-naphthalenylmethylsulfonyl)amino-6-methyl-1-[(2-guanidinooxyethyl)aminocarbonylmethyl]-2-pyridinone trifluoroacetate;

3-(2-Methylbenzylsulfonyl)amino-6-methyl-1-[(2-guanidinooxyethyl)aminocarbonylmethyl]-2-pyridinone trifluoroacetate;

3-(3-Chlorobenzylsulfonyl)-N-methylamino-6-methyl-1-[(2-guanidinooxyethyl)aminocarbonylmethyl]-2-pyridinone trifluoroacetate;

3-(3,4-Dichlorobenzylsulfonyl)-N-methylamino-6-methyl-1-[(2-guanidinooxyethyl)aminocarbonylmethyl]-2-pyridinone trifluoroacetate;

3-(2-Chlorophenylsulfonyl)amino-6-methyl-1[(2-guanidinooxyethyl)aminocarbonylmethyl]-2-pyridinone trifluoroacetate;

3-(4-Chlorophenylsulfonyl)amino-6-methyl-1-[(2-guanidinooxyethyl)aminocarbonylmethyl]-2-pyridinone trifluoroacetate;

3-(Phenylsulfonyl)amino-6-methyl-1-[(2-guanidinooxyethyl)aminocarbonylmethyl]-2-pyridinone trifluoroacetate;

3-(3-Chlorophenylsulfonyl)amino-6-methyl-1-[(2-guanidinooxyethyl)aminocarbonylmethyl]-2-pyridinone trifluoroacetate;

3-(2-Methylsulfonylphenyl)sulfonylamino-6-methyl-1-[(2-guanidinooxyethyl)aminocarbonylmethyl]-2-pyridinone trifluoroacetate;

3-(2-Naphthalenylsulfonyl)amino-6-methyl-1-[(2-guanidinooxyethyl)aminocarbonylmethyl]-2-pyridinone trifluoroacetate;

3-(4-Bromophenylsulfonyl)amino-6-methyl-1-[(2-guanidinooxyethyl)aminocarbonylmethyl]-2-pyridinone trifluoroacetate;

3-(4-Fluorophenylsulfonyl)amino-6-methyl-1-[(2-guanidinooxyethyl)aminocarbonylmethyl]-2-pyridinone trifluoroacetate;

3-(4-Iodophenylsulfonyl)amino-6-methyl-1-[(2-guanidinooxyethyl)aminocarbonylmethyl]-2-pyridinone trifluoroacetate;

3-(4-Methoxyphenylsulfonyl)amino-6-methyl-1-[(2-guanidinooxyethyl)aminocarbonylmethyl]-2-pyridinone trifluoroacetate;

3-(4-Methylphenylsulfonyl)amino-6-methyl-1-[(2-guanidinooxyethyl)aminocarbonylmethyl]-2-pyridinone trifluoroacetate;

3-(3-Trifluoromethylphenylsulfonyl)amino-6-methyl-1-[(2-guanidinooxyethyl)aminocarbonylmethyl]-2-pyridinone trifluoroacetate;

3-(3,4-dichlorophenylsulfonyl)amino-6-methyl-1-[(2-guanidinooxyethyl)aminocarbonylmethyl]-2-pyridinone trifluoroacetate;

3-(3-Chloro-4-fluorophenylsulfonyl)amino-6-methyl-1-[(2-guanidinooxyethyl)aminocarbonylmethyl]-2-pyridinone trifluoroacetate;

3-(4-Isopropylphenylsulfonyl)amino-6-methyl-1-[(2-guanidinooxyethyl)aminocarbonylmethyl]-2-pyridinone trifluoroacetate;

3-(3-Fluorophenylsulfonyl)amino-6-methyl-1-[(2-guanidinooxyethyl)aminocarbonylmethyl]-2-pyridinone trifluoroacetate;

3-(3,5-Dichlorophenylsulfonyl)amino-6-methyl-1-[(2-guanidinooxyethyl)aminocarbonylmethyl]-2-pyridinone trifluoroacetate;

3-(3,4-Dimethoxyphenylsulfonyl)amino-methyl-1-[(2-guanidinooxyethyl)aminocarbonylmethyl]-2-pyridinone trifluoroacetate;

3-(2-Thienylsulfonyl)amino-6-methyl-1-[(2-guanidinooxyethyl)aminocarbonylmethyl]-2-pyridinone trifluoroacetate;

3-(1-Naphthalenylsulfonyl)amino-6-methyl-1-[(2-guanidinooxyethyl)aminocarbonylmethyl]-2-pyridinone trifluoroacetate;

3-2,4,6-Trimethylphenylsulfonyl)amino-6-methyl-1-[(2-guanidinooxyethyl)aminocarbonylmethyl]-2-pyridinone trifluoroacetate;

3-(2-Methylphenylsulfonyl)amino-6-methyl-1-[(2-guanidinooxyethyl)aminocarbonylmethyl]-2-pyridinone trifluoroacetate;

3-(2,5-Dimethylphenylsulfonyl)amino-6-methyl-1-[(2-guanidinooxyethyl)aminocarbonylmethyl]-2-pyridinone trifluoroacetate;

3-(2-Fluorophenylsulfonyl)amino-6-methyl-1-[(2-guanidinooxyethyl)aminocarbonylmethyl]-2-pyridinone trifluoroacetate;

3-(2-Chloro-6-methylphenylsulfonyl)amino-6-methyl-1-[(2-guanidinooxypropyl)aminocarbonylmethyl]-2-pyridinone trifluoroacetate;

3-(3-Bromo-6-methoxyphenylsulfonyl)amino-6-methyl-1-[(2-guanidinooxyethyl)aminocarbonylmethyl]-2-pyridinone trifluoroacetate;

3-(3-Chloro-2-methylphenylsulfonyl)amino-6-methyl-1-[(2-guanidinooxyethyl)aminocarbonylmethyl]-2-pyridinone trifluoroacetate;

3-2-Chloro-5-trifluoromethylphenylsulfonyl)amino-methyl-1-[(2-guanidinooxyethyl)aminocarbonylmethyl]-2-pyridinone trifluoroacetate;

3-(2,4-Dichlorophenylsulfonyl)amino-6-methyl-1-[(2-guanidinooxyethyl)aminocarbonylmethyl]-2-pyridinone trifluoroacetate;

3-(4-Vinylphenylsulfonyl)amino-6-methyl-1-[(2-guanidinooxyethyl)aminocarbonylmethyl]-2-pyridinone trifluoroacetate;

3-(2-Butoxy-5-(1,1-dimethylpropyl)phenylsulfonyl)amino-6-methyl-1-[(2-guanidinooxyethyl) aminocarbonylmethyl]-2-pyridinone trifluoroacetate;

3-(3-Nitrophenylsulfonyl)amino-6-methyl-1-[(2-guanidinooxyethyl)aminocarbonylmethyl]-2-pyridinone trifluoroacetate;

3-(4-Chloro-3-nitrophenylsulfonyl)amino-6-methyl-1-[(2-guanidinooxyethyl)aminocarbonylmethyl]-2-pyridinone trifluoroacetate;

3-(4-Methylcarbonylaminophenylsulfonyl)amino-6-methyl-1-[(2-guanidinooxyethyl)aminocarbonylmethyl]-2-pyridinone trifluoroacetate;

3-(4-tert-Butylphenylsulfonyl)amino-6-methyl-1-[(2-guanidinooxyethyl)aminocarbonylmethyl]-2-pyridinone trifluoroacetate;

3-(4-Trifluoromethylphenylsulfonyl)amino-6-methyl-1-[(2-guanidinooxyethyl)aminocarbonylmethyl]-2-pyridinone trifluoroacetate;

3-(3-Cyanophenylsulfonyl)amino-6-methyl-1-[(2-guanidinooxyethyl)aminocarbonylmethyl]-2-pyridinone trifluoroacetate;

3-(4-Methylsulfonylphenylsulfonyl)amino-6-methyl-1-[(2-guanidinooxyethyl)aminocarbonylmethyl]-2-pyridinone trifluoroacetate;

3-Dansylamino-6-methyl-1-[(2-guanidinooxyethyl)aminocarbonylmethyl]-2-pyridinone trifluoroacetate;

3-(Pentafluorophenylsulfonyl)amino-6-methyl-1-[(2-guanidinooxyethyl)aminocarbonylmethyl]-2-pyridinone trifluoroacetate;

3-(2,5-Dichlorophenylsulfonyl)amino-6-methyl-1-[(2-guanidinooxyethyl)aminocarbonylmethyl]-2-pyridinone trifluoroacetate;

3-(2-Nitrophenylsulfonyl)amino-6-methyl-1-[(2-guanidinooxyethyl)aminocarbonylmethyl]-2-pyridinone trifluoroacetate;

3-Di(4-nitrophenylsulfonyl)amino-6-methyl-1-[(2-guanidinooxyethyl)aminocarbonylmethyl]-2-pyridinone trifluoroacetate;

3-(2,5-Dimethoxyphenylsulfonyl)amino-6-methyl-1-[(2-guanidinooxyethyl)aminocarbonylmethyl]-2-pyridinone trifluoroacetate;

3-(4-Propylphenylsulfonyl)amino-6-methyl-1-[(2-guanidinooxyethyl)aminocarbonylmethyl]-2-pyridinone trifluoroacetate;

3-2-Methyl-5-nitrophenylsulfonyl)amino-6-methyl-1-[(2-guanidinooxyethyl)aminocarbonylmethyl]-2-pyridinone trifluoroacetate;

3-(2-Trifluoromethylphenylsulfonyl)amino-6-methyl-1-[(2-guanidinooxyethyl)aminocarbonylmethyl]-2-pyridinone trifluoroacetate;

3-(2,3-Dichlorophenylsulfonyl)amino-6-methyl-1-[(2-guanidinooxyethyl)aminocarbonylmethyl]-2-pyridinone trifluoroacetate;

3-(2-Trifluoromethoxyphenylsulfonyl)amino-6-methyl-1-[(2-guanidinooxyethyl)aminocarbonylmethyl]-2-pyridinone trifluoroacetate;

3-(4-(3-Chloro-2-cyanophenoxy)phenylsulfonyl)amino-6-methyl-1-[(2-guanidino-oxyethyl) aminocarbonyhnethyl]-2-pyridinone trifluoroacetate;

3-(2-Chloro-4-fluorophenylsulfonyl)amino-6-methyl-1-[(2-guanidinooxyethyl)aminocarbonylmethyl]-2-pyridinone trifluoroacetate;

3-(3-Chloro-6-methoxyphenylsulfonyl)amino-6-methyl-1-[(2-guanidinooxyethyl)aminocarbonylmethyl]-2-pyridinone trifluoroacetate;

3-(2-Methoxy-5-methylphenylsulfonyl)amino-6-methyl-1-[(2-guanidinooxyethyl)aminocarbonylmethyl]-2-pyridinone tifluoroacetate;

3-(4-Phenylphenylsulfonyl)amino-6-methyl-1-[(2-guanidinooxyethyl)aminocarbonylmethyl]-2-pyridinone trifluoroacetate;

3-(5-Chlorothiophene-2-sulfonyl)amino-6-methyl-1-[(2-guanidinooxyethyl)aminocarbonylmethyl]-2-pyridinone trifluoroacetate;

3-6-Chloronaphthalene-2-sulfonyl)amino-6-methyl-1-[2-guanidinooxyethyl)aminocarbonylmethyl]-2-pyridinone trifluoroacetate;

3-(6-Bromonaphthalene-2-sulfonyl)amino-6-methyl-1-[(2-guanidinooxyethyl)aminocarbonylmethyl]-2-pyridinone trifluoroacetate;

3-(3-Bromophenylsulfonyl)amino-6-methyl-1-[(2-guanidinooxyethyl)aminocarbonylmethyl]-2-pyridinone trifluoroacetate;

3-(Quinoline-8-sulfonyl)amino-6-methyl-1-[(2-guanidinooxyethyl)aminocarbonylmethyl]-2-pyridinone trifluoroacetate;

3-(Quinoline-5-sulfonyl)amino-6-methyl-1-[(2-guanidinooxyethyl)aminocarbonylmethyl]-2-pyridinone trifluoroacetate;

3-(1-Methylimidazole-4-sulfonyl)amino-6-methyl-1-[(2-guanidinooxyethyl)aminocarbonylmethyl]-2-pyridinone trifluoroacetate;

3-(3-Methylquinoline-8-sulfonyl)amino-6-methyl-1-[(2-guanidinooxyethyl)aminocarbonylmethyl]-2-pyridinone trifluoroacetate;

3-(2-Pyridinylsulfonyl)amino-6-methyl-1-[(2-guanidinooxyethyl)aminocarbonylmethyl]-2-pyridinone trifluoroacetate;

3-(3-Pyridinylsulfonyl)amino-6-methyl-1-[(2-guanidinooxypropyl)aminocarbonylmethyl]-2-pyridinone trifluoroacetate;

3-(4-Ethylphenylsulfonyl)amino-6-methyl-1-[(2-guanidinooxyethyl)aminocarbonylmethyl]-2-pyridinone trifluoroacetate;

3-(3-Methylphenylsulfonyl)amino-6-methyl-1-[(2-guanidinooxyethyl)-N-methylaminocarbonylmethyl]-2-pyridinone trifluoroacetate;

3-3-Methylphenylsulfonyl)amino-6-isopropyl-1-[(2-guanidinooxyethyl)aminocarbonylmethyl]-2-pyridinone trifluoroacetate;

3-(3-Methylphenylsulfonyl)amino-6-ethyl-1-[(2-guanidinooxyethyl)aminocarbonylmethyl]-2-pyridinone trifluoroacetate;

3-(3-Methylphenylsulfonyl)amino-6-propyl-1-{2-(guanidinyloxyethyl)aminocabonylmethyl}-2-pyridinone trifluoroacetate;

3-(3-Methylphenylsulfonyl)amino-6-methyl-1-[(2-N'''-methylguanidinooxyethyl)aminocarbonylmethyl]-2-pyridinone hydrochloride;

3-(3-Methylphenylsulfonyl)amino-6-methyl-1-[(2-N'''-ethylguanidinooxyethyl)aminocarbonylmethyl]-2-pyridinone hydrochloride;

3-(3-Methylphenylsulfonyl)amino-6-methyl-1-[(2-N'''-benzylguanidinooxyethyl)aminocarbonylmethyl]-2-pyridinone hydrochloride;

3-(3-Methylphenylsulfonyl)amino-6-methyl-1-[(2-N'''-butylguanidinooxyethyl)aminocarbonylmethyl]-2-pyridinone hydrochloride;

3-(3-Methylphenylsulfonyl)amino-6-methyl-1-[(2-N-methylguanidinooxyethyl)aminocarbonylmethyl]-2-pyridinone trifluoroacetate;

3-(Benzylsulfonyl)amino-6-methyl-1-[(2-N-methylguanidinooxyethyl)aminocarbonylmethyl]-2-pyridinone trifluoroacetate;

3-(3-Methylphenylsulfonyl)amino-6-methyl-1-[(2-(N-methoxycarbonyl)guanidino-oxyethyl)aminocarbonylmethyl]-2-pyridinone;

3-(3-Methylphenylsulfonyl)amino-6-methyl-1-[(2-(N,N',N''-triethoxycarbonyl)guanidino-oxyethyl)aminocarbonylmethyl]-2-pyridinone;

3-(3-Methylphenylsulfonyl)amino-6-methyl-1-[(2-(N,N'-diethoxycarbonyl)guanidino-oxyethyl)aminocarbonylmethyl]-2-pyridinone; and 3-(3-Methylphenylsulfonyl)amino-6-methyl-1-[(2-N-ethoxycarbonyl)guanidinooxyethyl)aminocarbonylmethyl]-2-pyridinone.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The compounds of Formula VII may also be solvated, especially hydrated. Hydration may occur during manufacturing of the compounds or compositions comprising the compounds, or the hydration may occur over time due to the hygroscopic nature of the compounds.

Certain compounds within the scope of Formula VII are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process. Useful prodrugs are those where $R^a$, $R^b$ and/or $R^c$ are $—CO_2R^w$, where $R^w$ is defined above. See, U.S. Pat. No. 5,466,811 and Saulnier et al., *Bioorg. Med. Chem. Lett.* 4:1985-1990 (1994).

When any variable occurs more than one time in any constituent or in Formula VII, its definition on each occurrence is independent of its definition at every other occurrence. Also, combinations of substituents and/or variables are permissible only if such combinations result in stable compounds.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention includes methods which are useful for in vivo imaging or thrombi in a mammal.

According to a preferred aspect, useful compounds are those wherein the $R^1$ substituent is substituted with a detectable label, such as a radioactive iodine atom, such as I-125, I-131 or I-123. In this aspect, $R^1$ is preferably phenyl, having a para I-123, para I-125 or para I-131 substitution, or benzyl, having a meta I-123, meta I-125 or meta I-131 substitution.

The detectable label can also be a radioactive or paramagnetic chelate in which a suitable ligand (L) is attached to an $R^1$ substituent, either directly or via a divalent linking group A''. Alternatively, the group -A''-L substitutes for the groups -Z-$R^1$ in Formula VII. By suitable ligand is meant an organic moiety that is capable of chelating a radioactive or paramagnetic metal ion.

In these compounds, the divalent linking group A'' includes groups that are capable of covalently bonding with a free amino group and the chelating means. For example, A'' may be $—C(=S)—$, $—C(=O)—$, $—C(=NH)—(CH_2)_6—C(=NH)—$, $—C(=O)—(CH_2)_6—C(=O)—$,

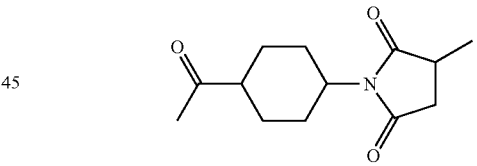

and the like.

Also, in the compounds represented by Formula VII, the chelating ligand, L, includes groups capable of covalently bonding to or noncovalently binding to either a radioactive or paramagnetic atom. The chelating means including those which are customarily used for complexing radioactive or paramagnetic atoms. These include chelating means containing 3 to 12, preferably 3 to 8, methylene phosphonic acid groups, methylene carbohydroxamic acid groups, carboxyethylidene groups, or especially carboxymethylene groups, which are bonded to a nitrogen atom. If only one or two of the acid groups are bonded to a nitrogen atom, then that nitrogen is bonded to another nitrogen atom having such groups by an optionally substituted ethylene groups or by up to four separated ethylene units separated by a nitrogen or oxygen or sulfur atom. Preferred as a completing means is diethylenetrimine-N,N,N',N'',N''-pentaacetic acid (DTPA). DTPA is well known in the art as a chelating means for the radioactive atom indium-111 (In-111), technetium-99m (Tc-99m), and the paramagnetic atom gadolinium (Gd). Khaw, et al., *Science* 209:295 (1980); Paik C. H. et al., U.S. Pat. No. 4,652,440 (1987); Gries, H. et al., U.S. Pat. No. 4,957,939 (1990). A preferred chelating ligand, L, is 1-(p-aminobenzyl)-diethylenetriaminepentaacetic acid. Also included as chelating means are compounds which contain sulfhydryl or amine moieties, the total of which in any combination is at least four. These sulfhydryl or amine moieties are separated from each other by at least two atoms which can be either carbon, nitrogen, oxygen, or sulfur. Especially preferred for chelating means, L, is metallothionein which is well known in the art as a chelating means for Tc-99m.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2-20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2-20 carbon atoms, unless the chain length is limited thereto, wherein there is at least one triple bond between two of the carbon atoms in the chain, including, but not limited to, acetylene, 1-propylene; 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6-10 carbons in the ring portion, such as phenyl, naphthyl or tetrahydronaphthyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$ alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "$C_{7-12}$ bicyclic alkyl" is intended to include bicyclo[2.2.1]heptyl (norbornyl), bicyclo[2.2.2]octyl, 1,1,3-trimethylbicyclo[2.2.1]heptyl (bornyl), and the like.

The terms "alkoxy" refers to any of the above alkyl groups linked to an oxygen atom.

The term "halogen" or "halo" as employed herein by itself or as part of another group refers to chlorine, bromine, fluorine or iodine with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heterocycle" or "heterocyclic ring", as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound, form a saturated or unsaturated 5-, 6-, or 7-membered ring.

Schemes 1 and 2 outline the synthesis of compounds of the present invention where $R^1$-Z- is $R^1$—$SO_2$—.

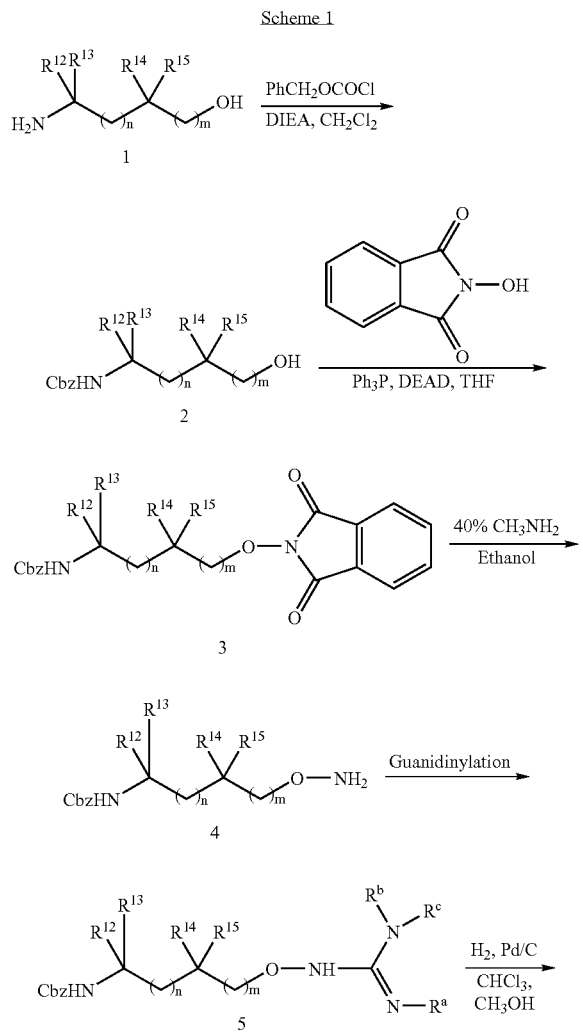

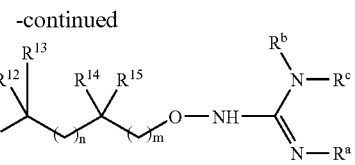

where $R^{12}$-$R^{15}$, $R^a$, $R^b$, $R^c$, n and m are as defined above.

In Scheme 1, an aminoalcohol 1 is protected using a standard amino protecting group such as benzyloxycarbonyl (Cbz) to give compound 2. The protected aminoalcohol 2 is coupled to N-hydroxyphthalimide using a Mitsunobu coupling procedure (Mitsunobu, O., *Synthesis*, 1 (1981)) to provide compound 3. Preferred coupling conditions include using a solvent, such as tetrahydrofuran or methylene chloride, and a dialkyl azodicarboxylate, such as diethyl azodicarboxylate. Unveiling of the phthalimide protecting group to form alkoxyamine 4 is accomplished using standard conditions well known in the art (Greene, T. W., Wuts, P. G. W., *Protecting Groups in Organic Synthesis*, 2nd edition, John Wiley and Sons, Inc. New York, (1991)), such as methylamine or hydrazine, in an appropriate solvent, such as ethanol or iso-propanol. Guanidinylation of the resulting alkoxyamine 4 to 5 is accomplished using substituted guanidinylating reagents such as N,N'-bis(tert-butoxycarbonyl)-S-methylthiourea (Bergeron, R. J. and McManis, J. S, *J. Org. Chem.*, 52:1700 (1987)) or N—$R^a$, N—$R^b$, N—$R^c$-1H-pyrazole-1-carboxamidine (Bernatowicz, M. S., et al., *Tetrahedron Letter* 34: 3389 (1993)). Deprotection of the amino protecting group to give intermediates 6 is accomplished using standard procedures well known in the art (Greene, T. W., Wuts, P. G. W., *Protecting Groups in Organic Synthesis*, 2nd edition, John Wiley and Sons, Inc. New York, (1991)), such as palladium on carbon, in a suitable solvent, such as chloroform in methanol or ethanol. In some cases, it is advantageous to add an acid, such as hydrochloric acid.

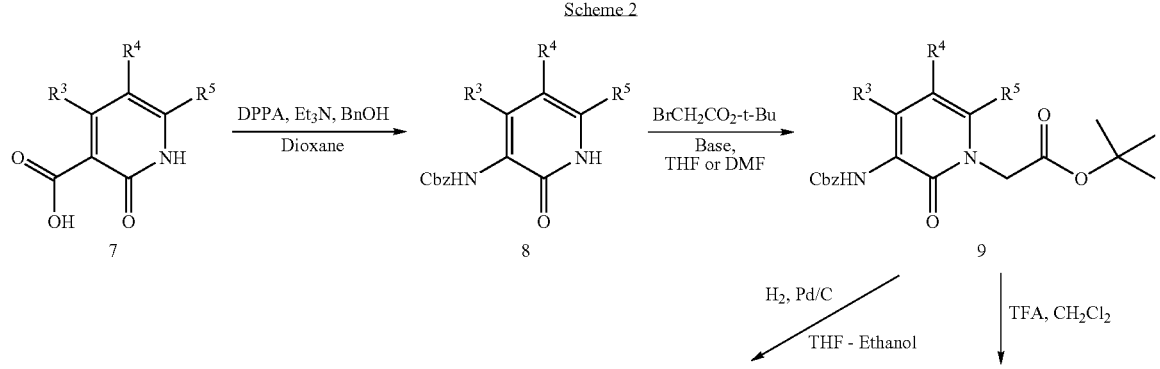

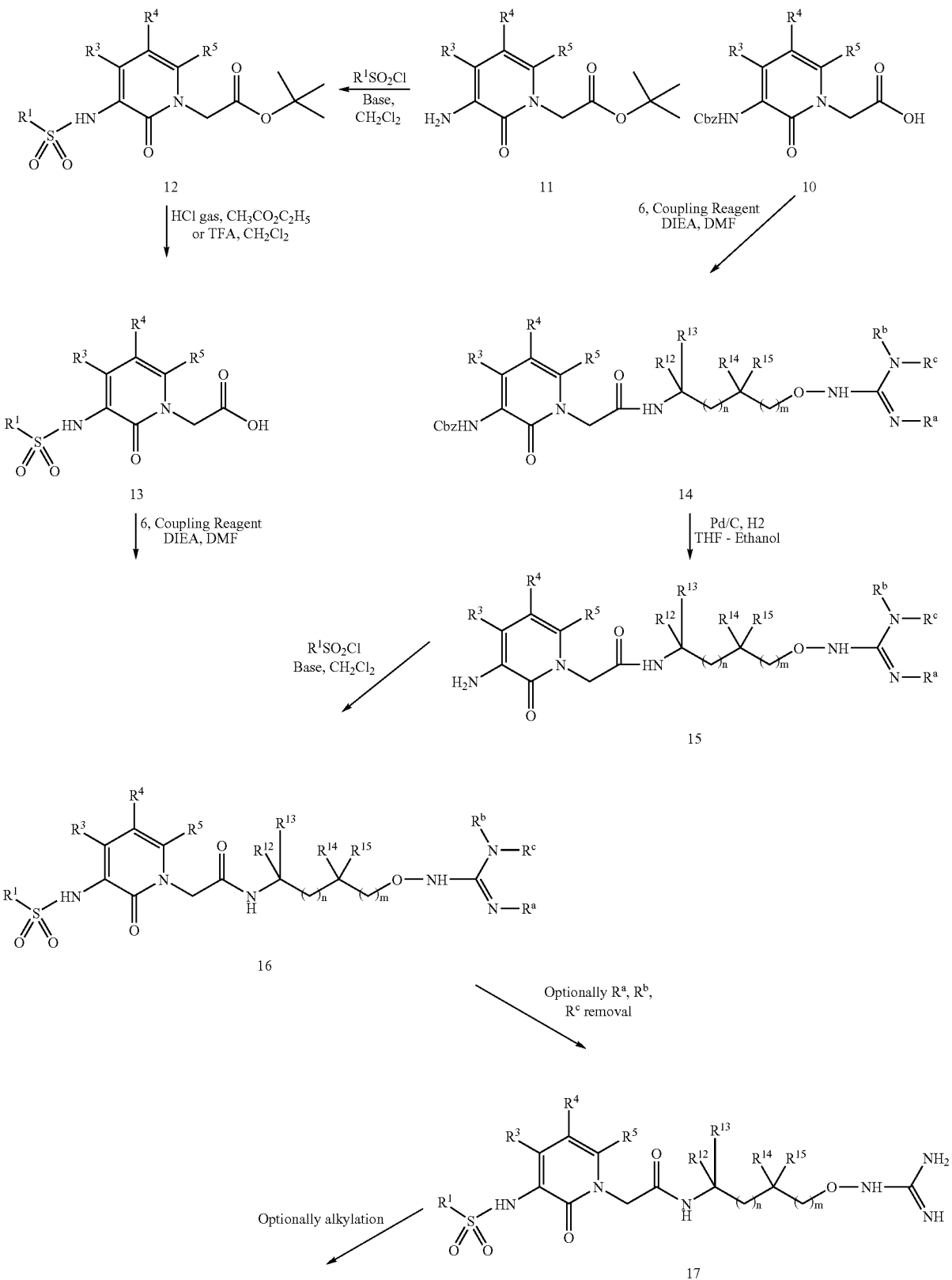

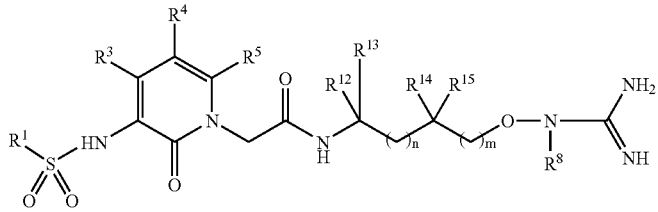

18 where $R^1$, $R^3$-$R^5$, $R^{12}$-$R^{15}$, $R^8$, $R^a$, $R^b$, $R^c$, n and m are defined above.

In Scheme 2, a 2-hydroxy-pyridine carboxylic acid 7 is reacted with diphenylphosphoryl azide (DPPA), triethylamine and benzyl alcohol in a suitable solvent, such as dioxane to afford the protected amino pyridinone 8. This is alkylated with a glycine equivalent, such as tert-butyl bromoacete, using a base, such as lithium hexamethyldisilazide, cesium carbonate, or sodium hydride, in an appropriate solvent, such as tetrahydrofuran or N,N-dimethylformamide to give compound 9. The tert-butyl group is then removed using standard conditions well known in the art (Greene, T. W., Wuts, P. G. W., *Protecting Groups in Organic Synthesis,* 2nd edition, John Wiley and Sons, Inc. New York, (1991)), such as HCl gas in ethyl acetate or trifluoroacetic acid in methylene chloride, to afford acid 10. The acid 10 is coupled to intermediate 6 using a standard peptide coupling reagents, such as Castro's reagent (BOP) or PyBOP, and base such as diisopropylethylamine in a suitable solvent, such as N,N-dimethylformamide to produce compound 14. The Cbz group is removed via hydrogenation over a catalyst such as palladium on carbon in a solvent, such as tetrahydofuran and ethanol. The amine 15 is treated with a sulfonyl chloride in the present of a base, such as 4-methylmorpholine, in a suitable solvent, such as methylene chloride to afford compound 16.

Alternatively, the Cbz group of compound 9 is deprotected using a standard procedure such as hydrogenation in the present of a catalyst such as palladium on carbon in an appropriate solvent, such as tetrahydrofuran and ethanol. The amine 11 is reacted with a sulfonyl chloride in the present of a base, such as 4-methylmorpholine, in a suitable solvent, such as methylene chloride to afford 12. The tert-butyl group is removed using standard procedure well known in the art (Greene, T. W., Wuts, P. G. W., *Protecting Groups in Organic Synthesis,* 2nd edition, John Wiley and Sons, Inc. New York, (1991)), such as HCl gas in ethyl acetate or trifluoroacetic acid in methylene chloride, to afford acid 13. The acid 13 is coupled to intermediate 6 using a standard peptide coupling reagents, such as Castro's reagent (BOP) or PyBOP, and a base such as diiso-propylethylamine, in a suitable solvent, such as N,N-dimethylformamide to give compound 16. The $R^a$, $R^b$ and $R^c$ can be optionally removed using a standard procedure. In the case of $R^a$ and $R^b$=tert-butoxycarbonyl (Boc) and $R^c$=hydrogen, the Boc groups can be removed by treatment with an acid, such as trifluoroacetic acid or hydrochloric acid, in an appropriate solvent, such as methylene chloride or dioxane to provide compound 17. Compound 17 can be then optionally alkylated with an alkyl halide in the present of a base, such as sodium bicarbonate, in an appropriate solvent, such as N,N'-dimethylformamide, to give compound 18.

Scheme 3

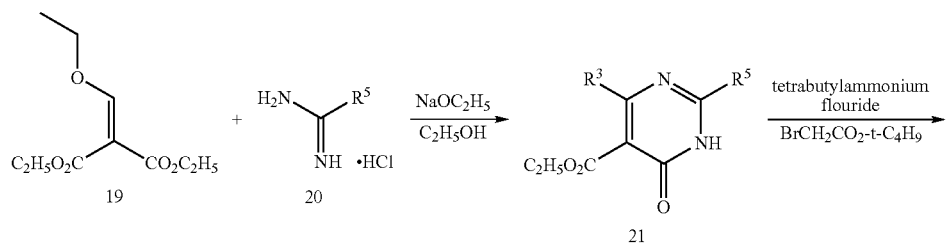

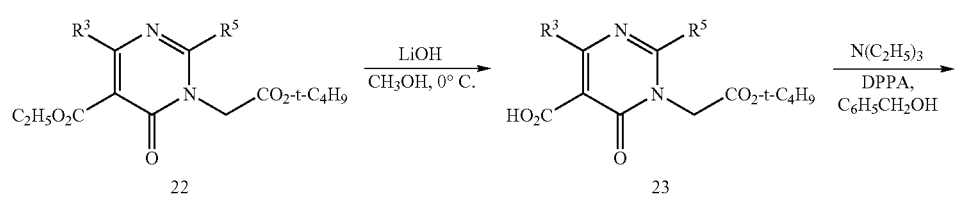

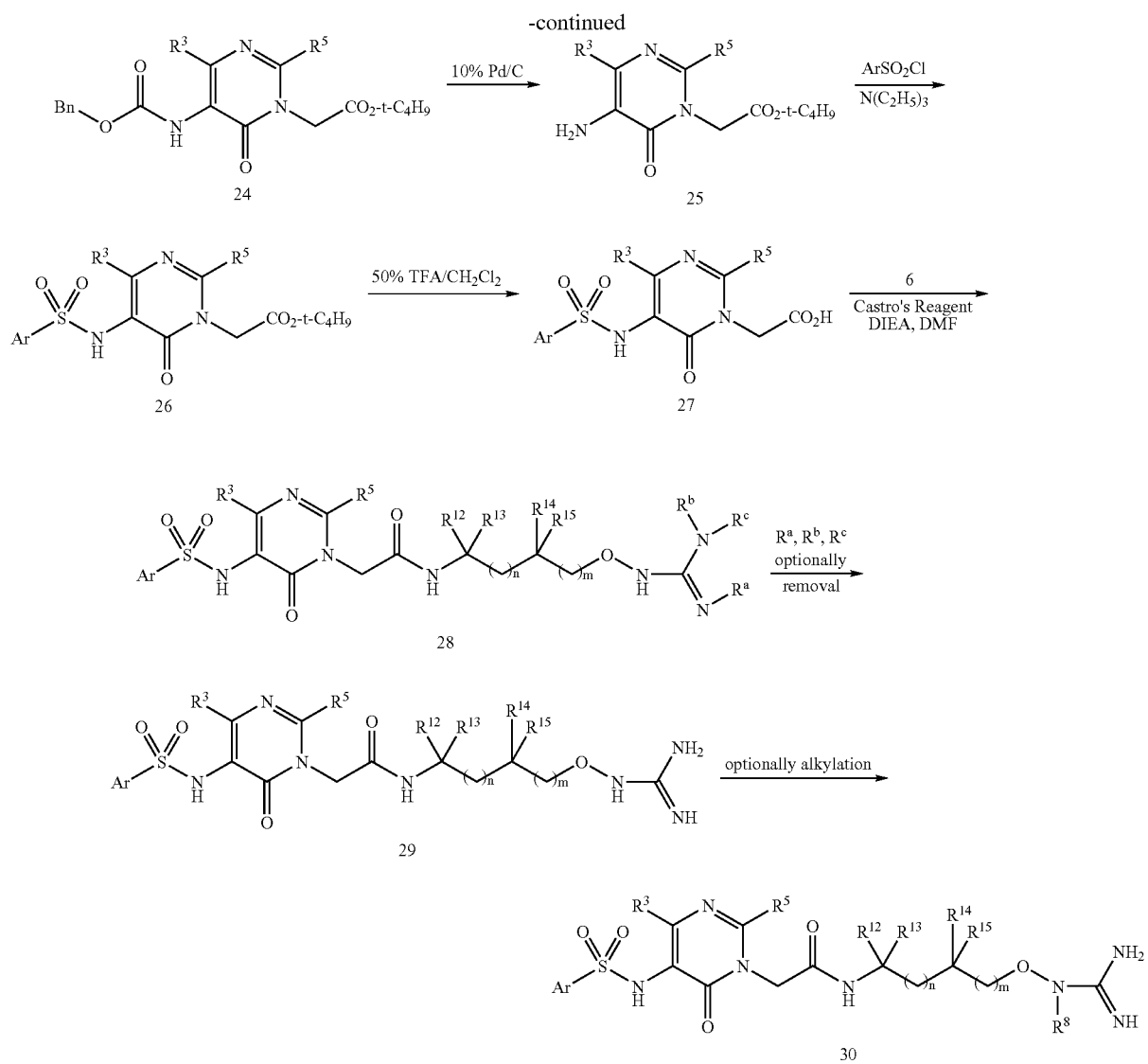

where $R^3$, $R^5$, $R^{12}$-$R^{15}$, $R^a$, $R^b$, $R^c$, n, and m are defined above, and Ar is aryl.

In Scheme 3, diethyl ethoxymethylenemalonate 19 is treated with amidine 20 in the present of base, such as sodium ethoxide, in an appropriate solvent, such as ethanol to afford substituted pyrimidine 21. Compound 21 is alkylated with a glycine equivalent, such as tert-butyl bromoacetate, using a base, such as tetrabutylammonium fluoride, lithium hexamethyldisilazide, or sodium hydride, in an appropriate solvent, such as tetrahydrofuran or N,N-dimethylformamide to give ester 22. The ester is hydrolyzed with lithium hydroxide or sodium hydroxide in a suitable solvent, such as methanol or ethanol, to afford acid 23. The acid is then treated with diphenylphosphoryl azide (DPPA) in the present of base, such as triethylamine, to form the acyl azide which undergoes the Curtius rearrangement reaction with benzyl alcohol to form the benzyloxycarbonyl (Cbz) protected 5-aminopyrimidone 24. The Cbz group of compound 24 is deprotected using a standard procedure such as hydrogenation in the present of a catalyst, such as palladium on carbon in an appropriate solvent, such as tetrahydrofuran and ethanol. The amine 25 is treated with a sulfonyl chloride in the present of a base, such as 4-methylmorpholine or triethylamine, in a suitable solvent, such as methylene chloride to afford 26. The tert-butyl group is removed using a standard procedure well known in the art (Greene, T. W., Wuts, P. G. W., *Protecting Groups in Organic Synthesis*, 2nd edition, John Wiley and Sons, Inc. New York, (1991)), such as trifluoroacetic acid in methylene chloride, to afford acid 27. The acid 27 is coupled to intermediate 6 using standard peptide coupling reagents, such as Castro's reagent (BOP) or PyBOP, and a base, such as diiso-propylethylamine or triethylamine, in a suitable solvent, such as N,N-dimethylformamide to give compound 28. The $R^a$, $R^b$ and $R^c$ can be optionally removed using a standard procedure. In the case of $R^a$ and $R^b$=tert-butoxycarbonyl (Boc) and $R^c$=hydrogen, the Boc groups can be removed by treatment with an acid, such as trifluoroacetic acid or hydrochloric acid, in an appropriate solvent, such as methylene chloride or dioxane to provide compound 29. Compound 29 can be optionally alkylated with an alkyl halide in the present of a base, such as sodium bicarbonate, in a suitable solvent, such as N,N-dimethylformamide, to give compound 30.

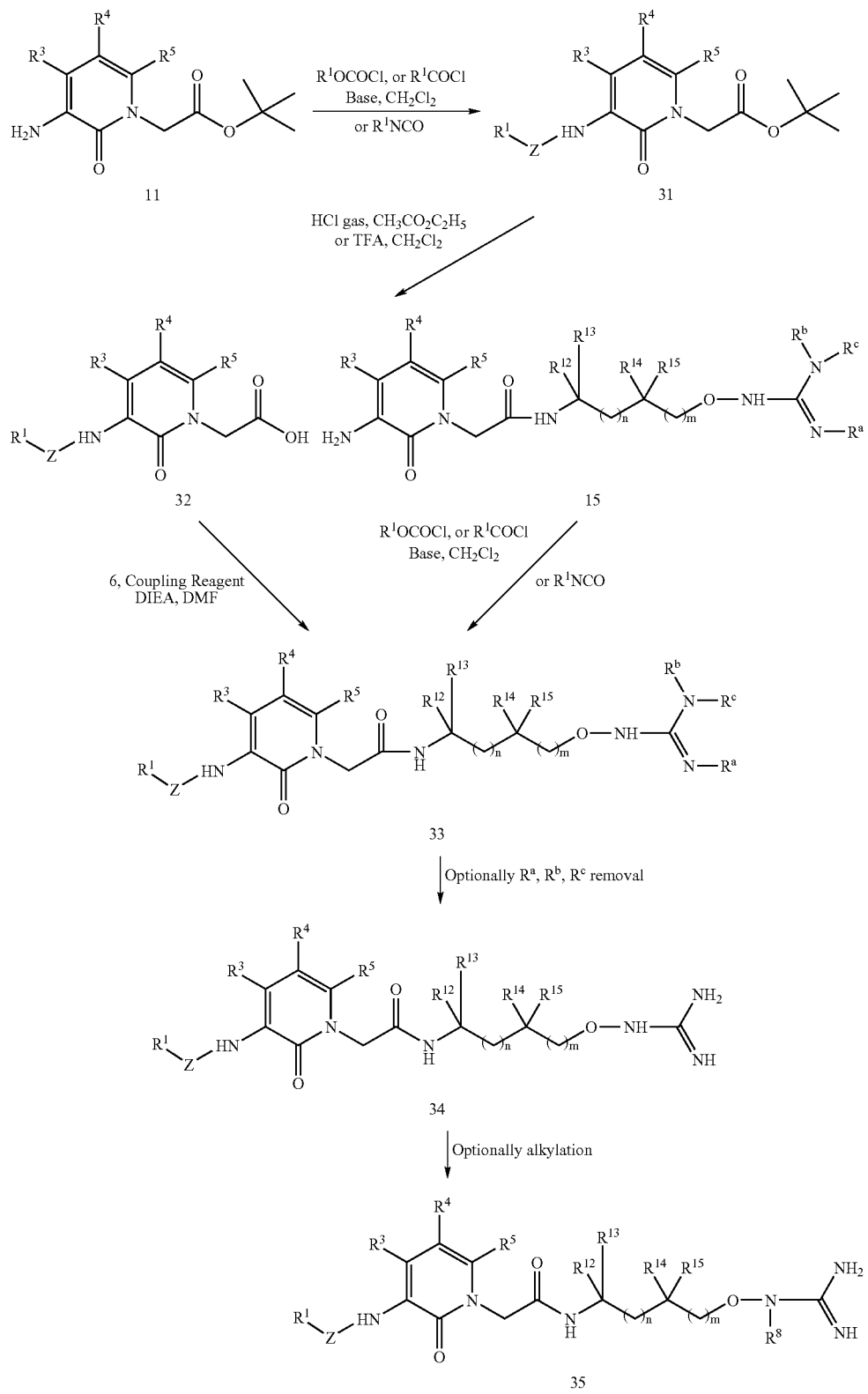
Scheme 4

Scheme 4 illustrates the preparation of compounds of the present invention where Z=—OCO—, —CO— or —NR²CO—. The amine 11 is reacted with an alkoxy carbonyl chloride, or a aryloxy carbonyl chloride, or a acyl chloride in the present of a base, such as 4-methylmorpholine or triethylamine, in a suitable solvent, such as methylene chloride, or treated with a isocyanate in an appropriate solvent, such as methylene chloride or toluene, to afford 31. The tert-butyl group is removed using standard procedures well known in the art (Greene, T. W., Wuts, P. G. W., *Protecting Groups in Organic Synthesis,* 2nd edition, John Wiley and Sons, Inc. New York, (1991)), such as HCl gas in ethyl acetate or trifluoroacetic acid in methylene chloride, to afford acid 32. The acid 32 is coupled to intermediate 6 using a standard peptide coupling reagent, such as Castro's reagent (BOP) or PyBOP, and a base such as diisopropylethylamine, in a suitable solvent, such as N,N-dimethylformamide, to give compound 33. Alternatively, the amine 15 is treated with an alkoxy carbonyl chloride, aryloxy carbonyl chloride or acyl chloride in the present of a base, such as 4-methylmorpholine or triethylemine, in a suitable solvent, such as methylene chloride, or treated with a isocyanate in an appropriate solvent, such as methylene chloride or toluene, to afford compound 33. The $R^a$, $R^b$ and $R^c$ can be optionally removed using a standard procedure. In the case of $R^a$ and $R^b$=tert-butoxycarbonyl (Boc) and $R^c$=hydrogen, the Boc groups can be removed by treatment with an acid, such as trifluoroacetic acid or hydrochloric acid, in an appropriate solvent, such as methylene chloride or dioxane, to provide compound 34. The compound 34 can be then optionally alkylated with an alkyl halide in the present of a base, such as sodium bicarbonate, in an appropriate solvent, such as N,N-dimethylformamide, to give compound 35.

Schemes 5 and 6 provide examples of intermediates and synthetic steps described in Schemes 1 and 2 to produce compounds of Formula VII where $R^1$-Z is $R^1$—$SO_2$—. The variable "m" in the schemes has a value of from 0 to 8, preferably 0 or 1. The synthetic steps in these schemes are exemplified in Examples 1 and 2 herein.

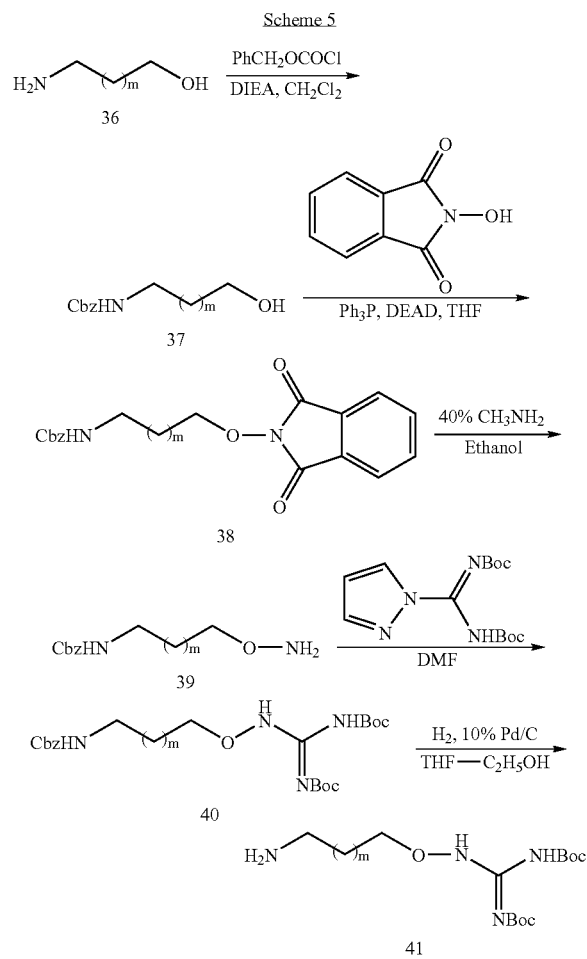

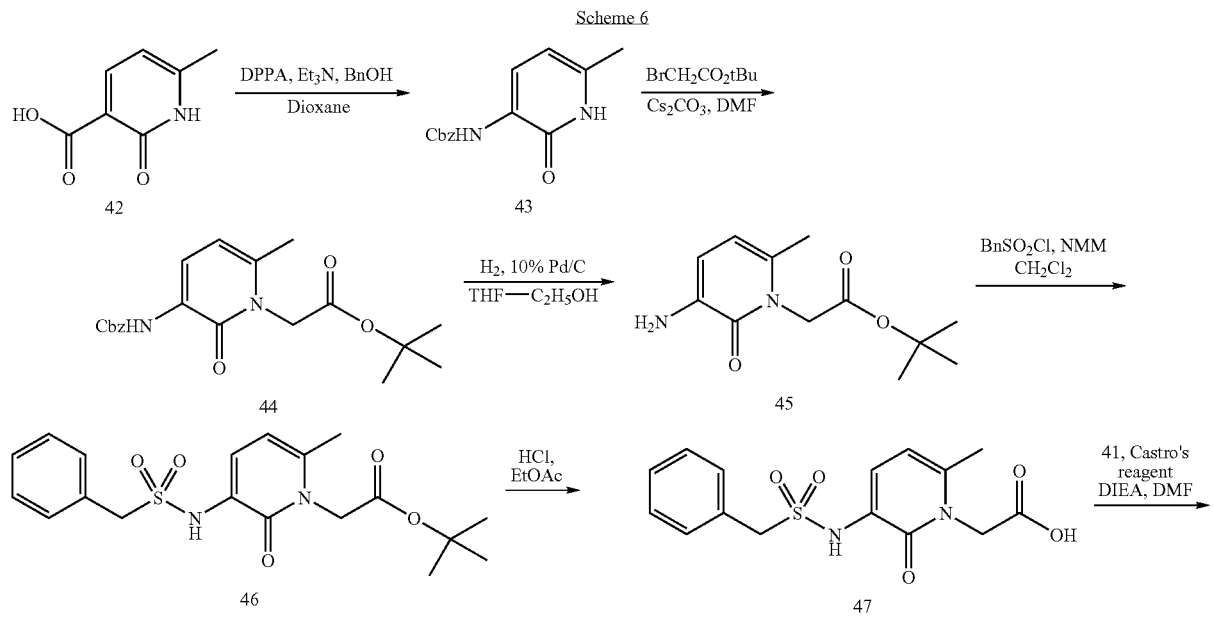

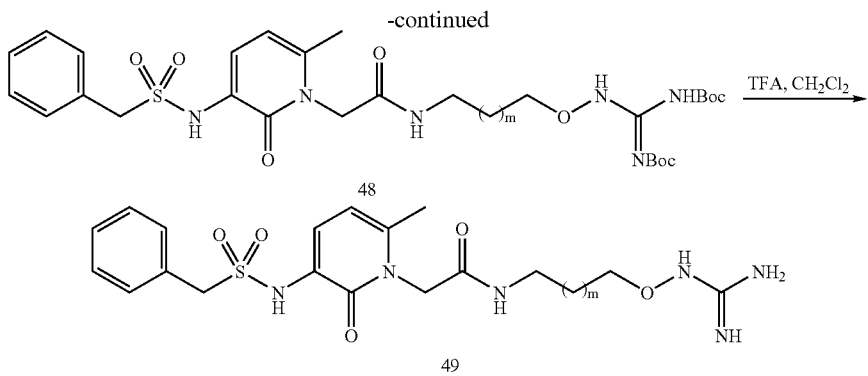

The pharmaceutically-acceptable salts of the compounds of Formula VII (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Preferred acids for forming acid addition salts include HCl and acetic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to inhibit trypsin-like proteases.

An end use application of the compounds that inhibit chymotrypsin and trypsin is in the treatment of pancreatitis. For their end-use application, the potency and other biochemical parameters of the enzyme-inhibiting characteristics of the compounds of the present invention is readily ascertained by standard biochemical techniques well known in the art. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit thrombin may be employed for a number of therapeutic purposes. As thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA). Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, and blood lines. The compounds of the present invention may also be used as an anticoagulant in extracorporeal blood circuits.

Metal stents have been shown to reduce restenosis, but are thrombogenic. A strategy for reducing the thrombogenicity of stents is to coat, embed, adsorb or covalently attach a thrombin-inhibiting agent to the stent surface. The compounds of the present invention can be employed for this purpose. Compounds of the invention can be attached to, or embedded within soluble and/or biodegradeable polymers as and thereafter coated onto stent materials. Such polymers can include polyvinylpyrrolidone, polyhydroxy-propylmethacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent 2,164,684 and PCT Published Applications WO 96/11668, WO 96/32143 and WO 96/38136.

By virtue of the effects of thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement The compounds of the present invention may be useful in treating neoplasia and metastasis as well as neurodegenerative diseases, such as Alzheimer's disease and Parkinson's disease.

When employed as thrombin inhibitors, the compounds of the present invention may be administered in an effective amount within the dosage range of about 0.1 to about 500 mg/kg, preferably between 0.1 to 10 mg/kg body weight, on a regimen in single or 2-4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

The thrombin inhibitors may also be coupled with soluble polymers as targetable drug carriers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Human leucocyte elastase is released by polymorphonuclear leukocytes at sites of inflammation and thus is a contributing cause for a number of disease states. Compounds of the present invention are expected to have an anti-inflammatory effect useful in the treatment of gout, rheumatoid arthritis and other inflammatory diseases, and in the treatment of emphysema. The leucocyte elastase inhibitory properties of compounds of the present invention are determined by the method described below. Cathepsin G has also been implicated in the disease states of arthritis, gout and emphysema, and in addition, glomerulonephritis and lung infestations caused by infections in the lung. In their end-use application the enzyme inhibitory properties of the compounds of Formula I is readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15:836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4° C. A protein fraction precipitates during dialysis and is isolated by centrifugation. This fraction contains most of the chymotrypsin-like activity of leukocyte granules. Specific substrates are prepared for each enzyme, namely N-Suc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10 M Hepes buffer, pH 7.5, containing 0.50 M NaCl, 10% dimethylsulfoxide and 0.0020 M Suc-Ala-Ala-Pro-Phe-p-nitroanilide as a substrate. Hydrolysis of the p-nitroanilide substrate is monitored at 405 nm and at 25° C.

Useful dose range for the application of compounds of the present invention as neutrophil elastase inhibitors and as Cathepsin G inhibitors depend upon the nature and severity of the disease state, as determined by the attending diagnostician, with a range of 0.01 to 10 mg/kg body weight, per day, being useful for the aforementioned disease states.

Compounds of the present invention that inhibit urokinase or plasminogen activator are potentially useful in treating excessive cell growth disease state. As such compounds of the present invention may also be useful in the treatment of benign prostatic hypertrophy and prostatic carcinoma, the treatment of psoriasis, and as abortifacients. For their end-use application, the potency and other biochemical parameters of the enzyme inhibiting characteristics of compounds of the present invention are readily ascertained by standard biochemical techniques well known in the art. Actual dose ranges for this application will depend upon the nature and severity of the disease state of the patient or animal to be treated as determined by the attending diagnostician. It is to be expected that a general dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of these assays by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropyl-methylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Compounds of Formula VII can be labeled with radioactive iodine as described below in Example 3 or by using an exchange reaction. Exchange of hot iodine for cold iodine is well known in the art Alternatively, a radio iodine labeled compound can be prepared from the corresponding bromo compound via a tributylstannyl intermediate. See, U.S. Pat. No. 5,122,361, herein incorporated by reference.

The present invention also includes compositions which are useful for in vivo imaging of thrombi in a mammal, wherein the compositions are comprised of a compound of Formula VII complexed with a radioactive atom.

For the compounds of Formula VII, suitable radioactive atoms include Co-57, Cu-67, Ga-67, Ga-68, Ru-97, Tc-99m, In-111, In-113m, Hg-197, Au-198, and Pb-203. In particular, technetium-99m (Tc-99m) is an ideal radioactive atom for imaging because of its nuclear properties. It is a gamma emitter and has a single photon energy of 140 keV, a half-life of about 6 hours, and it is readily available from a Mo-99/Tc-99 generator. Rhenium-186 and -188 also have gamma emission which allows them to be imaged. Preferred compositions contain the radioactive atom, Tc-99m.

Compositions of the present invention are conveniently prepared by completing a compound of Formula VII with radioisotopes which are suitable for detection externally.

The compounds of Formula VII can be labeled by any of the many techniques known in the art to provide a composition of the present invention. For example, these compounds can be labeled through a chelating agent such as diethylenetriaminepentaacetic acid (DTPA) or metallothionein, both of which can be covalently attached to the compound of Formula VII.

In general, the compositions of the present invention containing technetium-99m are prepared by forming an aqueous mixture of technetium-99m and a reducing agent and a water-soluble ligand, and then contacting the mixture with a compound of the present invention represented by Formula VII. For example, the imaging compounds of this invention are made by reacting technetium-99m (in an oxidized state) with the compounds of the present invention having a chelating means in the presence of a reducing agent to form a stable complex between technetium-99m in a reduced state (IV or V valence state).

One embodiment of the composition of the present invention is prepared by labeling a compound of Formula VII having a DTPA chelating means with technetium-99m. This may be accomplished by combining a predetermined amount (as 5 µg to 0.5 mg) of compound of the present invention with an aqueous solution containing citrate buffer and stannous reducing agent, then adding freshly eluted sodium pertechnetate containing a predetermined level of radioactivity (as 15 mCi). After allowing an incubation of the mixture at room temperature, the reaction mixture is loaded into a shielded syringe through a sterile filter (0.2-0.22 micron), then is dispensed into 0.9% saline for injection, if desired.

Another embodiment of the compositions of the present invention is prepared by labeling a compound of Formula VII having a metallothionein chelating means with technetium-99m. This may be accomplished by combining aqueous sodium pertechnetate-99m with aqueous stannous glucoheptonate to form a soluble complex of technetium-99m (in reduced state) with two glucoheptonate molecules, then combining this solution with a compound of the Formula VII having a metallothionein attached thereto. After incubating the mixture for a period of time and under conditions which allow for an exchange of the technetium-99m from the glucoheptonate complex to the metallothionein of the compound of Formula VII, the technetium-labeled composition of the present invention is formed.

The source of technetium-99m should preferably be water soluble. Preferred sources are alkali and alkaline earth metal pertechnetate ($TcO_4^-$). Technetium-99m is most preferably obtained in the form of fresh sodium pertechnetate from a sterile technetium-99m generator (as from a conventional Mo-99/Tc-99m generator). However, any other source of physiologically acceptable technetium-99m may be used.

Reducing agents for use in the method are physiologically acceptable for reducing technetium-99m from its oxidized state to the IV or V valence state or for reducing rhenium from its oxidized state. Reducing agents which can be used are stannous chloride, stannous fluoride, stannous glucoheptonate, stannous tartarate, and sodium dithionite. The preferred agents are stannous reducing agents, especially stannous chloride or stannous glucoheptonate. For example, stannous chloride ($SnCl_2$) is the reducing agent and can be used in range from 1-1,000 µg/mL. Especially preferred concentrations are about 30-500 µg/mL.

Citric acid complexes with technetium-99m to quickly form a stable technetium-99m-citrate complex. Upon contact with a compound of Formula VII, substantially quantitative transfer of technetium-99m from its citrate complex to the chelating means of the compound of Formula VII is achieved rapidly and under mild conditions. The amount of citric acid (as sodium citrate) can range from about 0.5 mg/ml up to the amount maximally soluble in the medium. Preferred amounts of citric acid range from 15 to 30 µg/ml.

The amount of compound of Formula VII having a chelating means can range from 0.001 to about 3 mg/mL, preferably about 0.017 to about 0.15 mg/mL. Finally, technetium-99m in the form of pertechnetate can be used in amounts of preferably about 1-50 mCi. The amount of mCi per mg of compound of the present invention is preferably about 30-150.

Alternative compositions of the present invention include an In-111 labeled compound of the present invention.

The present invention also includes compositions of the compounds of the present invention which are useful for in vivo imaging of thrombi in a mammal, comprised of a compound represented by Formula VII complexed to a paramagnetic atom.

Preferred paramagnetic atoms are divalent or trivalent ions of elements with an atomic number of 21 to 29, 42, 44 and 58 to 70. Suitable ions include chromium(III), manganese(II), iron(III), iron(II), cobalt(II), nickel(II), copper(II), praseodymium(III), neodymium(III), samarium(III) and ytterbium (III). Because of their very strong magnetic moments, gadolinium(III), terbium(III), dysoprosium(III), holmium(III), and erbium(III) are preferred. Especially preferred for the paramagnetic atom is gadolinium(III).

The compositions of the present invention may be prepared by combining a compound of Formula VII with a paramagnetic atom. For example, the metal oxide or a metal salt (for example, nitrate, chloride or sulfate) of a suitable paramagnetic atom is dissolved or suspended in a medium comprised of water and an alcohol, such as methyl, ethyl or isopropyl alcohol. This mixture is added to a solution of an equimolar amount of the compound of Formula VII in a similar aqueous medium and stirred. The reaction mixture may be heated moderately until the reaction is completed. Insoluble compositions formed may be isolated by filtering, while soluble compositions may be isolated by evaporation of the solvent. If acid groups on the chelating means are still present in the composition of the present invention, inorganic or organic bases, and even amino acids, may be added to convert the acidic complex into a neutral complex to facilitate isolation or purification of homogenous composition. Organic bases or basic amino acids may be used as neutralizing agents, as well as inorganic bases such as hydroxides, carbonates or bicarbonates of sodium, potassium or lithium.

The present invention also include diagnostic compositions which are useful for in vivo imaging of thrombi in a mammal, comprising a pharmaceutically acceptable carrier and a diagnostically effective amount of a radiolabeled compound of Formula VII. Compositions such as those described above may be conveniently used in these diagnostic compositions.

The "diagnostically effective amount" of the composition required as a dose will depend on the route of administration, the type of mammal being treated, and the physical characteristics of the specific mammal under consideration. These factors and their relationship to determining this dose are well known to skilled practitioners in the medial diagnostic arts. Also, the diagnostically effective amount and method of administration can be tailored to achieve optimal efficacy but will depend on such factors as weight, diet, concurrent medication and other factors which those skilled in the medical arts will recognize. In any regard, the dose for imaging should be sufficient for detecting the presence of the imaging agent at the site of a thrombus in question. Typically, radiologic imaging will require that the dose provided by the pharmaceutical composition position of the present invention be about 5 to 20 µCi, preferably about 10 µCi. Magnetic resonance imaging will require that the dose provided be about 0.001 to 5 mmole/kg, preferably about 0.005 to 0.5 mmole/kg of a compound of Formula VII complexed with paramagnetic atom. In either case, it is known in the art that the actual dose will depend on the location of the thrombus.

"Pharmaceutically acceptable carriers" for in vivo use are well known in the pharmaceutical art, and are described, for example, in *Remington's Pharmaceutical Sciences*, Mack Publishing Co. (A. R. Gennaro edit. 1985).

The present invention also encompasses diagnostic compositions prepared for storage or administration. These would additionally contain preservatives, stabilizers and dyes. For example, sodium benzoate, sorbic acid and esters of p-hydroxybenzoic acid may be added as preservatives. Id. At 1449. In addition, antioxidants and suspending agents may be used.

The in vivo imaging methods of the present invention also offer several advantages over previous imaging techniques for the detection or monitoring of the presence, size, regression or increase of a thrombus. In particular, the present invention provides compounds, compositions and diagnostic compositions have been designed to bind extremely tightly to the thrombin associated with a thrombus and thereby reduce "background" due to circulating radioactivity or paramagnetism arising from unbound imaging agent. Furthermore, in vivo imaging by intracoronary injection of the compounds, compositions or diagnostic compositions of the present invention, is expected to be almost instantaneous since these imaging agents would saturate the thrombin bound to the thrombus immediately.

Accordingly, the present invention also includes methods for in vivo imaging of a thrombus in a mammal, comprising the steps of: (1) administering to a mammal a diagnostically acceptable amount of a compound, composition, or diagnostic composition of the present invention and (2) detecting a thrombus in a blood vessel.

In employing the compounds, compositions or diagnostic compositions in vivo by this method, "administering" is accomplished parenterally, in either a systemic or local targeted manner. Systemic administration is accomplished by injecting the compounds, compositions by diagnostic compositions of the present invention into a convenient and accessible vein or artery. This includes but is not limited to administration by the ankecubutal vein. Local targeted administration is accomplished by injecting the compounds, compositions or diagnostic compositions of the present invention proximal in flow to a vein or artery suspected to contain thrombi distal to the injection site. This includes but is not limited to direct injection into the coronary arterial vasculature to image coronary thrombi, into the carotid artery to image thrombi in the cerebral vasculature, or into a pedal vein to image deep vein thrombosis of the leg.

Also, the manner of delivery of a composition of the present invention to the site of a thrombus is considered within the scope of the term "administering". For example, a compound represented by Formula VII having a chelating means attached thereto may be injected into the mammal, followed at a later time by the radioactive atom thereby forming in vivo at the site of the thrombus the composition comprising the compound of formula complexed to radioactive atom. Alternatively, a composition comprising the compound of formula complexed to radioactive atom may be injected into the mammal.

The detecting of a thrombus by imaging is made possible by the presence of radioactive or paramagnetic atoms localized at such thrombus.

The radioactive atoms associated with the compositions and diagnostic compositions of the present invention are preferably imaged using a radiation detection means capable of detecting gamma radiation, such as a gamma camera or the like. Typically, radiation imaging cameras employ a conversion medium (wherein the high energy gamma ray is absorbed, displacing an electron which emits a photon upon its return to the orbital state), photoelectric detectors arranged in a spatial detection chamber (to determine the position of the emitted photons), and circuitry to analyze the photons detected in the chamber and produce an image.

The paramagnetic atoms associated with the compositions and diagnostic compositions of the present invention are detected in magnetic resonance imaging (MRI) systems. In such systems, a strong magnetic field is used to align the nuclear spin vectors of the atoms in a patient's body. The field is disturbed by the presence of paramagnetic atoms localized at a thrombus and an image of the patient is read as the nuclei return to their equilibrium alignments.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

3-Benzylsulfonylamino-6-methyl-1-[(3-guanidinooxypropyl)aminocarbonylmethyl]-2-pyridinone trifluorocaetate

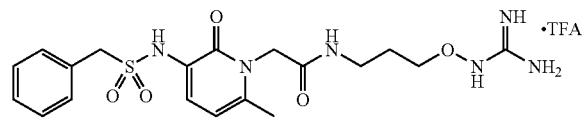

1. 3-Benzyloxycarbonylamino-6-methyl-2-pyridinone

Diphenylphosphoryl azide (11.9 mL, 55 mmol) was added to a solution of 2-hydroxy-6-methylpyridine-3-carboxylic acid (7.65 g, 50 mmol) and triethylamine (7.7 mL, 55 mmol) in dry dioxane (100 mL) and the resulting solution was heated to reflux. After 16 h more triethylamine (7.7 mL, 55 mmol) and benzyl alcohol (5.7 mL, 50 mmol) were added and the solution was refluxed for a further 24 h. The reaction mixture was concentrated in vacuo and the residue was partitioned between methylene chloride (200 mL) and brine (100 mL), acidified to pH 1 with 10% HCl. The organic layer was washed with saturated $NaHCO_3$ (2×100 mL), brine (100 mL), dried over $Na_2SO_4$ and filtered. After evaporating the solvent in vacuo, methanol (100 mL) and hexane (20 mL) were added to the residue, the solid was collected, washed with methanol (50 mL) and dried to give the title compound as a white solid (7.2 g, 56%). $^1$H-NMR (300 MHz, $CDCl_3$) δ 12.82 (s, 1H), 8.06 (d, J=7.0 Hz, 1H), 7.69 (s, 1H), 7.42 (m, 5H), 6.09 (d, J=7.5 Hz, 1H), 5.22 (s, 2H), 2.32 (s, 3H).

2. 3-Benzyloxycarbonylamino-6-methyl-1-(tert-butoxycarbonylmethyl)-2-pyridinone tert-Butyl bromoacetate (3.9 g, 20 mmol) was added to a stirred suspension of 3-benzyloxycarbonylamino-6-methyl-2-pyridinone (5.15 g, 20 mmol), as prepared in the preceding step, and $Cs_2CO_3$ (6.5 g, 20 mmol) in N,N-dimethylformamide (50 mL) and stirred at 40° C. overnight. The solid was removed by filtration and the filtrate concentrated under high vacuum. The residue was dissolved in ethyl acetate (150 mL), washed with water (2×50 mL), brine (50 mL), dried over $Na_2SO_4$ and concentrated in vacuo. After evaporating the solvent in vacuo, the residue was purified by flash column chromatography (25% ethyl acetate in hexane) to give the title compound as a white crystalline solid (4.2 g, 56%). $^1$H-NMR (300 MHz, $CDCl_3$) δ 7.95 (d, J=7.3 Hz, 1H), 7.76 (s, 1H), 7.37 (m, 5H), 6.09 (d, J=7.6 Hz, 1H), 5.19 (s, 2H), 4.75 (s, 2H), 2.32 (s, 3H), 1.47 (s, 9H).

3. 3-Amino-6-methyl-1-(tert-butoxycarbonylmethyl)-2-pyridinone

A mixture of 3-benzyloxycarbonylamino-6-methyl-1-(tert-butoxycarbonylmethyl)-2-pyridinone (4.1 g, 11 mmol), as prepared in the preceding step, and 10% Pd/C (400 mg) in ethanol (100 mL) was hydrogenated under hydrogen (balloon) for 1.5 h. The catalyst was removed by filtration through Celite and the filtrate concentrated to give the title compound as white solid (2.55 g, 97%). $^1$H-NMR (300 MHz, $CDCl_3$) δ 6.49 (d, J=7.3 Hz, 1H), 5.92 (d, J=7.3 Hz, 1H), 4.75 (s, 2H), 2.19 (s, 3H), 1.47 (s, 9H).

4. 3-Benzylsulfonylamino-6-methyl-1-(tert-butoxycarbonylmethyl)-2-pyridinone

To a solution of 3-amino-6-methyl-1-(tert-butoxycarbonylmethyl)-2-pyridinone (960 mg, 4.0 mmol), as prepared in the preceding step, and N-methylmorpholine (840 μL, 8.0 mmol) in methylene chloride (40 mL) was added α-toluenesulfonyl chloride (765 mg, 4.0 mmol) at 0° C. The reaction mixture was stirred at 0° C. for 1 h Additional methylene chloride (50 mL) was added. The resulting methylene chloride solution was washed with saturated $NaHCO_3$ (2×50 mL), 10% citric acid (3×50 mL) and brine (50 mL), and dried over $Na_2SO_4$. The solvent was concentrated to give a solid which was washed with ethyl acetate/hexane (1:2, 60 mL) to give the title compound as a white solid (1.4 g, 89%). 1H-NMR (300 MHz, CDCl$_3$) δ 7.35 (d, J=7.5 Hz, 1H), 7.31 (m, 5H), 7.20 (s, 1H), 6.02 (d, J=7.4 Hz, 1H), 4.75 (s, 2H), 4.31 (s, 2H), 2.27 (s, 3H), 1.51 (s, 9H).

5. 3-Benzylsulfonylamino-6-methyl-1-carboxymethyl-2-pyridinone

HCl gas was bubbled through a stirred suspension of 3-benzylsulfonylamino-6-methyl-1-(tert-butoxycarbonylmethyl)-2-pyridinone (1.4 g, 3.57 mmol), as prepared in the preceding step, in ethyl acetate (15 mL) at 0° C. until a solution was formed. After 2 h at room temperature, a thick suspension was formed. The mixture was degassed with nitrogen and filtered to give the title compound a white solid (1.1 g, 92%). $^1$H-NMR (300 MHz, CDCl$_3$) δ 8.67 (s, 1H), 7.34 (m, 5H), 7.12 (d, J=7.5 Hz, 1H), 6.10 (d, J=7.6 Hz, 1H), 4.78 (s, 2H), 4.51 (s, 2H), 2.26 (s, 3H).

6. 3-(Benzyloxycarbonylamino)-1-propanol

To a solution of 3-amino-1-propanol (3.75 g, 50 mmol) in methylene chloride (40 mL) was slowly added benzyl chloroformate (3.4 g, 20 mmol) in methylene chloride (10 mL) at 0° C. and the mixture was stirred at 0° C. for 3 h. Additional methylene chloride (50 mL) was added, the solution washed with 10% citric acid (3×50 mL) and brine (50 mL), and dried over Na$_2$SO$_4$. After evaporating the solvent in vacuo, the residue was purified by filtration through silica gel (1:1 ethyl acetate:hexane) to give the title compound as a white solid (4.05 g, 97%). $^1$H-NMR (300 MHz, CDCl$_3$) δ 7.34 (m, 5H), 5.17 (br s, 1H), 5.10 (s, 2H), 3.66 (t, J=5.8 Hz, 2H), 3.33 (t, J=6.1 Hz, 2H), 2.63 (br s, 1H), 1.69 (pentet, J=6.1 Hz, 2H).

7. N-[3-(Benzyloxycarbonylamino)-1-propoxy]phthalimide

To a solution of 3-(benzyloxycarbonylamino)-1-propanol (4.0 g, 19 mmol), as prepared in the preceding step, N-hydroxyphthalimide (3.26 g, 20 mmol) and triphenylphosphine (5.25 g, 20 mmol) in tetrahydrofuran (80 mL) was added diethyl azodicaroxylate (3.5 g, 20 mmol). The reaction mixture was stirred at room temperature overnight. Ethyl acetate (200 mL) was added, the solution washed with saturated NaHCO$_3$ (2×100 mL) and brine (100 mL), and dried over Na$_2$SO$_4$. After evaporating the solvent, the residue was purified by flash column chromatography (methylene chloride to 4% ethyl acetate in methylene chloride) to give the title compound as a white solid (6.85 g, 100%). $^1$H-NMR (300 MHz, CDCl$_3$) δ 7.83 (m, 2H), 7.77 (m, 2H), 7.36 (m, 5H), 5.67 (br s, 1H), 5.12 (s, 2H), 4.28 (t, J=5.8 Hz, 2H), 3.51 (q, J=6.1 Hz, 2H), 1.99 (pentet, J=6.0 Hz, 2H).

8. 3-(Benzyloxycarbonylamino)-1-propoxyamine

To a solution of N-[3-(benzyloxycarbonylamino)-1-propoxy]phthalimide (1.42 g, 4.0 mmol), as prepared in the preceding step, in ethanol (20 mL) and tetrahydrofuran (20 mL) was added 40% methylamine (2 mL, 25 mmol). The solution was stirred at room temperature for 1 h. The solvent was evaporated and the residue passed through silica gel (3:1 ethyl acetate: hexane to ethyl acetate) to give the title compound as a white solid (870 mg, 97%). $^1$H-NMR (300 MHz, CDCl$_3$) δ 7.36 (m, 5H), 5.38 (br s, 2H), 5.09 (s, 2H), 5.08 (br s, 1H), 3.73 (t, J=5.9 Hz, 2H), 3.29 (q, J=6.2 Hz, 2H), 1.79 (pentet, J=6.2 Hz, 2H).

9. [N,N'-Di(tert-butoxycarbonyl)] 3-(benzyloxycarbonylamino)-1-propoxyguanidine To a solution of 3-(benzyloxycarbonylamino)-1-propoxyamine (860 mg, 3.84 mmol), as prepared in the preceding step, in N,N-dimethylformamide (20 mL) was added [N,N'-di(tert-butoxycarbonyl)]amidinopyrazole (1.25 g, 4.0 mmol). The mixture was stirred at room temperature overnight, the solvent was evaporated under high vacuum and the residue was purified by flash column chromatography (0-5% ethyl acetate in methylene chloride) to give the title compound as a colorless oil (1.60 g, 89%). $^1$H-NMR (300 MHz, CDCl$_3$) δ 9.10 (br s, 1H), 7.74 (br s, 1H), 7.35 (m, 5H), 5.55 (br s, 1H), 5.10 (s, 2H), 4.12 (t, J=6.1 Hz, 2H), 3.32 (t, J=6.4 Hz, 2H), 1.87 (pentet, J=6.2 Hz, 2H), 1.50 (s, 9H), 1.47 (s, 9H).

10. [N,N'-Di(tert-butoxycarbonyl)] 3-amino-1-propoxyguanidine

A mixture of [N,N'-di(tert-butoxycarbonyl)] 3-(benzyloxycarbonylamino)-1-propoxyguanidine (760 mg, 1.7 mmol), as prepared in the preceding step, and 10% Pd/C (80 mg) in ethanol (20 mL) and tetrahydrofuran (20 mL) was hydrogenated under hydrogen (balloon) for 30 min. The catalyst was removed by filtration through Celite, the filtrate was concentrated in vacuo, and the residue was purified by Waters Sep-Pak (10 g, 95:5 methylene chloride:methanol saturated with ammonia) to give the title compound as a colorless oil (160 mg, 28%). $^1$H-NMR (300 MHz, CDCl$_3$) δ 4.12 (t, J=6.1 Hz, 2H), 2.85 (t, J=6.7 Hz, 2H), 1.84 (pentet, J=6.2 Hz, 2H), 1.50 (s, 9H), 1.48 (s, 9H).

11. 3-Benzylsulfonylamino-6-methyl-1-{[N,N'-di(tert-butoxycarbonyl)] [3-(guanidinooxypropyl)aminocarbonylmethyl]}-2-pyridinone To a solution of 3-benzylsulfonylamino-6-methyl-1-carboxymethyl-2-pyridinone (152 mg, 0.45 mmol), as prepared in the step 5, [N,N'-di(tert-butoxycarbonyl)] 3-amino-1-propoxyguanidine (150 mg, 0.45 mmol), as prepared in the preceding step, and diisopropylethylamine (90 μL, 0.5 mmol) in N,N-dimethylformamide (10 mL) was added Castro's reagent (BOP) (221 mg, 0.5 mmol). The mixture was stirred at room temperature overnight. Ethyl acetate (100 mL) was added, the solution washed with saturated NaHCO$_3$ (2×50 mL), 10% citric acid (2×50 mL) and brine (50 mL), and dried over Na$_2$SO$_4$. After evaporating the solvent in vacuo, the residue was purified by Waters Sep-Pak (10 g, 4:1 ethyl acetate:hexane) to give the title compound as a colorless foam (270 mg, 92%). $^1$H-NMR (300 MHz, CDCl$_3$) δ 9.02 (s, 1H), 8.70 (s, 1H), 8.58 (s, 1H), 8.27 (t, J=5.6 Hz, 1H), 7.34 (m, 5H), 7.12 (d, J=7.6 Hz, 1H), 6.08 (d, J=7.7 Hz, 1H), 4.70 (s, 2H), 4.50 (s, 2H), 3.88 (t, J=6.3 Hz, 2H), 3.18 (t, J=6.4 Hz, 2H), 2.24 (s, 3H), 1.75 (t, J=6.5 Hz, 2H), 1.39 (s, 18H).

12. 3-Benzylsulfonylamino-6-methyl-1-[(3-guanidinooxypropyl) aminocarbonylmethyl]-2-pyridinone trifluoroacetate A mixture of 3-benzylsulfonylamino-6-methyl-1-{[N,N'-di(tert-butoxycarbonyl)] [3-(guanidinooxypropyl)aminocarbonylmethyl]}-2-pyridinone (130 mg, 0.2 mmol), as prepared in the preceding step, and trifluoroacetic acid (2 mL) in methylene chloride (5 mL) was stirred at room temperature for 1 h. After evaporating the solvent in vacuo, the residue was purified by Waters Sep-Pak (10 g, 10% methanol in methylene chloride) to give the title compound as a colorless foam (55 mg, 61%). $^1$H-NMR (300 MHz, DMSO-$d_6$) δ 8.57 (s, 1H), 8.35 (t, J=5.7 Hz, 1H), 7.62 (br s, 4H), 7.34 (m, 5H), 7.12 (d, J=7.5 Hz, 1H), 6.09 (d, J=7.7 Hz, 1H), 4.70 (s, 2H), 4.52 (s, 2H), 3.81 (t, J=6.4 Hz, 2H), 3.20 (q, J=6.4 Hz, 2H), 2.25 (s, 3H), 1.77 (pentet, J=6.5 Hz, 2H). Mass spectrum (MALDI-TOF, α-cyano-4-hydroxycinnamic acid matrix) calcd. for $C_{19}H_{26}N_6O_5S$: 451.2 (M+H), 473.2 (M+Na); Found: 451.5, 473.5.

EXAMPLE 2

3-Benzylsulfonylamino-6-methyl-1-[(2-guanidinooxyethyl)aminocarbonylmethyl]-2-pyridinone trifluoroacetate

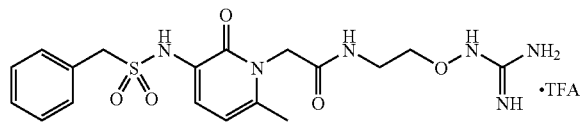

1.
N-[2-(Benzyloxycarbonylamino)ethoxy]phthalimide

To a solution of benzyl N-(2-hydroxyethyl)carbamate (5.9 g, 30 mmol), N-hydroxyphthalimide (4.9 g, 30 mmol), and triphenylphosphine (7.9 g, 30 mmol) in tetrahydrofuran (100 mL) was added diethyl azodicarboxylate (5.2 g, 30 mmol). The reaction mixture was stirred at room temperature overnight. Ethyl acetate (200 mL) was added, the solution washed with saturated NaHCO$_3$ (2×100 mL) and brine (100 mL), and dried over Na$_2$SO$_4$. After evaporating the solvent, the residue was purified by flash column chromatography (methylene chloride to 4% ethyl acetate in methylene chloride) to give the title compound as a white solid (9.3 g, 91%). $^1$H-NMR (300 MHz, CDCl$_3$) δ 7.84 (m, 2H), 7.78 (m, 2H), 7.37 (m, 5H), 5.97 (br s, 1H), 5.14 (s, 2H), 4.27 (t, J=4.9 Hz, 2H), 3.51 (q, J=5.2 Hz, 2H).

2. 2-(Benzyloxycarbonylamino)ethoxyamine

To a solution of N-[2-(benzyloxycarbonylamino)ethoxy] phthalimide (1.36 g, 4.0 mmol), as prepared in the preceding step, in ethanol (20 mL) and tetrahydrofuran (20 mL) was added 40% methylamine (2 mL, 25 mmol). The reaction mixture was stirred at room temperature for 1 h. After evaporating the solvent, the residue was passed through silica gel (3:1 ethyl acetate:hexane to ethyl acetate) to give the title compound as a white solid (800 mg, 95%). $^1$H-NMR (300 MHz, CDCl$_3$) δ 7.36 (m, 5H), 5.47 (br s, 2H), 5.21 (br s, 1H), 5.10 (s, 2H), 3.72 (t, J=5.0 Hz, 2H), 3.44 (q, J=5.0 Hz, 2H).

3. [N,N'-Di(tert-butoxycarbonyl)] 2-(benzyloxycarbonylamino) ethoxyguanidine

To a solution of 2-(benzyloxycarbonylamino)ethoxyamine (780 mg, 3.7 mmol), as prepared in the preceding step, in N,N-dimethylformamide (20 mL) was added [N,N'-di(tert-butoxycarbonyl)] amidinopyrazole (1.25 g, 4.0 mmol). The mixture was stirred at room temperature overnight, the solvent was evaporated under high vacuum. The residue was purified by flash column chromatography (0-5% ethyl acetate in methylene chloride) to give the title compound as a color-less oil (1.55 g, 93%). $^1$H-NMR (300 MHz, CDCl$_3$) δ 9.08 (s, 1H), 7.67 (s, 1H), 7.33 (m, 5H), 6.21 (br s, 1H), 5.21 (br s, 1H), 5.11 (s, 2H), 4.12 (t, J=4.8 Hz, 2H), 3.54 (q, J=4.9 Hz, 2H), 1.49 (s, 9H), 1.46 (s, 9H).

4. [N,N'-Di(tert-butoxycarbonyl)] 2-aminoethoxyguanidine

A mixture of [N,N'-di(tert-butoxycarbonyl)] 2-(benzyloxycarbonylamino)-ethoxyguanidine (730 mg, 1.5 mmol), as prepared in the preceding step, and 10% Pd/C (70 mg) in ethanol (20 mL) and tetrahydrofuran (20 mL) was hydrogenated under hydrogen (balloon) for 30 min. The catalyst was removed by filtration through Celite and the filtrate was concentrated in vacuo. The residue was purified by Waters Sep-Pak (10 g, 95:5 methylene chloride:methanol saturated with ammonia) to give the title compound as a colorless oil (290 mg, 61%). $^1$H-NMR (300 MHz, CDCl$_3$) δ 9.08 (br s, 1H), 4.08 (t, J=5.2 Hz, 2H), 2.99 (q, J=5.1 Hz, 2H), 1.50 (s, 9H), 1.48 (s, 9H).

5. 3-Benzylsulfonylamino-6-methyl-1-{[N,N'-di(tert-butoxycarbonyl)] [2-(guanidinooxyethyl)aminocarbonylmethyl]}-2-pyridinone To a solution of 3-benzylsulfonylamino-6-methyl-1-carboxymethyl-2-pyridinone (152 mg, 0.45 mmol), as prepared in the step 5 of Example 1, [N,N'-di(tert-butoxycarbonyl)] 2-aminoethoxyguanidine (143 mg, 0.45 mmol), as prepared in the preceding step, diisopropylethylamine (90 μL, 0.5 mmol) in N,N-dimethylformamide (10 mL) was added Castro's reagent (BOP) (221 mg, 0.5 mmol). The mixture was stirred at room temperature overnight. Ethyl acetate (100 mL) was added, the solution was washed with saturated NaHCO$_3$ (2×50 mL), 10% citric acid (2×50 mL) and brine (50 mL), and dried over Na$_2$SO$_4$. After evaporating the solvent in vacuo, the residue was purified by Waters Sep-Pak (10 g, 4:1 ethyl acetate:hexane) to give the title compound as a colorless foam (270 mg, 94%). $^1$H-NMR (300 MHz, CDCl$_3$) δ 9.22 (s, 1H), 8.41 (t, J=5.0 Hz, 1H), 8.02 (s, 1H), 7.62 (s, 1H), 7.34 (s, 1H), 7.29 (m, 5H), 5.99 (d, J=7.7 Hz, 1H), 4.89 (s, 2H), 4.31 (s, 2H), 4.13 (t, J=5.0 Hz, 2H), 3.62 (q, J=5.1 Hz, 2H), 2.30 (s, 3H), 1.52 (s, 9H), 1.48 (s, 9H).

6. 3-Benzylsulfonylamino-6-methyl-1-[(2-guanidinooxyethyl) aminocarbonylmethyl]-2-pyridinone trifluoroacetate A mixture of 3-benzylsulfonylamino-6-methyl-1-{[N,N'-di(tert-butoxycarbonyl)] [2-(guanidinooxyethyl)aminocarbonylmethyl]}-2-pyridinone (255 mg, 0.4 mmol), as prepared in the preceding step, and trifluoroacetic acid (4 mL) in methylene chloride (8 mL) was stirred at room temperature for 1 h. After evaporating the solvent in vacuo, the residue was purified by Waters Sep-Pak (10 g, 10% methanol in methylene chloride) to give the title compound as a colorless foam (160 mg, 92%). $^1$H-NMR (300 MHz, DMSO-$d_6$) δ 8.58 (s, 1H), 8.49 (t, J=5.5 Hz, 1H), 7.73 (br s, 4H), 7.35 (m, 5H), 7.13 (d, J=7.6 Hz, 1H), 6.11 (d, J=7.7 Hz, 1H), 4.74 (s, 2H), 4.52 (s, 2H), 3.84 (t, J=5.3 Hz, 2H), 3.40 (m, 2H), 2.26 (s, 3H). Mass spectrum (MALDI-TOF, α-cyano-4-hydroxycinnamic acid matrix) calcd. for $C_{18}H_{24}N_6O_5S$: 437.2 (M+H), 459.1 (M+Na); Found: 437.3, 459.2.

EXAMPLE 3

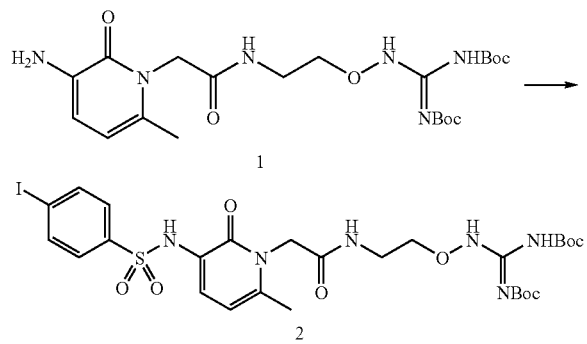

c. [I-125]p-Iodobenzene sulfonyl chloride (A. S. Keston et al., *J. Amer. Chem. Soc.* 68:1390 (1946)) can be substituted in step a for the cold-iodo compound to form [I-125]3.

EXAMPLE 4

3-Benzylsulfonylamino-1-[(2-guanidinooxyethyl)aminocarbonylmethyl]-2-pyridinone trifluoroacetate

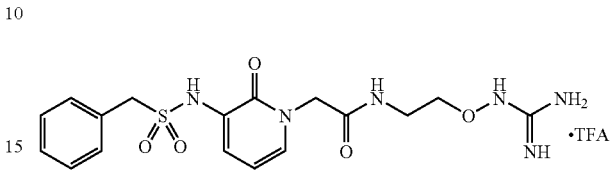

a. A solution of the amine, 1 (0.025 g, 0.052 mmol) in dichloromethane (2 mL) was treated with diethylaminoethyl polystyrene resin (Fluka, 0.033 g, 0.098 mmol) and 4-iodobenzenesulfonyl chloride (0.03 g, 0.1 mmol). The mixture was shaken at ambient temperature for five hours before aminomethyl polystyrene resin. (Adv. Chem. Tech., 0.1 g, 0.2 mmol) was added as a scavenger of excess sulfonyl chloride. Additional dichloromethane (2 mL) was added and the mixture was shaken overnight. The reaction mixture, including the resins, was poured onto a silica gel column (5 g SepPak) and eluted with a gradient of 10 to 50% ethyl acetate in dichloromethane. The appropriate fractions were collected and evaporated to dryness on a Savant. Mass spectrum (MALDI-TOF, α-cyano-4-hydroxycinnamic acid matrix) calcd. for $C_{21}H_{37}N_6O_9SI$—2 t-Boc: 549.1. Found: 549.3.

1. 3-Benzylsulfonylamino-1-(tert-butoxycarbonylmethyl)-2-pyridinone

To a solution of 3-amino-1-(tert-butoxycarbonylmethyl)-2-pyridinone (1.12 g, 5.0 mmol), and N-methylmorpholine (1.5 mL, 10.0 mmol) in methylene chloride (40 mL) was added α-toluenesulfonyl chloride (950 mg, 5.0 mmol) at 0° C. The reaction mixture was stirred at 0° C. for 1 h. Additional methylene chloride (50 mL) was added. The resulting solution was washed with saturated $NaHCO_3$ (2×50 mL), 10% citric acid (3×50 mL) and brine (50 mL), and dried over $Na_2SO_4$ and filtered and the filtrate was concentrated to give a solid which was washed with ethyl acetate/hexane (1:2, 60 mL) to give the title compound as a white solid (1.8 g, 96%). $^1$H-NMR (300 MHz, $CDCl_3$) δ 7.42 (br s, 1H), 7.36 (d, J=7.3

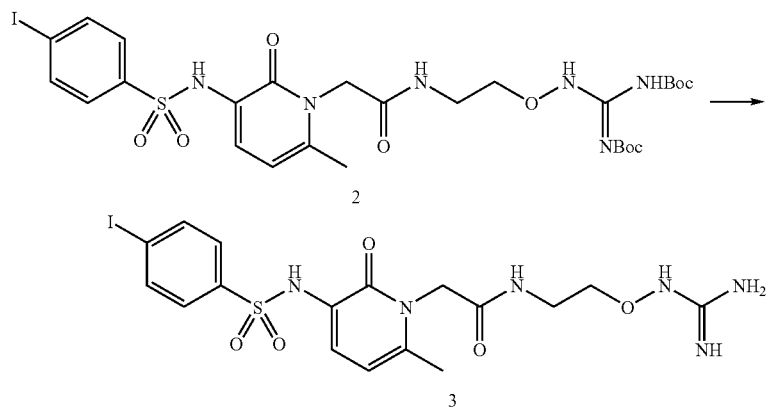

b. A solution of the sulfonamide, 2 in dichloromethane (2 mL) was treated with trifluoroacetic acid (1 mL) at ambient temperature and shaken for 4 h. The dichloromethane was removed on a Savant and the residue was purified on a silica gel column (5 g SepPak) by elution with 5% methanol in dichloromethane. The appropriate fractions were combined and evaporated to dryness to give 19.6 mg (69% yield over 2 steps) of 3 as a gum. $^1$H-NMR (300 Mhz, $CDCl_3$) δ 10.95 (s, 1H), 9.48 (s, 1H), 8.42 (t, 2H, J=5.6 Hz), 7.90 (d, 2H, J=8.6 Hz), 7.72 (s, 4H), 7.56 (d, 2H, J=8.6 Hz), 7.26 (d, 1H, J=7.5 Hz), 6.10 (d, 1H, J=7.7 Hz), 4.60 (s, 2H), 3.96 (s, 2H), 3.80 (t, 2H, J=5.3 Hz), 2.20 (s, 3H). Mass spectrum (LCMS, ESI) calcd. for $C_{17}H_{21}N_6O_5SI$: 549.1. Found: 549.0.

Hz, 1H), 7.31 (m, 5H), 6.92 (d, J=7.0 Hz, 1H), 6.14 (t, J=7.2 Hz, 1H), 4.58 (s, 2H), 4.34 (s, 2H), 1.51 (s, 9H).

2. 3-Benzylsulfonylamino-1-carboxymethyl-2-pyridinone

HCl gas was bubbled through a stirred suspension of 3-benzylsulfonylamino-1-(tert-butoxycarbonylmethyl)-2-pyridinone (1.7 g, 4.5 mmol), as prepared in the preceding step, in ethyl acetate (15 mL) at 0° C. until a solution was formed. After 2 h at room temperature, a thick suspension was formed. The mixture was degassed with nitrogen and filtered to give the title compound a white solid (1.4 g, 97%). $^1$H-NMR (300 MHz, $CDCl_3$) δ 8.76 (s, 1H), 7.45 (dd, J=7.0, 1.8 Hz, 1H), 7.32 (m, 5H), 7.19 (dd, J=7.2, 1.8 Hz, 1H), 6.16 (t, J=7.1 Hz, 1H), 4.69 (s, 2H), 4.56 (s, 2H).

3. 3-Benzylsulfonylamino-1-{[N,N'-di(tert-butoxycarbonyl)] [2-(guanidinooxyethyl)aminocarbonylmethyl]}-2-pyridinone To a solution of 3-benzylsulfonylamino-1-carboxymethyl-2-pyridinone (129 mg, 0.4 mmol), as prepared in the preceding step, [N,N'-di(tert-butoxycarbonyl)] 2-aminoethoxyguanidine (143 mg, 0.45 mmol), as prepared in step 4 of Example 2, diisopropylethylamine (90 μL, 0.5 mmol) in N,N-dimethylformamide (10 mL) was added Castro's reagent (BOP) (221 mg, 0.5 mmol). The mixture was stirred at room temperature overnight. Ethyl acetate (100 mL) was added, the solution was washed with saturated NaHCO$_3$ (2×50 mL), 10% citric acid (2×50 mL) and brine (50 mL), and dried over Na$_2$SO$_4$. After evaporating the solvent in vacuo, the residue was purified by Waters Sep-Pak (10 g, 4:1 ethyl acetate:hexane) to give the title compound as a colorless foam (170 mg, 68%). $^1$H-NMR (300 MHz, CDCl$_3$) δ 9.22 (s, 1H), 8.49 (br s, 1H), 7.44 (s, 1H), 7.34 (dd, J=7.3, 1.7 Hz, 1H), 7.29 (m, 5H), 7.02 (dd, 3=7.0, 1.7 Hz, 1H), 6.12 (t, J=7.1 Hz, 1H), 4.73 (s, 2H), 4.34 (s, 2H), 4.15 (m, 2H), 3.65 (m, 2H), 1.52 (s, 9H), 1.49 (s, 9H).

4. 3-Benzylsulfonylamino-1-[(2-guanidinooxyethyl) aminocarbonylmethyl]-2-pyridinone trifluoroacetate A mixture of 3-benzylsulfonylamino-1-{[N,N'-di(tert-butoxycarbonyl)] [(2-guanidinooxyethyl)aminocarbonylmethyl]}-2-pyridinone (155 mg, 0.25 mmol), as prepared in the preceding step, and trifluoroacetic acid (2 mL) in methylene chloride (3 mL) was stirred at room temperature for 2 h. After evaporation of the solvent in vacuo, the residue was purified by Waters Sep-Pak (10 g, 10% methanol in methylene chloride) to give the title compound as a colorless foam (160 mg, 92%). $^1$H-NMR (300 MHz, DMSO c$_6$) δ 11.00 (s, 1H), 8.66 (s, 1H), 8.45 (t, J=5.3 Hz, 1H), 7.72 (br s, 4H), 7.40 (d, J=6.9 Hz, 1H), 7.33 (m, 5H), 7.19 (d, J=7.0 Hz, 1H), 6.19 (d, J=7.0 Hz, 1H), 4.62 (s, 2H), 4.55 (s, 2H), 3.83 (t, J=5.1 Hz, 2H), 3.39 (m, 2H). Mass spectrum (MALDI-TOF, α-cyano-4-hydroxycinnamic acid matrix) calcd. for C$_{17}$H$_{22}$N$_6$O$_5$S: 423.1 (M+H), 445.1 (M+Na); Found: 423.3, 445.0.

EXAMPLE 5

3-(3-Methylphenylsulfonyl)amino-6-methyl-1-[(2-guanidinooxyethyl)aminocarbonylmethyl]-2-pyridinone trifluoroacetate

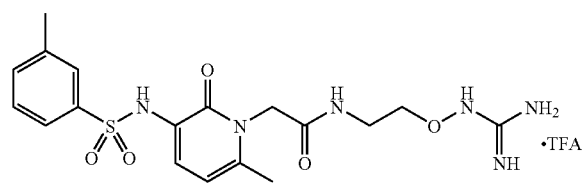

1. 3-(3-Methylphenylsulfonyl)amino-6-methyl-1-(tert-butoxycarbonylmethyl)-2-pyridinone To a solution of 3-amino-6-methyl-1-(tert-butoxycarbonylmethyl)-2-pyridinone (1.42 g, 5.88 mmol), as prepared in step 3 of Example 1, and N-methylmorpholine (1.29 mL. 11.76 mmol) in methylene chloride (40 mL) was added 3-methylbenzenesulfonyl chloride (1.12 g, 5.88 mmol) at 0° C. The reaction mixture was stirred at room temperature overnight. Additional methylene chloride (60 mL) was added. The resulting methylene chloride solution was washed with saturated NaHCO$_3$ (2×50 mL), 10% citric acid (3×50 mL) and brine (50 mL), and dried over Na$_2$SO$_4$. After evaporating the solvent, the residue was purified by flash column chromatography (5 to 10% ethyl acetate in methylene chloride) to give the title compound as a white solid (2.1 g, 91%). $^1$H-NMR (300 z, CDCl$_3$) δ 7.63 (m, 2H), 7.55 (br s, 1H), 7.42 (d, 1H, J=8 Hz), 7.32 (m, 2H), 6.01 (d, 1H, J=8 Hz), 4.64 (s, 2H), 2.37 (s, 3H), 2.20 (s, 3H), 1.43 (s, 9H).

2. 3-(3-Methylphenylsulfonyl)amino-6-methyl-1-carboxymethyl-2-pyridinone

HCl gas was bubbled through a stirred suspension of 3-(3-methylphenylsulfonyl)amino-6-methyl-1-(tert-butoxycarbonylmethyl)-2-pyridinone (2.0 g, 5.09 mmol), as prepared in the preceding step, in ethyl acetate (50 mL) at 0° C. until a solution was formed. After warming to room temperature over 2 h, a thick suspension was formed. The mixture was degassed with nitrogen and filtered to give the title compound as a white solid (1.36 g, 80%). $^1$H-NMR (300 MHz, DMSO-d$_6$) δ 9.38 (s, 1H), 7.62 (m, 2H), 7.41 (m, 2H), 7.25 (d, 1H, J=8 Hz), 6.09 (d, 1H, J-8 Hz), 4.67 (s, 2H), 2.35 (s, 3H), 2.20 (s, 3H).

3. 3-(3-Methylphenylsulfonyl)amino-6-methyl-1-{[N,N'-di(tert-butoxycarbonyl)] [2-(guanidinooxyethyl)aminocarbonylmethyl]}-2-pyridinone To a solution of 3-(3-methylphenylsulfonyl)amino-6-methyl-1-carboxymethyl-2-pyridinone (1.26 g, 3.75 mmol), as prepared in the preceding step, [N,N'-di(tert-butoxycarbonyl)] 2-amino-1-ethoxyguanidine hydrochloride (1.33 g, 3.75 mmol) as prepared in step 4 of Example 2, and diisopropylethylamine (1.29 g, 10.0 mmol) in N,N-dimethylformamide (30 mL) was added Castro's reagent (BOP) (2.0 g, 4.47 mmol). The mixture was stirred at room temperature overnight. Ethyl acetate (150 mL) was added, the solution was washed with saturated NaHCO$_3$ (2×50 mL), 10% citric acid (2×50 mL) and brine (50 mL), and dried over Na$_2$SO$_4$. After evaporating the solvent in vacuo, the residue was purified twice by column chromatography (1:1 ethyl acetate:hexane; then 2% methanol in methylene chloride) to give the title compound as a white solid (2.25 g, 92%). $^1$H-NMR (300 MHz, CDCl$_3$) δ 9.17 (s, 1H), 8.34 (t, J=5.1 Hz, 1H), 7.66 (m, 4H), 7.48 (d, J=7.6 Hz, 1H), 7.32 (m, 2H), 6.00 (d, J=7.7 Hz, 1H), 4.80 (s, 2H), 4.10 (t, J=5.3 Hz, 2H), 3.59 (q, J=5.4 Hz, 2H), 2.38 (s, 3H), 2.25 (s, 3H), 1.55 (s, 9H), 1.45 (s, 9H).

4. 3-(3-Methylphenylsulfonyl)amino-6-methyl-1-[(3-guanidinooxyethyl) aminocarbonylmethyl]-2-pyridinone trifluorocaetate A mixture of 3-(3-methylphenylsulfonyl)amino-6-methyl-1-{[N,N'-di(tert-butoxycarbonyl)] [3-(guanidinooxypropyl) aminocarbonylmethyl]}-2-pyridinone (2.24 g, 3.44 mmol), as prepared in the preceding step, and trifluoroacetic acid (10 mL) in methylene chloride (20 mL) was stirred at room temperature for 4 h. After evaporating the solvent in vacuo, the residue was purified by column chromatography (10% methanol in methylene chloride) to give the title compound as a white solid (1.59 g, 82%). $^1$H-NMR (300 MHz, CD$_3$OD) δ

7.61 (m, 2H), 7.47 (d, 1H, J=7.6 Hz), 7.38 (m, 2H), 6.20 (dd, 1H, J=7.7 Hz, 0.7 Hz), 4.70 (s, 2H), 3.93 (t, 2H, J=5.2 Hz), 3.48 (t, 2H, J=5.2 Hz), 2.37 (s, 3H), 2.29 (s, 3H). Mass spectrum (LCMS, ESI) calcd. for $C_{18}H_{24}SN_6O_5$: 437.5 (M+H); found: 437.2.

5. 3-(3-Methylphenylsulfonyl)amino-6-methyl-1-[(3-guanidinooxyethyl)aminocarbonylmethyl]-2-pyridinone hydrochloride 3-(3-Methylphenylsulfonyl)amino-6-methyl-1-[(3-guanidinooxyethyl) aminocarbonylmethyl]-2-pyridinone trifluoroacetate (2.75 g, 5.0 mmol), as prepared in the preceding step, was treated with water (10 mL) and brine (80 mL). The pH of the mixture was adjusted to 1 with 20% hydrochloride acid, the resulting mixture was stirred until the product crystallized. The precipitate was collected by filtration, washed with ice cold water, and oven dried in vacuo at 45° C. for two days to afford the title compound as an off-white solid (2.25 g, 95%). mp: 177-179° C. $^1$H-NMR (300 MHz, DMSO-$d_6$) δ 11.1 (s, 1H), 9.3 (s, 1H), 8.6 (t, J=7.5 Hz, 1H), 7.75 (br s, 4H), 7.42 (m, 4H), 7.25 (d, J=7.6 Hz, 1H), 6.10 (d, J=7.7 Hz, 1H), 4.65 (s, 2H), 3.80 (t, J=5.2 Hz, 2H), 3.40 (q, J=5.2 Hz, 2H), 2.35 (s, 3H), 2.24 (s, 3H). Mass spectrum (LCMS, ESI) calcd. for $C_{18}H_{24}SN_6O_5$: 437.5 (M+H); found: 437.2.

EXAMPLE 6

3-(Benzyloxycarbonyl)amino-6-methyl-1-[(2-guanidinooxyethyl)aminocarbonylmethyl]-2-pyridinone trifluoroacetate

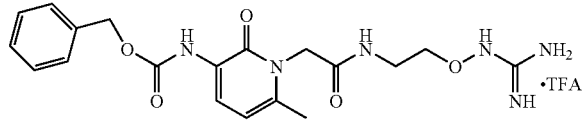

The title compound was prepared form 3-benzyloxycarbonylamino-6-methyl-1-(tert-butoxycarbonylmethyl)-2-pyridinone, as prepared in step 2 of Example 1, using the procedures in step 5 of Example 1 and steps 5 & 6 of Example 2. $^1$H-NMR (300 MHz, DMSO-$d_6$) δ 11.03 (s, 1H), 8.47 (t, J=5.4 Hz, 1H), 8.30 (s, 1H), 7.76 (br s, 4H), 7.73 (d, J=7.5 Hz, 1H), 7.40 (m, 5H), 6.18 (d, J=7.7 Hz, 1H), 5.15 (s, 2H), 4.73 (s, 2H), 3.82 (t, J=5.3 Hz, 2H), 3.38 (m, 2H), 2.24 (s, 3H). Mass spectrum (MALDI-TOF, α-cyano-4-hydroxycinnamic acid matrix) calcd. for $C_{19}H_{24}N_6O_5$: 417.2 (M+H), 439.2 (M+Na), 455.1 (M+K); Found: 417.3, 439.4, 455.4.

EXAMPLE 7

3-(Benzylsulfonyl)amino-6-methyl-1-[(1-(1-guanidinooxymethyl) cyclopropyl)aminocarbonylmethyl]-2-pyridinone trifluoroacetate

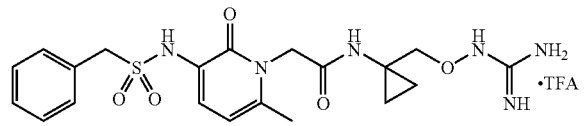

1.
1-(Benzyloxycarbonylamino)cyclopropanemethanol

To a solution of 1-(benzyloxycarbonylamino)cyclopropanecarboxylic acid (500 mg, 2.1 mmol) in tetrahydrofuran (5 mL) at 0° C. was added $B_2H_6$. THF (1M, 2.1 mL, 2.1 mmol). The mixture was stirred at ambient temperature overnight, treated with $K_2CO_3$ (1.0 g in 5 mL $H_2O$) and extracted with methylene chloride (3×10 mL). The organic layer was washed with brine (10 mL) and dried over $Na_2SO_4$. After evaporating the solvent, the residue was by chromatography (1:1 ethyl acetate:hexane) to give the title compound as a white solid (200 mg, 43%). $^1$H-NMR (300 MHz, CDCl$_3$) δ 7.35 (m, 5H), 5.30 (br s, 1H), 5.10 (s, 2H), 3.61 (s, 2H), 3.02 (br s, 1H), 0.86 (s, 4H).

2. N-[1-(Benzyloxycarbonylamino)cyclopropanemethoxy]phthalimide

The title compound was prepared from 1-(benzyloxycarbonylamino) cyclopropanemethanol (200 mg, 0.9 mmol), as prepared in the preceding step, using the procedure in step 1 of Example 2, as a white solid (295 mg, 90%). $^1$H-NMR (300 MHz, CDCl$_3$) δ 7.83 (m, 2H), 7.79 (m, 2H), 7.37 (m, 5H), 6.23 (br s, 1H), 5.13 (s, 2H), 4.18 (s, 2H), 0.93 (m, 2H), 0.72 (m, 2H).

3. [1-(Benzyloxycarbonylamino)cyclopropanemethoxy]amine

The title compound was prepared from N-[1-(benzyloxycarbonylamino) cyclopropanemethoxy]phthalimide (290 mg, 0.8 mmol), as prepared in the preceding step, using the procedure in step 2 of Example 2, as a colorless oil (180 mg, 95%). $^1$H-NMR (300 MHz, CDCl$_3$) δ 7.35 (m, 5H), 5.60 (br s, 2H), 5.23 (br s, 1H), 5.09 (s, 2H), 3.64 (s, 2H), 0.89 (m, 4H).

4. [N,N'-Di(tert-butoxycarbonyl)] [1-(benzyloxycarbonylamino) cyclopropanemethoxy]guanidine The title compound was prepared from [1-(benzyloxycarbonylamino) cyclopropanemethoxy]amine (180 mg, 0.76 mmol), as prepared in the preceding step, and (N,N'-di-tert-butoxycarbonyl)amidinopyrazole (280 mg, 0.9 mmol) using the procedure in step 3 of Example 2, as a colorless oil (330 mg, 91%). $^1$H-NMR (300 MHz, CDCl$_3$) δ 9.10 (br s, 1H), 8.02 (br s, 1H), 7.35 (m, 5H), 5.74 (br s, 1H), 5.09 (s, 2H), 4.03 (s, 2H), 1.49 (s, 9H), 1.47 (s, 9H), 0.91 (m, 4H).

5. [N,N'-Di(tert-butoxycarbonyl)] (1-aminocyclopropanemethoxy) guanidine

The title compound was prepared from [N,N'-di(tert-butoxycarbonyl)] [1-(benzyloxycarbonylamino)cyclopropapemethoxy]guanidine (330 mg, 0.69 mmol), as prepared in the preceding step, using the procedure in step 4 of Example 2, as a colorless oil (200 mg, 84%). $^1$H-NMR (300 MHz, CDCl$_3$) δ 9.09 (br s, 1H), 3.96 (s, 2H), 1.52 (s, 9H), 1.48 (s, 9H), 0.67 (m, 2H), 0.60 (m, 2H).

6. 3-Benzylsulfonylamino-6-methyl-1-{[N,N'-di(tert-butoxycarbonyl)] [1-(1-(guanidinooxymethyl)cyclopropylamino)carbonylmethyl]}-2-pyridinone The title compound was prepared from [N,N'-di(tert-butoxycarbonyl)] (1-aminocyclopropanemethoxy)guanidine (100 mg, 0.3 mmol), as prepared in the preceding step, and 3-benzylsulfonylamino-6-methyl-1-carboxymethyl-2-pyridinone (100 mg, 0.3 mmol), as prepared in the step 5 of Example 1, using the procedure in step 5 of Example 2, as a colorless foam (120 mg, 60%). $^1$H-NMR (300 MHz, CDCl$_3$) δ 9.08 (br s, 1H), 7.74 (s, 1H), 7.72 (s, 1H), 7.31 (d, J=7.5 Hz, 1H), 7.26 (m, 5H), 6.00 (d, J=7.7 Hz, 1H), 4.79 (s, 2H), 4.30 (s, 2H), 3.97 (s, 2H), 2.31 (s, 3H), 1.51 (s, 9H), 1.48 (s, 9H), 1.04 (m, 2H), 0.87 (m, 2H).

7. 3-(Benzylsulfonyl)amino-6-methyl-1-[(1-(1-guanidinooxymethyl) cyclopropyl)aminocarbonylmethyl]-2-pyridinone trifluoroacetate The title compound was prepared form 3-benzylsulfonylamino-6-methyl-1-{[N,N'-di(tert-butoxycarbonyl)] [1-(1-(guanidinooxymethyl)cycloamino)carbonylmethyl]}-2-pyridinone (110 mg, 0.166 mmol), as prepared in the preceding step, using the procedure in step 6 of Example 2, as a white solid (85 mg, 89%). $^1$H-NMR (300 MHz, DMSO-d$_6$) δ 1.88 (br s, 1H), 8.78 (s, 1H), 8.60 (s, 1H), 7.73 (br s, 4H), 7.33 (m, 5H), 7.13 (d, J=7.5 Hz, 1H), 6.11 (d, J=7.7 Hz, 1H), 4.71 (s, 2H), 4.50 (s, 2H), 3.80 (s, 2H), 2.23 (s, 3H), 0.86 (m, 2H), 0.78 (m, 2H). Mass spectrum (MALDI-TOF, α-cyanohydroxycinnamic acid matrix) calcd. for $C_{20}H_{26}N_6O_5S$: 463.2 (M+H), 485.2 (M+Na); Found: 463.1, 485.2.

EXAMPLE 8

3-(Benzylsulfonyl)amino-6-methyl-1-[(4-guanidinooxy) piperidinylcarbonylmethyl]-2-pyridinone trifluoroacetate

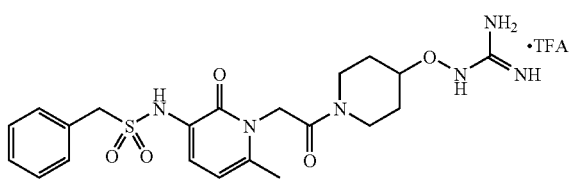

The title compound was prepared from 4-hydroxypiperidine using the procedures in steps 6-10 of Example 1 and steps 5 & 6 of Example 2, as a colorless foam. $^1$H-NMR (300 MHz, DMSO-d$_6$) δ 11.14 (s, 1H), 8.57 (s, 1H), 7.74 (br s, 4H), 7.34 (m, 5H), 7.12 (d, J=7.6 Hz, 1H), 6.09 (d, J=7.9 Hz, 1H), 5.02 (s, 2H), 4.52 (s, 2H), 3.89 (m, 3H), 3.36 (m, 1H), 3.13 (m, 1H), 2.20 (s, 3H), 2.00 (m, 1H), 1.81 (m, 1H), 1.72 (m, 1H), 1.56 (m, 1H). Mass spectrum (MALDI-TOF, α-cyano-4-hydroxycinnamic acid matrix) calcd. for $C_{21}H_{28}N_6O_5S$: 477.2 (M+H), 499.2 (M+Na), 515.1 (M+K); Found: 477.0, 498.9, 514.9.

EXAMPLE 9

3-(3-Chlorobenzylsulfonyl)amino-6-methyl-1-[(2-guanidinooxyethyl) aminocarbonylmethyl]-2-pyridinone trifluoroacetate

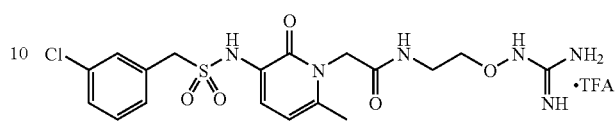

1. 3-Chlorobenzylsulfonyl chloride

A mixture of 3-chlorobenzyl chloride (1.61 g, 10 mmol) and sodium thiosulfate (1.6 g, 10 mmol) in methanol (10 mL) and water (10 mL) was heated to reflux for 3 h. The mixture was cooled to 0° C. and glacial acetic acid (10 mL) and ice were added. Chlorine gas was bubbled through the resulting suspension for 40 min, periodically adding ice to maintain an ice/liquid mixture. After an additional 1 h, the mixture was extracted with ether (3×20 mL), the combined extracts were washed with 5% sodium bisulfite (2×20 mL), brine (20 mL) and dried over Na$_2$SO$_4$. After evaporating the solvent, the residue was purified by flash column chromatography (methylene chloride) to give the title compound as a white solid (1.5 g, 67%). $^1$H-NMR (300 MHz, CDCl$_3$) δ 7.30-7.50 (m, 4H), 4.83 (s, 2H).

2. 3-(3-Chlorobenzylsulfonyl)amino-6-methyl-1-(tert-butoxycarbonylmethyl)-2-pyridinone The title compound was prepared from 3-chlorobenzylsulfonyl chloride (113 mg, 0.5 mmol), as prepared in the preceding step, and 3-amino-6-methyl-1-(tert-butoxycarbonylmethyl)-2-pyridinone (120 mg, 0.5 mmol), as prepared in step 3 of Example 1, using the procedure in step 4 of Example 1, as a white solid (180 mg, 84%). $^1$H-NMR (300 MHz, CDCl$_3$) δ 7.37 (d, J=7.6 Hz, 1H), 7.30 (m, 4H), 7.20 (s, 1H), 6.02 (d, J=7.7 Hz, 1H), 4.78 (s, 2H), 4.27 (s, 2H), 2.27 (s, 3H), 1.50 (s, 9H).

3. 3-(3-Chlorobenzylsulfonyl)amino-6-methyl-1-carboxymethyl-2-pyridinone

The title compound was prepared from 3-(3-chlorobenzylsulfonyl)amino-6-methyl-1-(tert-butoxycarbonylmethyl)-2-pyridinone (170 mg, 0.4 mmol), as prepared in the preceding step, using the procedure in step S of Example 1, as an off white solid (150 mg, 100%). $^1$H-NMR (300 MHz, CDCl$_3$) δ 8.83 (s, 1H), 7.45 (s, 1H), 7.37 (m, 3H), 7.18 (d, J=7.5 Hz, 1H), 6.11 (d, J=7.6 Hz, 1H), 4.79 (s, 2H), 4.56 (s, 2H), 2.27 (s, 3H).

4. 3-(3-Chlorobenzylsulfonyl)amino-6-methyl-1-{[N,N'-di(tert-butoxycarbonyl)] [2-(guanidinooxyethyl)aminocarbonylmethyl]}-2-pyridinone The title compound was prepared from 3-(chlorobenzylsulfonyl)amino-6-methyl-1-carboxymethyl-2-pyridinone (140 mg, 0.38 mmol), as prepared in the preceding step, and [N,N'-di(tert-butoxycarbonyl)] 2-aminoethoxyguanidine (120 mg, 0.38 mmol), as prepared in step 4 of Example 2, using the procedure in step 5 of Example 2, as a colorless foam (140 mg, 57%). $^1$H-NMR (300 MHz, CDCl$_3$) δ 9.20 (s, 1H), 8.46 (br s, 1H), 8.02 (s, 1H), 7.59 (s, 1H), 7.32 (m, 3H), 7.18 (m, 1H), 6.00 (d, J=7.7 Hz, 1H), 4.91 (s, 2H), 4.26 (s, 2H), 4.14 (t, J=5.3 Hz, 2H), 3.63 (q, J=5.2 Hz, 2H), 2.31 (s, 3H), 1.52 (s, 9H), 1.49 (s, 9H).

5. 3-(3-Chlorobenzylsulfonyl)amino-6-methyl-1-[(2-guanidinooxyethyl) aminocarbonylmethyl]-2-pyridinone trifluoroacetate The title compound was prepared from 3-(3-chlorobenzylsulfonyl)amino-6-methyl-1-{[N,N'-di(tert-butoxycarbonyl)] [2-(guanidinooxyethyl)aminocarbonylmethyl] }-2-pyridinone (140 mg, 0.22 mmol), as prepared in the preceding step, using the procedure in step 6 of Example 2, as a white solid (95 mg, 74%). ¹H-NMR (300 MHz, DMSO-d₆) δ 11.00 (s, 1H), 8.74 (s, 1H), 8.49 (t, J=5.5 Hz, 1H), 7.74 (br s, 4H), 7.45 (s, 1H), 7.40 (m, 3H), 7.18 (d, J=7.5 Hz, 1H), 6.12 (d, J=7.7 Hz, 1H), 4.75 (s, 2H), 4.56 (s, 2H), 3.83 (t, J=5.4 Hz, 2H), 3.41 (m, 2H), 2.26 (s, 3H). Mass spectrum (MALDI-TOF, α-cyano-4-hydroxycinnamic acid matrix) calcd. for C₁₈H₂₃ClN₆O₅S: 471.1 (M+H), 493.1 (M+Na), 509.1 (M+K); Found: 471.2, 493.2, 509.2.

The following compounds (Example 10 to Example 27) were prepared in a manner analogous to Example 9.

EXAMPLE 10

3-(3-Trifluoromethylbenzylsulfonyl)amino-6-methyl-1-[(2-guanidinooxyethyl)aminocarbonylmethyl]-2-pyridinone trifluoroacetate

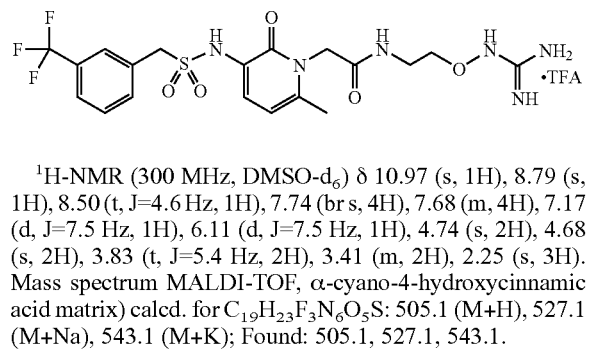

¹H-NMR (300 MHz, DMSO-d₆) δ 10.97 (s, 1H), 8.79 (s, 1H), 8.50 (t, J=4.6 Hz, 1H), 7.74 (br s, 4H), 7.68 (m, 4H), 7.17 (d, J=7.5 Hz, 1H), 6.11 (d, J=7.5 Hz, 1H), 4.74 (s, 2H), 4.68 (s, 2H), 3.83 (t, J=5.4 Hz, 2H), 3.41 (m, 2H), 2.25 (s, 3H). Mass spectrum MALDI-TOF, α-cyano-4-hydroxycinnamic acid matrix) calcd. for C₁₉H₂₃F₃N₆O₅S: 505.1 (M+H), 527.1 (M+Na), 543.1 (M+K); Found: 505.1, 527.1, 543.1.

EXAMPLE 11

3-(2-Trifluoromethylbenzyl)sulfonylamino-6-methyl-1-[(2-guanidinooxyethyl)aminocarbonylmethyl]-2-pyridinone trifluoroacetate

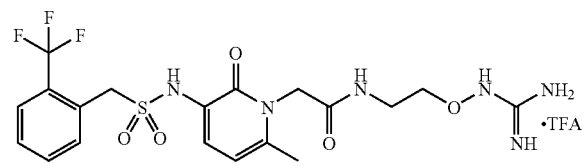

¹H-NMR (300 MHz, DMSO-d₆) δ 11.00 (s, 1H), 9.12 (s, 1H), 8.50 (t, J=5.5 Hz, 1H), 7.75 (br s, 4H), 7.68 (m, 0.3H), 7.57 (m, 1H), 7.24 (d, J=7.6 Hz, 1H), 6.16 (d, J=7.7 Hz, 1H), 4.76 (s, 2H), 4.66 (s, 2H), 3.83 (t, J=5.4 Hz, 2H), 3.39 (m, 2H), 2.28 (s, 3H). Mass spectrum (MALDI-TOF, α-cyano-4-hydroxycinnamic acid matrix) calcd. for C₁₉H₂₃F₃N₆O₅S 505.1 (M+H), 527.1 (M+Na); Found: 505.1, 527.1

EXAMPLE 12

3-(2-Iodobenzylsulfonyl)amino-6-methyl-1-[(2-guanidinooxyethyl) aminocarbonylmethyl]-2-pyridinone trifluoroacetate

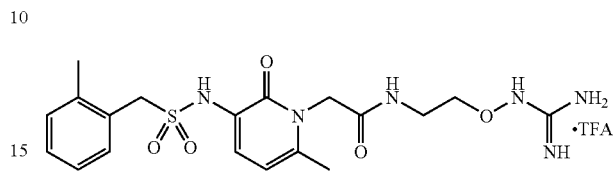

¹H-NMR (300 MHz, DMSO-d₆) δ 11.06 (s, 1H), 8.90 (s, 1H), 8.51 (t, J=5.5 Hz, 1H), 7.89 (d, J=7.9 Hz, 1H), 7.78 (br s, 4H), 7.52 (d, J=7.7 Hz, 1H), 7.39 (t, J=7.5 Hz, 1H), 7.24 (d, J=7.5 Hz, 1H), 7.09 (t, J=7.6 Hz, 1H), 6.15 (d, J=7.7 Hz, 1H), 4.75 (s, 2H), 4.65 (s, 2H), 3.83 (t, J=5.4 Hz, 2H), 3.41 (m, 2H), 2.27 (s, 3H). Mass spectrum (MALDI-TOF, α-cyano-4-hydroxycinnamic acid matrix) calcd. for C₁₈H₂₃IN₆O₅S: 563.1 (M+H), 585.1 (M+Na); Found: 562.7, 584.7.

EXAMPLE 13

3-(2-Chlorobenzylsulfonyl)amino-6-methyl-1-[(2-guanidinooxyethyl) aminocarbonylmethyl]-2-pyridinone trifluoroacetate

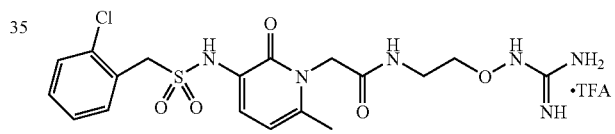

¹H-NMR (300 MHz, DMSO-d₆) δ 10.95 (s, 1H), 8.90 (s, 1H), 8.50 (t, J=5.5 Hz, 1H), 7.70 (br s, 4H), 7.54 (d, J=7.1 Hz, 1H), 7.48 (d, J=7.5 Hz, 1H), 7.36 (t, J=7.3 Hz, 2H), 7.20 (d, J=7.5 Hz, 1H), 6.14 (d, J=7.7 Hz, 1H), 4.75 (s, 2H), 4.66 (s, 2H), 3.83 (t, J=5.3 Hz, 2H), 3.41 (m, 2H), 2.27 (s, 3H). Mass spectrum (MALDI-TOF, α-cyano-4-hydroxycinnamic acid matrix) calcd. for C₁₈H₂₃ClN₆O₅S: 471.1 (M+H), 493.1 (M+Na); Found: 470.7, 492.7.

EXAMPLE 14

3-(2-Bromobenzylsulfonyl)amino-6-methyl-1-[(2-guanidinooxyethyl) aminocarbonylmethyl]-2-pyridinone trifluoroacetate

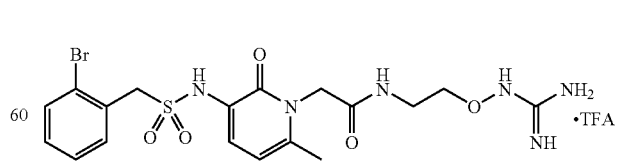

¹H-NMR (300 MHz, DMSO-d₆) δ 10.99 (s, 1H), 8.91 (s, 1H), 8.50 (t, J=5.6 Hz, 1H), 7.74 (br s, 4H), 7.65 (d, J=7.8 Hz, 1H), 7.55 (d, J=7.6 Hz, 1H), 7.38 (t, J=7.5 Hz, 1H), 7.29 (t, J=7.7 Hz, 1H), 7.21 (d, J=7.5 Hz, 1H), 6.14 (d, J=7.7 Hz, 1H), 4.75 (s, 2H), 4.67 (s, 2H), 3.83 (t, J=5.3 Hz, 2H), 3.41 (m, 2H), 2.27 (s, 3H). Mass spectrum (MALDI-TOF, α-cyano-4-hydroxycinnamic acid matrix) calcd. for $C_{18}H_{23}BrN_6O_5S$: 515.1 (M+H), 537.1 (M+Na); Found: 514.8, 536.7.

EXAMPLE 15

3-(3-Fluorobenzylsulfonyl)amino-6-methyl-1-[(2-guanidinooxyethyl) aminocarbonylmethyl]-2-pyridinone trifluoroacetate

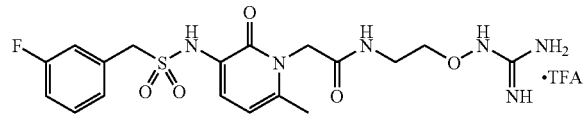

$^1$H-NMR (300 MHz, DMSO-$d_6$) δ 10.92 (s, 1H), 8.73 (s, 1H), 8.49 (t, J=5.4 Hz, 1H), 7.69 (br s, 4H), 7.38 (m, 1H), 7.22 (m, 3H), 7.17 (d, J=7.5 Hz, 1H), 6.12 (d, J=7.7 Hz, 1H), 4.74 (s, 2H), 4.56 (s, 2H), 3.83 (t, J=5.3 Hz, 2H), 3.39 (m, 2H), 2.26 (s, 3H). Mass spectrum (MALDI-TOF, α-cyano-4-hydroxycinnamic acid matrix) calcd. for $C_{18}H_{23}FN_6O_5S$: 455.2 (M+H), 477.1 (M+Na), 493.1 (M+K); Found: 455.3, 477.3, 493.2.

EXAMPLE 16

3-(4-Chlorobenzylsulfonyl)amino-6-methyl-1-[(2-guanidinooxyethyl) aminocarbonylmethyl]-2-pyridinone trifluoroacetate

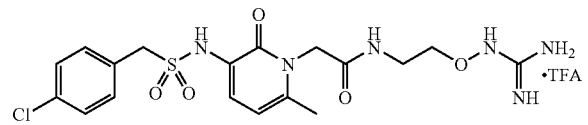

$^1$H-NMR (300 MHz, DMSO-$d_6$) δ 11.02 (s, 1H), 8.66 (s, 1H), 8.50 (t, J=5.5 Hz, 1H), 7.75 (br s, 4H), 7.39 (s, 4H), 7.16 (d, J=7.5 Hz, 1H), 6.11 (d, J=7.6 Hz, 1H), 4.74 (s, 2H), 4.54 (s, 2H), 3.83 (t, J=5.4 Hz, 2H), 3.41 (m, 2H), 2.26 (s, 3H). Mass spectrum (MALDI-TOF, α-cyano-4-hydroxycinnamic acid matrix) calcd. for $C_{18}H_{23}ClN_6O_5S$: 471.1 (M+H), 493.1 (M+Na); Found: 471.1, 493.1.

EXAMPLE 17

3-((2-Chloro-6-fluoro)benzylsulfonyl)amino-6-methyl-1-[(2-guanidinooxyethyl)aminocarbonylmethyl]-2-pyridinone trifluoroacetate

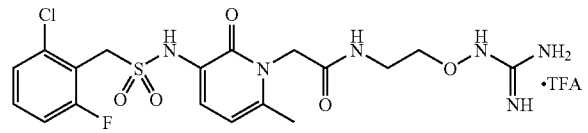

$^1$H-NMR (300 MHz, DMSO-$d_6$) δ 10.96 (s, 1H), 9.11 (s, 1H), 8.49 (t, J=5.5 Hz, 1H), 7.71 (br s, 4H), 7.45 (dd, J=8.1, 2.1 Hz, 1H), 7.37 (d, J=7.6 Hz, 1H), 7.28 (d, J=8.1 Hz, 1H), 7.23 (d, J=7.5 Hz, 1H), 6.16 (d, J=7.8 Hz, 1H), 4.74 (s, 2H), 4.68 (s, 2H), 3.83 (t, J=5.4 Hz, 2H), 3.40 (t, J=5.3 Hz, 2H), 2.27 (s, 3H). Mass spectrum (MALDI-TOF, α-cyano-4-hydroxycinnamic acid matrix) calcd. for $C_{18}H_{22}ClFN_6O_5S$: 489.1 (M+H), 511.1 (M+Na); Found: 488.9, 510.9.

EXAMPLE 18

3-(2-Fluorobenzylsulfonyl)amino-6-methyl-1-[(2-guanidinooxyethyl) aminocarbonylmethyl]-2-pyridinone trifluoroacetate

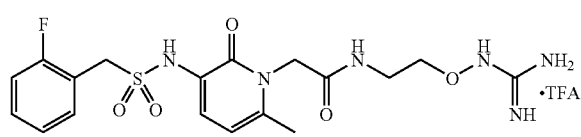

$^1$H-NMR (300 MHz, DMSO-$d_6$) δ 11.03 (s, 1H), 8.86 (s, 1H), 8.51 (t, J=5.5 Hz, 1H), 7.76 (br s, 4H), 7.47 (m, 2H), 7.20 (m, 3H), 6.13 (d, J=7.7 Hz, 1H), 4.74 (s, 2H), 4.55 (s, 2H), 3.83 (t, J=5.5 Hz, 2H), 3.39 (t, J=5.6 Hz, 2H), 2.26 (s, 3H). Mass spectrum (MALDI-TOF, α-cyano-4-hydroxycinnamic acid matrix) calcd for $C_{18}H_{23}FN_6O_5S$: 455.2 (M+H), 477.1 (M+Na); Found: 455.0, 477.1.

EXAMPLE 19

3-(4-Fluorobenzylsulfonyl)amino-6-methyl-1-[(2-guanidinooxyethyl) aminocarbonylmethyl]-2-pyridinone trifluoroacetate

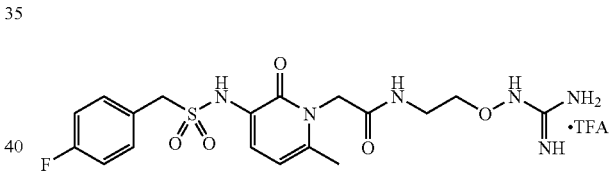

$^1$H-NMR (300 MHz, DMSO-$d_6$) δ 11.04 (s, 1H), 8.63 (s, 1H), 8.51 (t, J=5.6 Hz, 1H), 7.76 (br s, 4H), 7.39 (m, 2H), 7.16 (m, 3H), 6.11 (d, J=7.7 Hz, 1H), 4.74 (s, 2H), 4.53 (s, 2H), 3.84 (t, J=5.3 Hz, 2H), 3.41 (t, J=5.5 Hz, 2H), 2.25 (s, 3H). Mass spectrum (MALDI-TOF, α-cyano-4-hydroxycinnamic acid matrix) calcd. for $C_{18}H_{23}FN_6O_5S$: 455.2 (M+H), 477.1 (M+Na); Found: 455.0, 476.9.

EXAMPLE 20

3-(2,3-Dichlorobenzylsulfonyl)amino-6-methyl-1-[(2-guanidinooxyethyl)aminocarbonylmethyl]-2-pyridinone trifluoroacetate

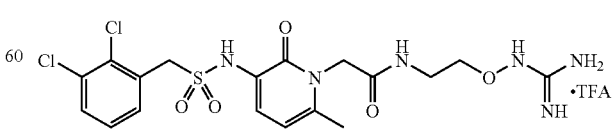

$^1$H-NMR (300 MHz, DMSO-$d_6$) δ 10.92 (s, 1H), 9.02 (s, 1H), 8.49 (t, J=5.5 Hz, 1H), 7.69 (br s, 4H), 7.64 (d, J=8.0 Hz, 1H), 7.54 (d, J=7.7 Hz, 1H), 7.36 (t, J=7.9 Hz, 1H), 7.23 (d,

J=7.5 Hz, 1H), 6.15 (d, J=7.7 Hz, 1H), 4.75 (s, 4H), 3.83 (t, J=5.3 Hz, 2H), 3.41 (t, J=5.5 Hz, 2H), 2.27 (s, 3H). Mass spectrum (MALDI-TOF, α-cyano-4-hydroxycinnamic acid matrix) calcd. for $C_{18}H_{22}Cl_2N_6O_5S$: 505.1 (M+H), 527.1 (M+Na); Found: 504.8, 527.1.

EXAMPLE 21

3-(3,4-Difluorobenzylsulfonyl)amino-6-methyl-1-[(2-guanidinooxyethyl)aminocarbonylmethyl]-2-pyridinone trifluoroacetate

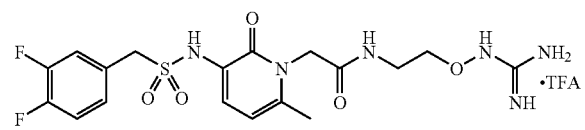

$^1$H-NMR (300 MHz, DMSO-$d_6$) δ 10.99 (s, 1H), 8.77 (s, 1H), 8.49 (t, J=5.5 Hz, 1H), 7.67 (br s, 4H), 7.49 (m, 1H), 7.42 (m, 1H), 7.24 (m, 1H), 7.19 (d, J=7.5 Hz, 1H), 6.13 (d, J=7.7 Hz, 1H), 4.74 (s, 2H), 4.54 (s, 2H), 3.83 (t, J=5.3 Hz, 2H), 3.39 (t, J=5.4 Hz, 2H), 2.26 (s, 3H). Mass spectrum (MALDI-TOF, α-cyano-4-hydroxycinnamic acid matrix) calcd. for $C_{18}H_{22}F_2N_6O_5S$: 473.1 (M+H), 495.1 (M+Na); Found: 473.1, 495.1.

EXAMPLE 22

3-(2,4-Dichlorobenzylsulfonyl)amino-6-methyl-1-[(2-guanidinooxyethyl)aminocarbonylmethyl]-2-pyridinone trifluoroacetate

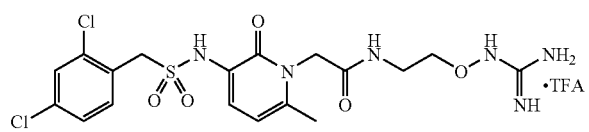

$^1$H-NMR (300 MHz, DMSO-$d_6$) δ 10.99 (s, 1H), 8.99 (s, 1H), 8.51 (t, J=5.5 Hz, 1H), 7.74 (br s, 4H), 7.66 (s, 1H), 7.58 (d, J=8.4 Hz, 1H), 7.44 (d, J=8.3 Hz, 1H), 7.22 (d, J=7.6 Hz, 1H), 6.15 (d, J=7.9 Hz, 1H), 4.75 (s, 2H), 4.66 (s, 2H), 3.83 (t, J=5.3 Hz, 2H), 3.41 (t, J=5.2 Hz, 2H), 2.27 (s, 3H). Mass spectrum (MALDI-TOF, α-cyano-4-hydroxycinnamic acid matrix) calcd. for $C_{18}H_{22}Cl_2N_6O_5S$: 505.1 (M+H), 527.1 (M+Na); Found: 505.1, 527.1.

EXAMPLE 23

3-(2,5-Dichlorobenzylsulfonyl)amino-6-methyl-1-[(2-guanidinooxyethyl)aminocarbonylmethyl]-2-pyridinone trifluoroacetate

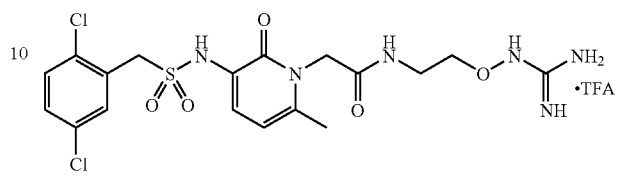

$^1$H-NMR (300 MHz, DMSO-$d_6$) δ 10.95 (s, 1H), 9.07 (s, 1H), 8.49 (t, J=5.5 Hz, 1H), 7.71 (br s, 4H), 7.66 (s, 1H), 7.52 (d, J=8.5 Hz, 1H), 7.45 (d, J=8.6 Hz, 1H), 7.24 (d, J=7.5 Hz, 1H), 6.15 (d, J=7.8 Hz, 1H), 4.76 (s, 2H), 4.67 (s, 2H), 3.83 (t, J=5.4 Hz, 2H), 3.38 (t, J=5.5 Hz, 2H), 2.27 (s, 3H). Mass spectrum (MALDI-TOF, α-cyano-4-hydroxycinnamic acid matrix) calcd. for $C_{18}H_{22}Cl_2N_6O_5S$: 505.1 (M+H), 527.1 (M+Na); Found: 505.1, 526.9.

EXAMPLE 24

3-(3,4-Dichlorobenzylsulfonyl)amino-6-methyl-1-[(2-guanidinooxyethyl)aminocarbonylmethyl]-2-pyridinone trifluoroacetate

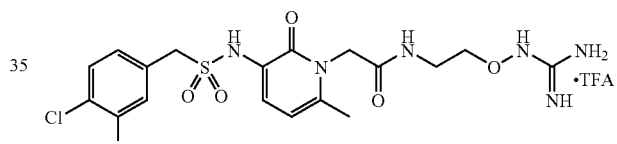

$^1$H-NMR (300 MHz, DMSO-$d_6$) δ 10.96 (s, 1H), 8.82 (s, 1H), 8.50 (t, J=5.5 Hz, 1H), 7.72 (br s, 4H), 7.66 (s, 1H), 7.61 (d, J=8.3 Hz, 1H), 7.60 (d, J=8.3 Hz, 1H), 7.22 (d, J=7.6 Hz, 1H), 6.12 (d, J=7.7 Hz, 1H), 4.75 (s, 2H), 4.59 (s, 2H), 3.83 (t, J=5.4 Hz, 2H), 3.38 (m, 2H), 2.26 (s, 3H). Mass spectrum (MALDI-TOF, α-cyano-4-hydroxycinnamic acid matrix) calcd. for $C_{18}H_{22}Cl_2N_6O_5S$: 505.1 (M+H), 527.1. (M+Na); Found: 504.8, 526.8.

EXAMPLE 25

3-(1-naphthalenylmethylsulfonyl)amino-6-methyl-1-[(2-guanidinooxyethyl)aminocarbonylmethyl]-2-pyridinone trifluoroacetate

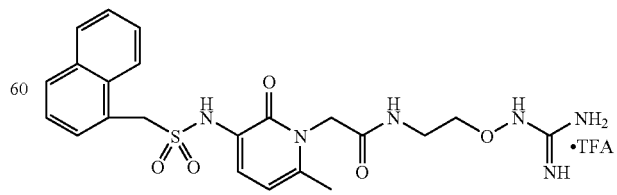

$^1$H-NMR (300 MHz, DMSO-$d_6$) δ 11.02 (s, 1H), 8.72 (s, 1H), 8.51 (t, J=5.5 Hz, 1H), 8.20 (m, 1H), 7.93 (m, 1H), 7.75

(br s, 4H), 7.67 (m, 1H), 7.53 (m, 4H), 7.16 (d, J=7.5 Hz, 1H), 6.10 (d, J=7.5 Hz, 1H), 5.08 (s, 2H), 4.74 (s, 2H), 3.84 (t, J=5.2 Hz, 2H), 3.42 (t, J=5.3 Hz, 2H), 2.26 (s, 3H). Mass spectrum (LCMS, ESI) calcd. for $C_{22}H_{26}N_6O_5S$: 487.5 (M+H); Found: 487.8.

EXAMPLE 26

3-(2-naphthalenylmethylsulfonyl)amino-6-methyl-1-[(2-guanidinooxyethyl)aminocarbonylmethyl]-2-pyridinone trifluoroacetate

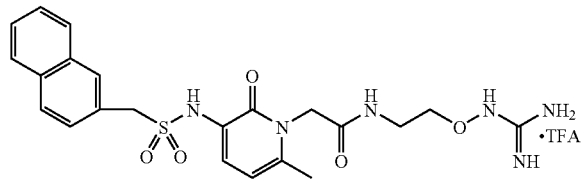

$^1$H-NMR (300 MHz, DMSO-$d_6$) δ 11.06 (s, 1H), 8.62 (s, 1H), 8.52 (t, J=5.3 Hz, 1H), 7.86 (m, 4H), 7.78 (br s, 4H), 7.52 (m, 3H), 7.21 (d, J=7.5 Hz, 1H), 6.07 (d, J=7.7 Hz, 1H), 4.74 (s, 2H), 4.69 (s, 2H), 3.85 (t, J=5.2 Hz, 2H), 3.43 (t, J=5.3 Hz, 2H), 2.22 (s, 3H). Mass spectrum (LCMS, ESI) calcd. for $C_{22}H_{26}N_6O_5S$: 487.5 (M+H); Found: 487.1.

EXAMPLE 27

3-(2-Methylbenzylsulfonyl)amino-6-methyl-1-[(2-guanidinooxyethyl)aminocarbonylmethyl]-2-pyridinone trifluoroacetate

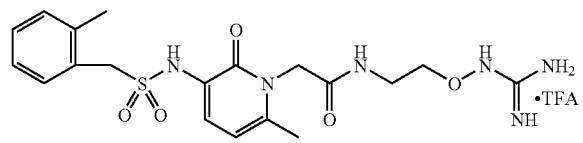

$^1$H-NMR (300 MHz, DMSO-$d_6$) δ 11.07 (s, 1H), 8.72 (s, 1H), 8.51 (t, J=5.5 Hz, 1H), 7.78 (br s, 4H), 7.21 (m, 4H), 7.12 (d, J=7.5 Hz, 1H), 6.11 (d, J=7.7 Hz, 1H), 4.75 (s, 2H), 4.54 (s, 2H), 3.83 (t, J=5.4 Hz, 2H), 3.41 (t, J=5.4 Hz, 2H), 2.34 (s, 3H), 2.26 (s, 3H). Mass spectrum (LCMS, ESI) calcd. for $C_{19}H_{26}N_6O_5S$: 451.3 (M+H); Found: 451.2.

EXAMPLE 28

3-(3-Chlorobenzylsulfonyl)-N-methylamino-6-methyl-1-[(2-guanidinooxyethyl)aminocarbonylmethyl]-2-pyridinone trifluoroacetate

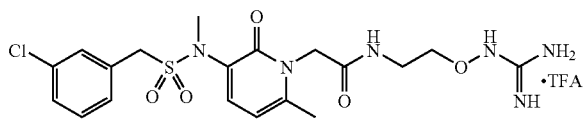

1. 3-(3-Chlorobenzylsulfonyl)-N-methylamino-6-methyl-1-(tert-butoxycarbonylmethyl)-2-pyridinone To a suspension of 3-(3-chlorobenzylsulfonyl)amino-6-methyl-1-(tert-butoxycarbonylmethyl)-2-pyridinone (190 mg, 0.44 mmol), as prepared in step 2 of Example 9, and potassium carbonate (276 mg, 2.0 mmol) in acetonitrle (10 mL) was added iodomethane (142 mg, 1.0 mmol). The mixture was stirred at ambient temperature overnight Water (50 mL) was added to the mixture, extracted with ethyl acetate (3×30 mL). The organic layer was washed with brine (2×30 mL) and dried over $Na_2SO_4$. The solvent was evaporated to give the title compound as a colorless foam (195 mg, 100%). $^1$H-NMR (300 MHz, CDCl$_3$) δ 7.51 (s, 1H), 7.48 (d, J=7.5 Hz, 1H), 7.33 (m, 3H), 6.11 (d, J=7.6 Hz, 1H), 4.75 (s, 2H), 4.38 (s, 2H), 3.22 (s, 3H), 2.33 (s, 3H), 1.49 (s, 9H).

2. 3-(3-Chlorobenzylsulfonyl)-N-methylamino-6-methyl-1-[(2-guanidinooxyethyl)aminocarbonylmethyl]-2-pyridinone trifluoroacetate The title compound was prepared from 3-(3-chlorobenzylsulfonyl)-N-methylamino-6-methyl-1-(tert-butoxycarbonylmethyl)-2-pyridinone, as prepared in the preceding step, using the procedures in step 5 of Example 1 and steps 5 and 6 of Example 2, as a white solid. $^1$H-NMR (300 MHz, DMSO-$d_6$) δ 10.97 (s, 1H), 8.50 (t, J=5.5 Hz, 1H), 7.73 (br s, 4H), 7.53 (s, 1H), 7.42 (m, 3H), 7.37 (d, J=7.5 Hz, 1H), 6.12 (d, J=7.5 Hz, 1H), 4.76 (s, 2H), 4.53 (s, 2H), 3.83 (t, J=5.4 Hz, 2H), 3.39 (t, J=5.5 Hz, 2H), 3.05 (s, 3H), 2.31 (s, 3H). Mass spectrum (MALDI-TOF, α-cyano-4-hydroxycinnamic acid matrix) calcd. for $C_{19}H_{25}ClN_6O_5S$: 485.1 (M+H), 507.1 (M+Na); Found: 485.1, 507.1.

EXAMPLE 29

3-(3,4-Dichlorobenzylsulfonyl)-N-methylamino-6-methyl-1-[(2-guanidinooxyethyl)aminocarbonylmethyl]-2-pyridinone trifluoroacetate

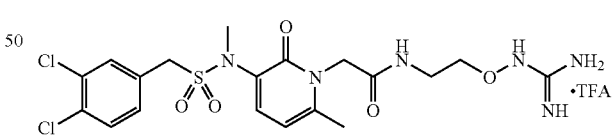

The title compound was prepared in a manner analogous to Example 28. $^1$H-NMR (300 MHz, DMSO-$d_6$) δ 10.97 (s, 1H), 8.51 (t, J=5.5 Hz, 1H), 7.74 (br s, 5H), 7.66 (d, J=8.2 Hz, 1H), 7.45 (m, 1H), 7.42 (d, J=7.5 Hz, 1H), 6.22 (d, J=7.6 Hz, 1H), 4.77 (s, 2H), 4.55 (s, 2H), 3.83 (t, J=5.3 Hz, 2H), 3.39 (t, J=5.6 Hz, 2H), 3.05 (s, 3H), 2.32 (s, 3H). Mass spectrum (MALDI-TOF, α-cyano-4-hydroxycinnamic acid matrix) calcd. for $C_{19}H_{24}Cl_2N_6O_5S$ 519.1 (M+H), 541.1 (M+Na); Found: 519.3, 541.4.

EXAMPLE 30

3-(2-Chlorophenylsulfonyl)amino-6-methyl-1-[(2-guanidinooxyethyl)aminocarbonylmethyl]-2-pyridinone trifluoroacetate

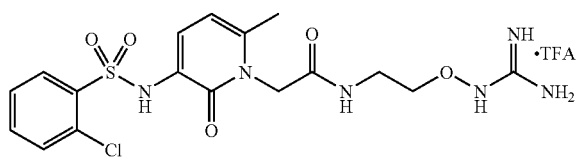

1. 3-(Benzyloxycarbonyl)amino-6-methyl-1-carboxymethyl-2-pyridinone

To a solution of 3-benzyloxycarbonylamino-6-methyl-1-(tert-butoxycarbonylmethyl)-2-pyridinone (6.0 g, 17 mmol), as prepared in step 2 of Example 1, in methylene chloride (12 mL) was added trifluoroacetic acid (12 mL) and the reaction stirred at ambient temperature. After 30 minutes the reaction was concentrated in vacuo, dissolved in methylene chloride, and diluted with hexane. The precipitated product was collected by filtration and dried in vacuo giving a quantitative yield of white solid. $^1$H NMR (300 MHz, DMSO-$d_6$) δ 13.17 (br s, 1H), 8.36 (s, 1H), 7.74 (d, 1H, J=7.5 Hz), 7.35 (m, 5H), 6.18 (d, 1H, J=7.7 Hz), 5.15 (s, 2H), 4.77 (s, 2H), 2.25 (s, 3H).

2. 3-Benzyloxycarbonylamino-6-methyl-1-{[N,N'-di(tert-butoxycarbonyl)] [2-(guanidinooxyethyl)aminocarbonyl]}-2-pyridinone To a solution of 3-(benzyloxycarbonyl)amino-6-methyl-1-carboxymethyl-2-pyridinone (0.85 g, 2.5 mmol), as prepared in the preceding step, and [N,N'-di(tert-butoxycarbonyl)] 3-amino-1-ethoxyguanidine (0.86 g, 2.7 mmol), as prepared in step 4 of Example 2, in N,N-dimethylformamide (42 mL), was added N,N-diisopropylethylamine (0.59 mL, 3.4 mmol) and Castro's reagent (BOP; 1.31 g, 3.0 mmol). After stirring 2 hours at ambient temperature, the reaction was concentrated in vacuo and the crude product recrystallized from 3:1 ethyl acetate:hexane giving a colorless solid. $^1$H NMR (300 MHz, DMSO-$d_6$) δ 9.11 (s, 1H), 8.71 (s, 1H), 8.36 (m, 1H), 8.30 (s, 1H), 7.74 (d, 1H, J=7.6 Hz), 7.37 (m, 5H), 6.16 (d, 1H, J=8.1 Hz), 5.15 (s, 2H), 4.72 (s, 2H), 3.87 (t, 2H, J=5 Hz), 3.39 (m, 2H), 2.81 (d, 2H, J=11 Hz), 2.24 (s, 3H), 1.42 (s, 9H), 1.39 (s, 9H).

3. 3-Amino-6-methyl-1-{[N,N'-di(tert-butoxycarbonyl)] [2-(guanidinooxyethyl)aminocarbonyl]}-2-pyridinone To a solution of 3-benzyloxycarbonylamino-6-methyl-1-{[N,N'-di(tert-butoxycarbonyl)] [2-(guanidinooxyethyl)aminocarbonyl]}-2-pyridinone (0.80 g, 1.3 mmol), as prepared in the preceding step, in 2:1 ethanol:tetrahydrofuran (96 mL) was added 10% palladium (0) on activated carbon (64 mg). After degassing and backfilling with nitrogen, the reaction was stirred under hydrogen gas at atmospheric pressure for 1 hour, filtered through Celite, and the filtrate concentrated in vacuo giving a colorless solid that was used without further purification.

4. 3-(2-Chlorophenylsulfonyl)amino-6-methyl-1-{[N,N'-di(tert-butoxycarbonyl)] [2-(guanidinooxyethyl)aminocarbonyl]}-2-pyridinone To a solution of 3-amino-6-methyl-1-{[N,N'-di(tert-butoxycarbonyl)] [2-(guanidinooxyethyl) aminocarbonyl]}-2-pyridinone (0.11 g, 0.23 mmol), as prepared in the preceding step, in methylene chloride (4 mL) was added 2-chlorobenzenesulfonyl chloride (0.048 g, 0.23 mmol) and N-methylmorpholine (0.024 mL, 0.22 mmol). After stirring 4 hours at ambient temperature, the reaction was diluted with additional methylene chloride and washed with saturated aqueous NaHCO$_3$, 10% aqueous citric acid, and brine. The organic layer was then separated and evaporated in vacuo and the crude product used without further purification.

5. 3-(2-Chlorophenylsulfonyl)amino-6-methyl-1-[(2-guanidinooxyethyl) aminocarbonylmethyl]-2-pyridinone trifluoroacetate 3-(2-Chlorophenylsulfonyl)amino-6-methyl-1-{[N,N'-di(tert-butoxycarbonyl)] [2-(guanidinooxyethyl)aminocarbonyl]}-2-pyridinone, as prepared in the preceding step, was dissolved in methylene chloride (ca 4 mL) and treated with neat trifluoroacetic acid (ca. 2 mL) at ambient temperature for 4 hours. After evaporation, the crude product was dissolved in methylene chloride, washed with saturated aqueous NaHCO$_3$, 10% aqueous citric acid, and brine, dried over Na$_2$SO$_4$, filtered and evaporated. The crude product was then purified on a Waters silica Sep-Pak (gradient elution: 10-50% ethyl acetate in methylene chloride) giving the title compound (0.11 g, 89%). $^1$H NMR (300 MHz, DMSO-$d_6$) δ 10.97 (s, 1H), 9.21 (s, 1H), 8.45 (t, 1H, J=5.6 Hz), 8.01 (m, 1H), 7.73 (br s, 4H), 7.64 (m, 2H), 7.49 (m, 1H), 7.21 (d, 1H, J=7.6 Hz), 6.08 (d, 1H, J=7.9 Hz), 4.64 (s, 2H), 3.80 (t, 2H, J=5.3 Hz), 3.40 (m, 2H), 2.19 (s, 3H). Mass spectrum (MALDI-TOF, α-cyano-4-hydroxycinnamic acid matrix) calcd. for C$_{17}$H$_{21}$N$_6$O$_5$SCl: 479.1 (M+Na), 457.1 (M+H). Found: 479.4, 457.3.

EXAMPLE 31

3-(4-Chlorophenylsulfonyl)amino-6-methyl-1-[(2-guanidinooxyethyl) aminocarbonylmethyl]-2-pyridinone trifluoroacetate

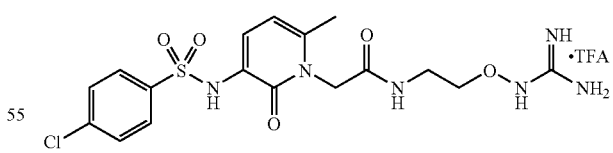

The title compound was prepared as in Example 30 starting with 4-chlorobenzenesulfonyl chloride (0.048 g, 0.23 mmol). $^1$H NMR (300 MHz, DMSO-$d_6$) δ 10.94 (s, 1H), 9.50 (s, 1H), 8.41 (t, 1H, J=5.6 Hz), 7.80 (m, 2H), 7.69 (br s, 4H), 7.60 (m, 2H), 7.28 (d, 1H, J=7.6 Hz), 6.11 (d, 1H, J=7.7 Hz), 4.60 (s, 2H), 3.79 (t, 2H, J=5.3 Hz), 3.39 (m, 2H), 2.20 (s, 3H). Mass spectrum (MALDI-TOF, α-cyano-4-hydroxycinnamic acid matrix) calcd. for C$_{17}$H$_{21}$N$_6$O$_5$SCl: 479.1 (M+Na), 457.1 (M+H). Found: 479.4, 457.0.

EXAMPLE 32

3-(Phenylsulfonyl)amino-6-methyl-1-[(2-guanidinooxyethyl) aminocarbonylmethyl]-2-pyridinone trifluoroacetate

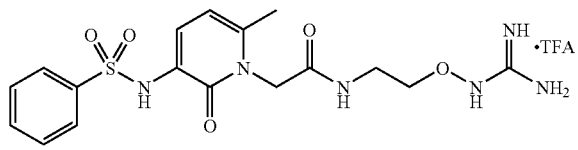

The title compound was prepared as in Example 30 starting with benzenesulfonyl chloride (0.030 mL, 0.23 mmol). $^1$H NMR (300 MHz, DMSO-d$_6$) δ 11.00 (s, 1H), 9.34 (s, 1H), 8.43 (t, 1H, J=5.5 Hz), 7.82 (m, 2H), 7.75 (br s, 4H), 7.60 (m, 3H), 7.26 (d, 1H, J=7.6 Hz), 6.09 (d, 1H, J=7.6 Hz), 4.61 (s, 2H), 3.79 (t, 2H, J=5.3 Hz), 3.38 (m, 2H), 2.19 (s, 3H). Mass spectrum (MALDI-TOF, α-cyano-4-hydroxycinnamic acid matrix) calcd. for C$_{17}$H$_{21}$N$_6$O$_5$SCl: 445.1 (M+Na), 423.1 (M+H). Found: 445.1, 423.0.

EXAMPLE 33

3-(3-Chlorophenylsulfonyl)amino-6-methyl-1-[(2-guanidinooxyethyl) aminocarbonylmethyl]-2-pyridinone trifluoroacetate

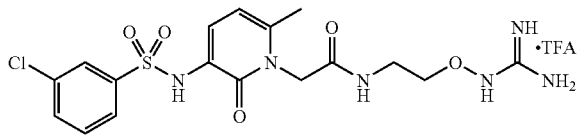

The title compound was prepared as in Example 30 starting with 3-chlorobenzenesulfonyl chloride (0.048 g, 0.23 mmol). $^1$H NMR (300 MHz, DMSO-d$_6$) δ 11.14 (br s, 1H), 9.63 (s, 1H), 8.45 (br s, 1H), 7.77 (m, 6H), 7.55 (t, 1H, J=7.9 Hz), 7.29 (d, 1H, J=7.6 Hz), 6.11 (d, 1H, J=7.7 Hz), 4.61 (s, 2H), 3.79 (t, 2H, J=5.3 Hz), 3.39 (m, 2H), 2.20 (s, 3H). Mass spectrum (MALDI-TOF, α-cyano-4-hydroxycinnamic acid matrix) calcd. for C$_{17}$H$_{21}$N$_6$O$_5$SCl: 479.1 (M+Na), 457.1 (M+H). Found: 479.0, 457.0.

EXAMPLE 34

3-(2-Methylsulfonylphenyl)sulfonylamino-6-methyl-1-[(22 guanidinooxyethyl)aminocarbonylmethyl]-2-pyridinone trifluoroacetate

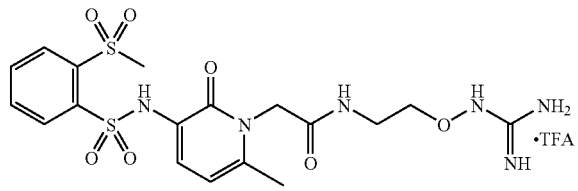

The title compound was prepared in a manner analogous to Example 30. $^1$H-NMR (300 MHz, DMSO-d$_6$) δ 8.32 (t, J=5.5 Hz, 1H), 8.21 (d, J=7.6 Hz, 1H), 8.13 (d, J=7.5 Hz, H), 7.92 (m, 2H), 7.43 (d, J=7.4 Hz, 1H), 6.21 (br s, 4H), 6.12 (d, J=7.5 Hz, 1H), 4.58 (s, 2H), 3.68 (t, J=5.4 Hz, 2H), 3.47 (s, 3H), 3.29 (t, 2H, J=5.6 Hz), 2.17 (s, 3H). Mass spectrum (MALDI-TOF, α-cyano-4-hydroxycinnamic acid matrix) calcd. for C$_{18}$H$_{24}$N$_6$O$_5$S$_2$: 501.1. (M+H), 523.1 (M+Na), 539.1 (M+K); Found: 501.1, 523.3, 539.4.

EXAMPLE 35

3-(2-Naphthalenylsulfonyl)amino-6-methyl-1-[(2-guanidinooxy ethyl) aminocarbonylmethyl]-2-pyridinone trifluoroacetate

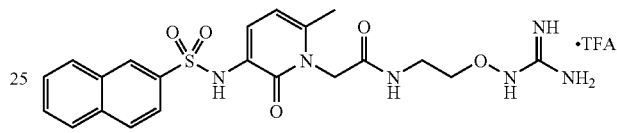

1. 3-(2-Naphthalenylsulfonyl)amino-6-methyl 0.1-{[N,N'-di(tert-butoxycarbonyl)] [2-(guanidinooxyethyl)aminocarbonyl]}-2-pyridinone To a solution of 3-amino-6-methyl-1-{[N,N'-di(tert-butoxycarbonyl)] [2-(guanidinooxyethyl) aminocarbonyl]}-2-pyridinone (0.050 g, 0.10 mmol), as prepared in step 3 of Example 30, in methylene chloride (2 mL) was added 2-naphthalenesulfonyl chloride (0.023 g, 0.10 mmol) and diethylaminomethyl-polystyrene resin (0.033 g, ca. 0.10 mmol). After stirring 5 hours at ambient temperature, aminomethylated polystyrene resin (0.10 g, ca. 0.20 mmol) and more methylene chloride (2 mL) were added and the reaction was stirred an additional 16 hours. The resulting suspension was poured onto a Waters silica Sep-Pak and eluted with 10-50% ethyl acetate in methylene chloride, and the eluted product concentrated in vacuo and used directly in the next step.

2. 3-(2-Naphthalenylsulfonyl)amino-6-methyl-1-[(2-guanidinooxyethyl) aminocarbonylmethyl]-2-pyridinone trifluoroacetate The product of the preceding step was dissolved in methylene chloride (ca. 2 mL) and treated with neat trifluoroacetc acid (ca. 1 mL) at ambient temperature for 4 hours. After evaporation, the crude product was purified on a Waters silica Sep-Pak with 5% methanol in methylene chloride giving the title compound (0.007 g, 12%). $^1$H NMR (300 MHz, DMSO-d$_6$) δ 8.42 (m, 1H), 7.98 (m, 3H), 7.78 (dd, 1H, J=8.7 Hz, 1.9 Hz), 7.63 (m, 2H), 7.55 (d, 1H, J=7.6 Hz), 6.19 (dd, 1H, J=7.7 Hz, 0.8 Hz), 4.64 (s, 2H), 3.83 (t, 2H, J=5 Hz), 3.42 (t, 2H, J=5 Hz), 2.26 (s, 3H). Mass spectrum (LCMS, ESI) calcd. for C$_{17}$H$_{21}$N$_6$O$_5$SCl: 473.3 (M+H). Found: 473.2.

EXAMPLE 36

3-(4-Bromophenylsulfonyl)amino-6-methyl-1-[(2-guanidinooxyethyl) aminocarbonylmethyl]-2-pyridinone trifluoroacetate

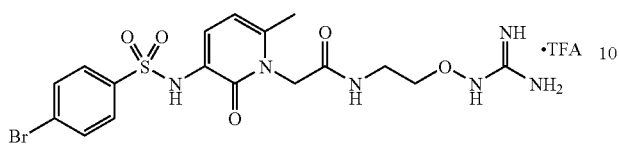

The title compound was prepared as in Example 35 starting with 4-bromobenzenesulfonyl chloride (0.026 g, 0.10 mmol). $^1$H NMR (300 MHz, DMSO-$d_6$) δ 10.90 (s, 1H), 9.51 (s, 1H), 8.41 (t, 1H, J=5.6 Hz), 7.71 (m, 8H), 7.28 (d, 1H, J=7.5 Hz), 6.11 (d, 1H, J=7.7 Hz), 4.60 (s, 2H), 4.11 (m, 2H), 3.79 (t, 2H, J=5.3 Hz), 3.40 (m, 2H), 2.20 (s, 3H). Mass spectrum (LCMS, ESI) calcd. for $C_{17}H_{21}N_6O_5SBr$: 503.0 (M+H). Found: 503.0.

EXAMPLE 37

3-(4-Fluorophenylsulfonyl)amino-6-methyl-1-[(2-guanidinooxyethyl) aminocarbonylmethyl]-2-pyridinone trifluoroacetate

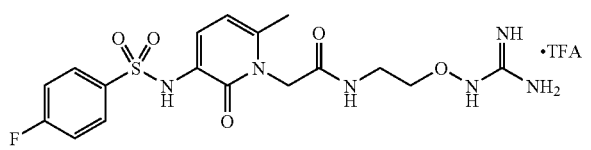

The title compound was prepared as in Example 35 starting with 4-fluorobenzenesulfonyl chloride (0.020 g, 0.10 mmol). $^1$H NMR (300 MHz, DMSO-$d_6$) δ 10.90 (s, 1H), 9.41 (s, 1H), 8.41 (t, 1H, J=5.7 Hz), 7.87 (m, 2H), 7.68 (br s, 4H), 7.36 (m, 2H), 7.28 (d, 1H, J=7.5 Hz), 6.10 (d, 1H, J=7.7 Hz), 4.60 (s, 2H), 4.10 (brd s, 2H), 3.79 (t, 2H, 5.3 Hz), 3.41 (m, 2H), 2.20 (s, 3H). Mass spectrum (LCMS, ESI) calcd. for $C_{17}H_{21}N_6O_5SF$: 441.2 (M+H). Found: 441.2.

EXAMPLE 38

3-(4-Iodophenylsulfonyl)amino-6-methyl-1-[(2-guanidinooxyethyl) aminocarbonylmethyl]-2-pyridinone trifluoroacetate

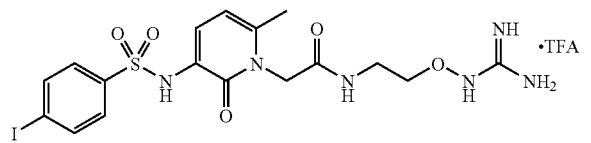

The title compound was prepared as in Example 35 starting with 4-iodobenzenesulfonyl chloride (0.030 g, 0.10 mmol). $^1$H NMR (300 MHz, DMSO-$d_6$) δ 10.95 (s, 1H), 9.48 (s, 1H), 8.42 (t, 1H, J=5.6 Hz), 7.91 (d, 2H, J=8.6 Hz), 7.72 (br s, 4H), 7.56 (d, 2H, J=8.6 Hz), 7.27 (d, 1H, J=7.6 Hz), 6.10 (d, 1H, J=7.7 Hz), 4.60 (s, 2H), 3.80 (t, 2H, J=5.3 Hz), 3.39 (m, 2H), 2.20 (s, 3H). Mass spectrum (LCMS, ESI) calcd. for $C_{17}H_{21}N_6O_5SI$: 549.1 (M+H). Found: 549.0.

EXAMPLE 39

3-(4-Methoxyphenylsulfonyl)amino-6-methyl-1-[(2-guanidinooxyethyl) aminocarbonylmethyl]-2-pyridinone trifluoroacetate

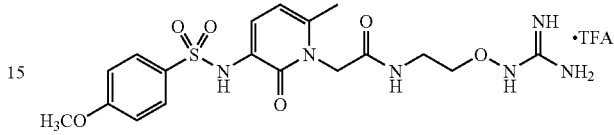

The title compound was prepared as in Example 35 starting with 4-methoxybenzenesulfonyl chloride (0.021 g, 0.10 mmol). $^1$H NMR (300 MHz, DMSO-$d_6$) δ 10.93 (s, 1H), 9.11 (s, 1H), 8.42 (m, 1H), 7.77 (d, 2H, J=9.0 Hz), 7.67 (m, 4H), 7.24 (d, 1H, J=7.5 Hz), 7.04 (d, 2H, J=8.9 Hz), 6.08 (d, 1H, J=8.0 Hz), 4.61 (s, 2H), 3.79 (m, 5H), 3.40 (m, 2H), 2.19 (s, 3H). Mass spectrum (LCMS, ESI) calcd. for $C_{18}H_{24}N_6O_6S$: 453.3 (M+H). Found: 453.2.

EXAMPLE 40

3-(4-Methylphenylsulfonyl)amino-6-methyl-1-[(2-guanidinooxyethyl) aminocarbonylmethyl]-2-pyridinone trifluoroacetate

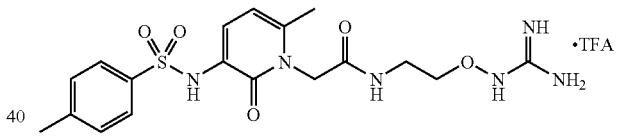

The title compound was prepared as in Example 35 starting with 4-methylbenzenesulfonyl chloride (0.021 g, 0.10 mmol). $^1$H NMR (300 MHz, DMSO-$d_6$) δ 10.93 (s, 1H), 9.21 (s, 1H), 8.43 (t, 1H, J=5.5 Hz), 7.70 (m, 6H), 7.33 (d, 2H, J=8.2 Hz), 7.24 (d, 1H, J=7.6 Hz), 6.08 (d, 1H, J=7.8 Hz), 4.61 (s, 2H), 4.10 (m, 2H), 3.79 (t, 2H, J=5.3 Hz), 3.41 (m, 2H), 2.35 (s, 3H), 2.19 (s, 3H). Mass spectrum (LCMS, ESI) calcd. for $C_{18}H_{24}N_6O_5S$: 437.3 (M+H). Found: 437.2.

EXAMPLE 41

3-(3-Trifluoromethylphenylsulfonyl)amino-6-methyl-1-[(2-guanidinooxyethyl) aminocarbonylmethyl]-2-pyridinone trifluoroacetate

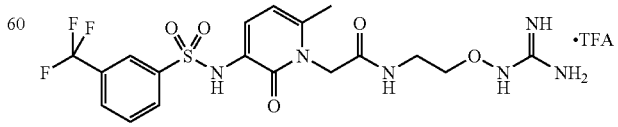

The title compound was prepared as in Example 35 starting with 3-(trifluoromethyl)benzenesulfonyl chloride (0.025 g, 0.10 mmol). $^1$H NMR (300 MHz, DMSO-d$_6$) δ 10.86 (s, 1H), 9.76 (s, 1H), 8.40 (t, 1H, J=5.5 Hz), 8.15 (s, 1H), 8.09 (d, 1H, J=8.0 Hz), 8.01 (d, 1H, J=7.9 Hz), 7.76 (t, 1H, J=7.9 Hz), 7.67 (br s, 4H), 7.32 (d, 1H, J=7.5 Hz), 6.12 (d, 1H, J=7.7 Hz), 4.59 (s, 2H), 3.78 (t, 2H, J=5.3 Hz), 3.39 (m, 2H), 2.20 (s, 3H). Mass spectrum (LCMS, ESI) calcd. for $C_{18}H_{21}N_6O_5SF_3$: 491.2 (M+H). Found: 491.1.

EXAMPLE 42

3-(3,4-dichlorophenylsulfonyl)amino-6-methyl-1-[(2-guanidinooxyethyl] aminocarbonylmhethyl)-2-pyridinone trifluoroacetate

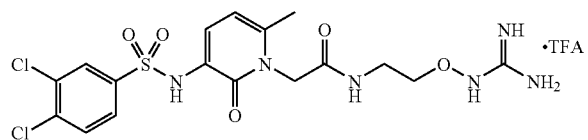

The title compound was prepared as in Example 35 starting with 3,4-dichlorobenzenesulfonyl chloride (0.025 g, 0.10 mmol). $^1$H NMR (300 MHz, DMSO-d$_6$) δ 10.90 (s, 1H), 9.73 (s, 1H), 8.41 (t, 1H, J=5.5 Hz), 8.05 (d, 1H, J=2.1 Hz), 7.80 (d, 1H, 3=8.4 Hz), 7.70 (m, 5H), 7.32 (d, 1H, J=7.5 Hz), 6.13 (d, 1H, J=7.7 Hz), 4.60 (s, 2H), 3.79 (t, 2H, J=5.3 Hz), 3.40 (m, 2H), 2.21 (s, 3H). Mass spectrum (LCMS, ESI) calcd. for $C_{17}H_{20}N_6O_5SCl_2$: 491.2 (M+H). Found: 491.2.

EXAMPLE 43

3-(3-Chloro-4-fluorophenylsulfonyl)amino-6-methyl-1-[(2-guanidinooxyethyl) aminocarbonylmethyl]-2-pyridinone trifluoroacetate

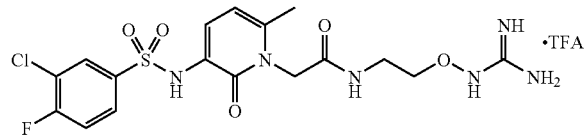

The title compound was prepared as in Example 35 starting with 3-chloro-4-fluorobenzenesulfonyl chloride (0.023 g, 0.10 mmol). $^1$H NMR (300 MHz, DMSO-d$_6$) δ 10.86 (s, 1H), 9.64 (s, 1H), 8.40 (t, 1H, J=5.6 Hz), 8.05 (dd, 1H, J=6.9 Hz, 2.3 Hz), 7.79 (ddd, 1H, J=8.7 Hz, 4.5 Hz, 2.3 Hz), 7.65 (brd s, 4H), 7.57 (t, 1H, J=8.9 Hz), 7.31 (d, 1H, J=7.5 Hz), 6.12 (d, 1H, J=7.6 Hz), 4.60 (s, 2H), 3.79 (t, 2H, J=5.3 Hz), 3.40 (m, 2H), 2.21 (s, 3H). Mass spectrum (LCMS, ESI) calcd. for $C_{17}H_{20}N_6O_5SFCl$: 475.2 (M+H). Found: 475.2.

EXAMPLE 44

3-(4-Isopropylphenylsulfonyl)amino-6-methyl-1-[(2-guanidinooxyethyl) aminocarbonylmethyl]-2-pyridinone trifluoroacetate

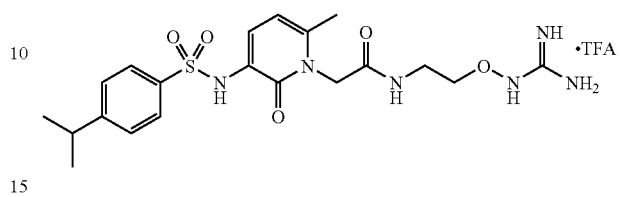

The title compound was prepared as in Example 35 starting with 4-isopropylbenzenesulfonyl chloride (0.022 g, 0.10 mmol). $^1$H NMR (300 MHz, DMSO-d$_6$) δ 10.87 (s, 1H), 9.25 (s, 1H), 8.43 (t, 1H, J=5.5 Hz), 7.77 (d, 2H, J=8.4 Hz), 7.66 (br s, 4H), 7.41 (d, 2H, J=8.4 Hz), 7.25 (d, 1H, J=7.6 Hz), 6.09 (d, 1H, J=7.7 Hz), 4.62 (s, 2H), 3.79 (t, 2H, J=5.3 Hz), 3.39 (m, 2H), 2.95 (p, 1H, J=6.9 Hz), 2.21 (s, 3H), 1.19 (d, 6H, J=6.9 Hz). Mass spectrum (LCMS, ESI) calcd. for $C_{20}H_{28}N_6O_5S$: 465.3 (M+H). Found: 465.2.

EXAMPLE 45

3-(3-Fluorophenylsulfonyl)amino-6-methyl-1-[(2-guanidinooxyethyl) aminocarbonylmethyl]-2-pyridinone trifluoroacetate

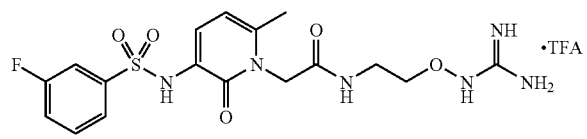

The title compound was prepared as in Example 35 starting with 3-fluorobenzenesulfonyl chloride (0.020 g, 0.10 mmol). $^1$H NMR (300 MHz, DMSO-d$_6$) δ 10.86 (s, 1H), 9.58 (s, 1H), 8.41 (t, 1H, J=5.5 Hz), 7.59 (m, 8H), 7.9 (d, 1H, J=7.6 Hz), 6.11 (d, 1H, J=7.6 Hz), 4.61 (s, 2H), 3.79 (t, 2H, J=5.3 Hz), 3.41 (m, 2H), 2.20 (s, 3H). Mass spectrum (LCMS, ESI) calcd. for $C_{17}H_{21}N_6O_5SF$: 441.2 (M+H). Found: 441.1.

EXAMPLE 46

3-(3,5-Dichlorophenylsulfonyl)amino-6-methyl-1-[(2-guanidinooxyethyl) aminocarbonylmethyl]-2-pyridinone trifluoroacetate

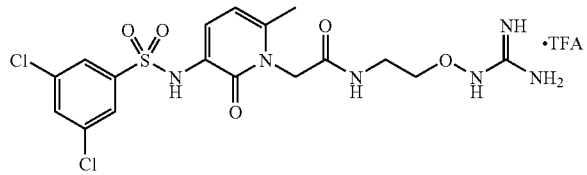

The title compound was prepared as in Example 35 starting with 3,5-dichlorobenzenesulfonyl chloride (0.025 g, 0.10 mmol). $^1$H NMR (300 MHz, DMSO-d$_6$) δ 0.86 (s, 1H), 9.85

(s, 1H), 8.41 (t, 1H, J=5.5 Hz), 7.93 (t, 1H, J=1.8 Hz), 7.83 (d, 2H, J=1.8 Hz), 7.66 (br s, 4H), 7.33 (d, 1H, J=7.6 Hz), 6.14 (d, 1H, J=7.6 Hz), 4.62 (s, 2H), 3.79 (t, 2H, J=5.3 Hz), 3.40 (m, 2H), 2.22 (s, 3H). Mass spectrum (LCMS, ESI) calcd. for $C_{17}H_{20}N_6O_5SCl_2$: 491.2 (M+H). Found: 491.2.

EXAMPLE 47

3-(3,4-Dimethoxyphenylsulfonyl)amino-6-methyl-1-[(2-guanidinooxyethyl) aminocarbonylmethyl]-2-pyridinone trifluoroacetate

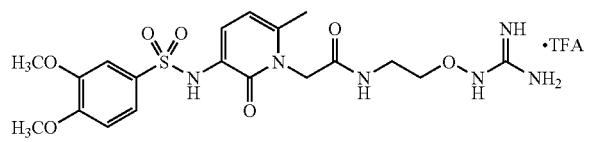

The title compound was prepared as in Example 35 starting with 3,4-dimethoxybenzenesulfonyl chloride (0.023 g, 0.10 mmol). $^1$H NMR (300 MHz, DMSO -$d_6$) δ 10.84 (s, 1H), 9.13 (s, 1H), 8.42 (t, 1H, J=5.6 Hz), 7.65 (br s, 4H), 7.41 (m, 2H), 7.26 (d, 1H, J=7.5 Hz), 7.05 (d, 1H, J=9.1 Hz), 6.09 (d, 1H, J=7.9 Hz), 4.62 (s, 2H), 3.79 (m, 9H), 3.40 (m, 2H), 2.19 (s, 3H). Mass spectrum (LCMS, ESI) calcd. for $C_{19}H_{26}N_6O_7S$: 483.3 (M+H). Found: 483.1.

EXAMPLE 48

3-(2-Thienylsulfonyl)amino-6-methyl-1-[(2-guanidinooxyethyl) aminocarbonylmethyl]-2-pyridinone trifluoroacetate

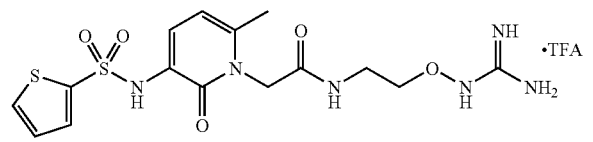

The title compound was prepared as in Example 35 starting with 2-thiophenesulfonyl chloride (0.020 g, 0.11 mmol). $^1$H NMR (300 MHz, DMSO-$d_6$) δ 10.90 (s, 1H), 9.48 (s, 1H), 8.44 (t, 1H, J=5.4 Hz), 7.90 (dd, 1H, J=5.0 Hz, 1.3 Hz), 7.69 (br s, 4H), 7.61 (dd, 1H, J=3.8 Hz, 1.3 Hz), 7.33 (d, 1H, J=7.6 Hz), 7.12 (dd, 1H, J=4.9 Hz, 3.8 Hz), 6.14 (d, 1H, J=7.7 Hz), 4.63 (s, 2H), 3.79 (t, 2H, J=5.3 Hz), 3.37 (m, 2H), 2.22 (s, 3H). Mass spectrum (LCMS, ESI) calcd. for $C_{15}H_{20}N_6O_5S_2$: 429.6 (M+H). Found: 429.1.

EXAMPLE 49

3-(1-Naphthalenylsulfonyl)amino-6-methyl-1-[(2-guanidinooxyethyl) aminocarbonylmethyl]-2-pyridinone trifluoroacetate

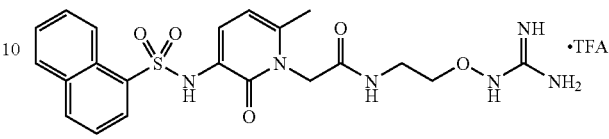

The title compound was prepared as in Example 35 starting with 1-naphthalenesulfonyl chloride (0.023 g, 0.10 mmol). $^1$H NMR (300 MHz, DMSO-$d_6$) δ 10.89 (s, 1H), 9.73 (s, 1H), 8.74 (m, 1H), 8.40 (t, 1H, J=5.6 Hz), 8.21 (m, 2H), 8.08 (m, 1H), 7.67 (m, 7H), 7.18 (d, 1H, J=7.5 Hz), 6.04 (d, 1H, J=8.0 Hz), 4.55 (s, 2H), 3.77 (t, 2H, J=5.3 Hz), 3.32 (m, 2H), 2.15 (s, 3H). Mass spectrum (LCMS, ESI) calcd. for $C_{21}H_{24}N_6O_5S$: 473.6 (M+H). Found: 473.2.

EXAMPLE 50

3-(2,4,6-Trimethylphenylsulfonyl)amino-6-methyl-1-[(2-guanidinooxyethyl) aminocarbonylmethyl]-2-pyridinone trifluoroacetate

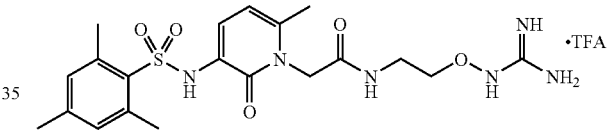

The title compound was prepared as in Example 35 starting with 2-mesitylenesulfonyl chloride (0.021 g, 0.10 mmol). $^1$H NMR (300 MHz, DMSO-$d_6$) δ 10.93 (s, 1H), 8.94 (s, 1H), 8.43 (t, 1H, J=5.5 Hz), 7.71 (brd s, 4H), 7.12 (d, 1H, J=7.5 Hz), 6.99 (s, 2H), 6.07 (d, 1H, J=7.7 Hz), 4.60 (s, 2H), 3.79 (t, 2H, J=5.3 Hz), 3.35 (q, 2H, J=5.2 Hz), 2.55 (s, 6H), 2.23 (s, 3H), 2.18 (s, 3H). Mass spectrum (LCMS, ESI) calcd. for $C_{20}H_{28}N_6O_5S$: 465.6 (M+H). Found: 465.2.

EXAMPLE 51

3-(2-Methylphenylsulfonyl)amino-6-methyl-1-[(2-guanidinooxyethyl) aminocarbonylmethyl]-2-pyridinone trifluoroacetate

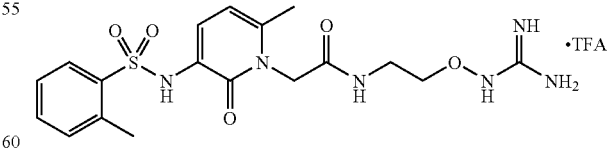

The title compound was prepared as in Example 35 starting with o-toluenesulfonyl chloride (0.019 g, 0.10 mmol). $^1$H NMR (300 MHz, DMSO-$d_6$) δ 10.89 (s, 1H), 9.27 (s, 1H), 8.43 (t, 1H, J=5.5 Hz), 7.81 (dd, 1H, J=7.9 Hz, 1.2 Hz), 7.70 (m, 4H), 7.49 (td, 1H, J=7.5 Hz, 1.3 Hz), 7.34 (dd, 2H, J=11 Hz, 8 Hz), 7.19 (d, 1H, J=7.5 Hz), 6.06 (d, 1H, J=7.7 Hz), 4.61

(s, 2H), 3.79 (t, 2H, J=5.2 Hz), 3.36 (m, 2H), 2.61 (s, 3H), 2.18 (s, 3H). Mass spectrum (LCMS, ESI) calcd. for $C_{18}H_{21}N_6O_5S$: 437.6 (M+H). Found: 437.1.

EXAMPLE 52

3-(2,5-Dimethylphenylsulfonyl)amino-6-methyl-1-[(2-guanidinooxyethyl) aminocarbonylmethyl]-2-pyridinone trifluoroacetate

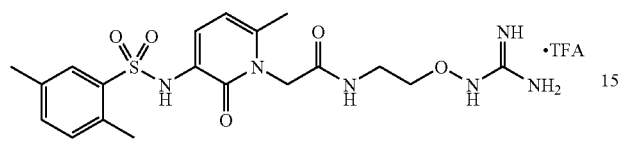

The title compound was prepared as in Example 35 starting with p-xylene-2-sulfonyl chloride (0.022 g, 0.11 mmol). $^1$H NMR (300 MHz, DMSO-$d_6$) δ 10.92 (s, 1H), 9.19 (s, 1H), 8.45 (t, 1H, J=5.4 Hz), 7.68 (m, 5H), 7.24 (m, 3H), 6.07 (d, 1H, J=7.6 Hz), 4.63 (s, 2H), 3.80 (t, 2H, J=5.2 Hz), 3.37 (m, 2H), 2.54 (s, 3H), 2.28 (s, 3H), 2.18 (s, 3H). Mass spectrum (LCMS, ESI) calcd. for $C_{19}H_{26}N_6O_5S$: 451.6 (M+H). Found: 451.1.

EXAMPLE 53

3-(2-Fluorophenylsulfonyl)amino-6-methyl-1-[(2-guanidinooxyethyl) aminocarbonylmethyl]-2-pyridinone trifluoroacetate

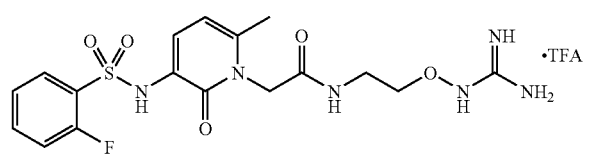

The title compound was prepared as in Example 35 starting with 2-fluorobenzenesulfonyl chloride (0.020 g, 0.10 mmol). $^1$H NMR (300 MHz, CD$_3$OD) δ 7.85 (t, 1H, J=7.5 Hz), 7.63 (m, 1H), 7.43 (d, 1H, J=7.7 Hz), 7.27 (m, 2H), 6.17 (d, 1H, J=7.7 Hz), 4.70 (s, 2H), 3.94 (t, 2H, J=5.0 Hz), 3.49 (t, 2H, J=5.0 Hz), 2.29 (s, 3H). Mass spectrum (LCMS, ESI) calcd. for $C_{17}H_{21}N_6O_5SF$: 441.5 (M+H). Found: 441.1.

EXAMPLE 54

3-(2-Chloro-6-methylphenylsulfonyl)amino-6-methyl-1-[(2-guanidinooxypropyl)aminocarbonylmethyl]-2-pyridinone trifluoroacetate

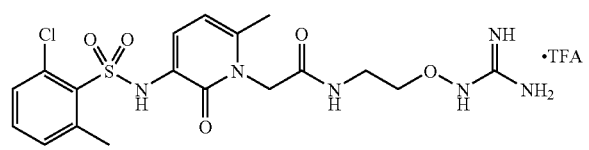

The title compound was prepared as in Example 35 starting with 2-chloro-6-methylbenzenesulfonyl chloride (0.022 g, 0.10 mmol). $^1$H NMR (300 MHz, DMSO-$d_6$) δ 10.98 (s, 1H), 9.05 (s, 1H), 8.44 (t, 1H, J=5.4 Hz), 7.74 (br s, 4H), 7.46 (m, 2H), 7.34 (m, 1H), 7.20 (d, 1H, J=7.5 Hz), 6.09 (d, 1H, J=7.8 Hz), 4.62 (s, 2H), 3.79 (t, 2H, J=5.3 Hz), 3.36 (m, 2H), 2.63 (s, 3H), 2.19 (s, 3H). Mass spectrum (LCMS, ESI) calcd. for $C_{18}H_{23}N_6O_5SCl$: 471.0 (M+H). Found: 471.1.

EXAMPLE 55

3-(3-Bromo-6-methoxyphenylsulfonyl)amino-6-methyl-1-[(2-guanidinooxyethyl)aminocarbonylmethyl]-2-pyridinone trifluoroacetate

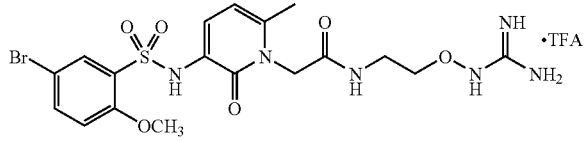

The title compound was prepared as in Example 35 starting with 5-bromo-2-methoxybenzenesulfonyl chloride (0.029 g, 0.10 mmol). $^1$H NMR (300 MHz, DMSO-$d_6$) δ 10.88 (s, 1H), 8.67 (s, 1H), 8.45 (t, 1H, J=5.6 Hz), 7.79 (m, 2H), 7.68 (br s, 4H), 7.24 (d, 1H, J=7.5 Hz), 7.16 (d, 1H, J=8.9 Hz), 6.10 (d, 1H, J=7.8 Hz), 4.65 (s, 2H), 3.80 (m, 5H), 3.37 (m, 2H), 2.19 (s, 3H). Mass spectrum (LCMS, ESI) calcd. for $C_{18}H_{23}N_6O_6SBr$: 533.0 (M+H). Found: 533.0.

EXAMPLE 56

3-(3-Chloro-2-methylphenylsulfonyl)amino-6-methyl-1-[(2-guanidinooxyethyl) aminocarbonylmethyl]-2-pyridinone trifluoroacetate

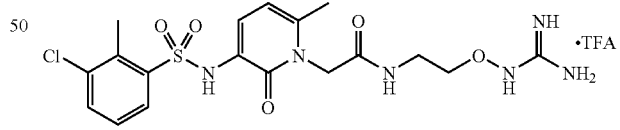

The title compound was prepared as in Example 35 starting with 3-chloro-2-methylbenzenesulfonyl chloride (0.023 g, 0.10 mmol). $^1$H NMR (300 MHz, DMSO-$d_6$) δ 10.89 (s, 1H), 9.65 (s, 1H), 8.43 (t, 1H, J=5.5 Hz), 7.81 (dd, 1H, J=7.9 Hz, 0.8 Hz), 7.69 (m, 5H), 7.33 (t, 1H, J=8.0 Hz), 7.23 (d, 1H, J=7.6 Hz), 6.08 (d, 1H, J=7.7 Hz), 4.61 (s, 2H), 3.80 (t, 2H, J=5.3 Hz), 3.36 (m, 2H), 2.65 (s, 3H), 2.19 (s, 3H). Mass spectrum (LCMS, ESI) calcd. for $C_{18}H_{23}N_6O_5SCl$: 471.0 (M+H). Found: 471.1.

EXAMPLE 57

3-(2-Chloro-5-trifluoromethylphenylsulfonyl)amino-6-methyl-1-[(2-guanidinooxyethyl)aminocarbonylmethyl]-2-pyridinone trifluoroacetate

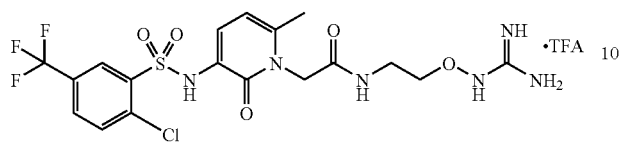

The title compound was prepared as in Example 35 starting with 2-chloro-5-(trifluoromethyl)benzenesulfonyl chloride (0.027 g, 0.10 mmol). $^1$H NMR (300 MHz, DMSO-d$_6$) δ 10.89 (s, 1H), 9.90 (s, 1H), 8.43 (t, 1H, J=5.5 Hz), 8.31 (d, 1H, J=1.8 Hz), 8.01 (dd, 1H, J=8.5 Hz, 2.0 Hz), 7.90 (d, 1H, J=8.3 Hz), 7.69 (br s, 4H), 7.32 (d, 1H, J=7.6 Hz), 6.13 (d, 1H, J=7.8 Hz), 4.64 (s, 2H), 3.79 (t, 2H, J=5.4 Hz), 3.35 (m, 2H), 2.22 (s, 3H). Mass spectrum (LCMS, ESI) calcd. for C$_{18}$H$_{20}$N$_6$O$_5$SClF$_3$: 525.0 (M+H). Found: 525.1.

EXAMPLE 58

3-(2,4-Dichlorophenylsulfonyl)amino-6-methyl-1-[(2-guanidinooxyethyl) aminocarbonylmethyl]-2-pyridinone trifluoroacetate

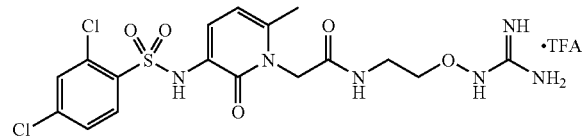

The title compound was prepared as in Example 35 starting with 0.2,4-dichlorobenzenesulfonyl chloride (0.025 g, 0.10 mmol). $^1$H NMR (300 MHz, DMSO-d$_6$) δ 10.89 (s, 1H), 9.46 (s, 1H), 8.43 (t, 1H, J=5.5 Hz), 7.96 (d, 1H, J=8.6 Hz), 7.86 (d, 1H, J=2.1 Hz), 7.69 (br s, 4H), 7.57 (dd, 1H, J=8.6 Hz, 2.1 Hz), 7.23 (d, 1H, J=7.6 Hz), 6.10 (d, 1H, J=7.7 Hz), 4.62 (s, 2H), 3.80 (t, 2H, J=5.2 Hz), 3.37 (m, 2H), 2.21 (s, 3H). Mass spectrum (LCMS, ESI) calcd. for C$_{17}$H$_{20}$N$_6$O$_5$SCl$_2$: 491.4 (M). Found: 491.1.

EXAMPLE 59

3-(4-Vinylphenylsulfonyl)amino-6-methyl-1-[(2-guanidinooxyethyl) aminocarbonylmethyl]-2-pyridinone trifluoroacetate

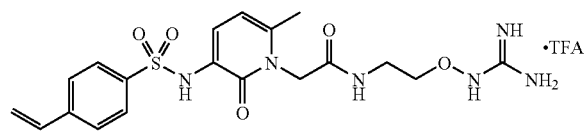

The title compound was prepared as in Example 35 starting with p-styrenesulfonyl chloride (0.021 g, 0.11 mmol). $^1$H NMR (300 MHz, DMSO-d$_6$) δ 10.92 (s, 1H), 9.34 (s, 1H), 8.42 (t, 1H, J=5.4 Hz), 7.79 (d, 2H, J=8.4 Hz), 7.71 (br s, 4H), 7.62 (d, 2H, J=8.4 Hz), 7.26 (d, 1H, J=7.6 Hz), 6.78 (dd, 1H, J=17.7 Hz, 11.0 Hz), 6.09 (d, 1H, J=7.7 Hz), 5.99 (d, 1H, J=17.6 Hz), 5.44 (d, 1H, J=11.1 Hz), 4.60 (s, 2H), 3.78 (t, 2H, J=5.2 Hz), 3.35 (m, 2H), 2.19 (s, 3H). Mass spectrum (LCMS, ESI) calcd. for C$_{19}$H$_{24}$N$_6$O$_5$S: 449.6 (M+H). Found: 449.2.

EXAMPLE 60

3-(2-Butoxy-S-(1,1-dimethylpropyl)phenylsulfonyl)amino-6-methyl-1-[(2-guanidinooxyethyl)aminocarbonylmethyl]-2-pyridinone trifluoroacetate

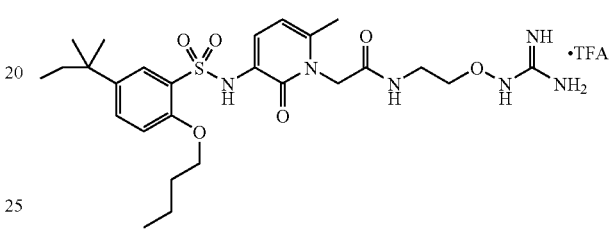

The title compound was prepared as in Example 35 starting with 2-(n-butoxy)-5-(2'-isopentyl)benzenesulfonyl chloride (0.033 g, 0.10 mmol). $^1$H NMR (300 MHz, DMSO-d$_6$) δ 10.88 (brd s, 1H), 8.44 (br s, 1H), 8.11 (s, 1H), 7.68 (m, 5H), 7.53 (dd, 1H, J=8.7 Hz, 2.4 Hz), 7.16 (d, 1H, J=7.6 Hz), 7.10 (d, 1H, J=8.8 Hz), 6.03 (d, 1H, J=7.8 Hz), 4.66 (s, 2H), 4.01 (t, 2H, J=6.4 Hz), 3.80 (t, 2H, J=5.2 Hz), 3.39 (m, 2H), 2.14 (s, 3H), 1.76 (m, 2H), 1.57 (m, 2H), 1.47 (m, 2H), 1.22 (s, 6H), 0.94 (t, 3H, J=7.4 Hz), 0.55 (t, 3H, J=7.3 Hz). Mass spectrum (LCMS, ESI) calcd. for C$_{26}$H$_{40}$N$_6$O$_6$S: 565.8 (M+H). Found: 565.2.

EXAMPLE 61

3-(3-Nitrophenylsulfonyl)amino-6-methyl-1-[(2-guanidinooxyethyl) aminocarbonylmethyl]-2-pyridinone trifluoroacetate

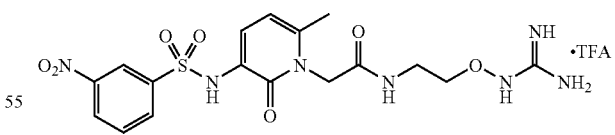

The title compound was prepared as in Example 35 starting with 3-nitrobenzenesulfonyl chloride (0.022 g, 0.10 mmol). $^1$H NMR (300 MHz, DMSO-d$_6$) δ 10.81 (br s, 1H), 9.85 (br s, 1H), 8.56 (t, 1H, J=1.9 Hz), 8.43 (dd, 1H, J=8.3 Hz, 1.4 Hz), 8.34 (m, 1H), 8.18 (d, 1H, J=8.2 Hz), 7.81 (t, 1H, J=8.0 Hz), 7.60 (br s, 4H), 7.34 (d, 1H, J=7.6 Hz), 6.13 (d, 1H, J=7.7 Hz), 4.55 (s, 2H), 3.77 (m, 2H), 3.38 (m, 2H), 2.20 (s, 3H). Mass spectrum (LCMS, ESI) calcd. for C$_{17}$H$_{21}$N$_7$O$_7$S: 468.2 (M+H). Found: 469.2.

EXAMPLE 62

3-(4-Chloro-3-nitrophenylsulfonyl)amino-6-methyl-1-[(2-guanidinooxyethyl) aminocarbonylmethyl]-2-pyridinone trifluoroacetate

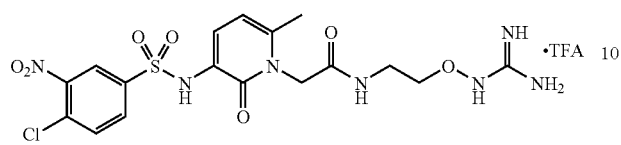

The title compound was prepared as in Example 35 starting with 4-chloro-3-nitrobenzenesulfonyl chloride (0.026 g, 0.10 mmol). $^1$H NMR (300 MHz, DMSO-$d_6$) δ 10.90 (br s, 1H), 9.92 (br s, 1H), 8.44 (d, 1H, J=2.1 Hz), 8.38 (t, 1H, J=5.6 Hz), 8.02 (dd, 1H, J=8.5 Hz, 2.1 Hz), 7.92 (d, 1H, J=8.5 Hz), 7.68 (br s, 4H), 7.36 (d, 1H, J=7.5 Hz), 6.15 (d, 1H, J=7.9 Hz), 4.58 (br s, 2H), 3.79 (t, 2H, J=5.4 Hz), 3.38 (m, 2H), 2.22 (s, 3H). Mass spectrum (LCMS, ESI) calcd. for $C_{17}H_{20}N_7O_7SCl$: 502.0 (M+H). Found: 502.1.

EXAMPLE 63

3-(4-Methylcarbonylaminophenylsulfonyl)amino-6-methyl-1-[(2-guanidinooxyethyl)aminocarbonylmethyl]-2-pyridinone trifluoroacetate

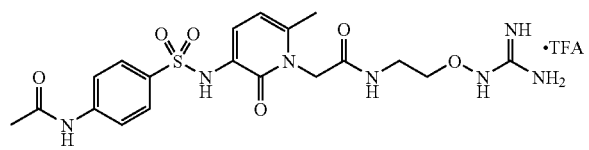

The title compound was prepared as in Example 35 starting with 4-(acetylamino)benzenesulfonyl chloride (0.023 g, 0.10 mmol). $^1$H NMR (300 MHz, DMSO-$d_6$) δ 10.86 (br s, 1H), 10.32 (s, 1H), 9.13 (s, 1H), 8.41 (t, 1H, J=5.5 Hz), 7.76 (d, 2H, J=8.9 Hz), 7.69 (d, 2H, J=9.0 Hz), 7.63 (br s, 4H), 7.23 (d, 1H, J=7.6 Hz), 6.08 (d, 1H, J=8.1 Hz), 4.61 (s, 2H), 3.79 (t, 2H, 3=5.4 Hz), 3.39 (m, 2H), 2.19 (s, 3H), 2.07 (s, 3H). Mass spectrum (LCMS, ESI) calcd. for $C_{19}H_{25}N_7O_6S$: 480.2 (M+H). Found: 480.2.

EXAMPLE 64

3-(4-tert-Butylphenylsulfonyl)amino-6-methyl-1-[(2-guanidinooxyethyl) aminocarbonylmethyl]-2-pyridinone trifluoroacetate

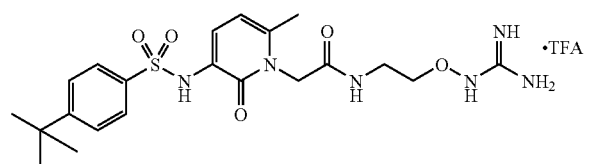

The title compound was prepared as in Example 35 starting with 4-(tert-butyl)benzenesulfonyl chloride (0.023 g, 0.10 mmol). $^1$H NMR (300 MHz, DMSO-$d_6$) δ 10.85 (s, 1H), 9.27 (s, 1H), 8.43 (t, 1H, J=5.4 Hz), 7.79 (d, 2H, 8.5 Hz), 7.65 (br s, 4H), 7.56 (d, 2H, J=8.6 Hz), 7.25 (d, 1H, J=7.6 Hz), 6.09 (d, 1H, J=7.9 Hz), 4.62 (s, 2H), 3.79 (t, 2H, J=5.3 Hz), 3.40 (m, 2H), 2.19 (s, 3H), 1.28 (s, 9H). Mass spectrum (LCMS, ESI) calcd. for $C_{21}H_{30}N_6O_5S$: 479.3 (M+H). Found: 479.2.

EXAMPLE 65

3-(4-Trifluoromethylphenylsulfonyl)amino-6-methyl-1-[(2-guanidinooxyethyl) aminocarbonylmethyl]-2-pyridinone trifluoroacetate

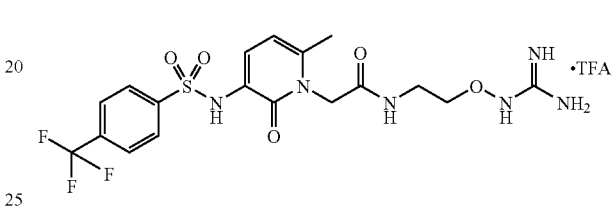

The title compound was prepared as in Example 35 starting with 4-(trifluoromethyl)benzenesulfonyl chloride (0.025 g, 0.10 mmol). $^1$H NMR (300 MHz, DMSO-$d_6$) δ 10.92 (s, 1H), 9.73 (s, 1H), 8.40 (t, 1H, J=5.5 Hz), 8.01 (d, 2H, J=8.2 Hz), 7.91 (d, 2H, J=8.5 Hz), 7.69 (br s, 4H), 7.31 (d, 1H, J=7.5 Hz), 6.12 (d, 1H, J=8.0 Hz), 4.59 (s, 2H), 3.78 (t, 2H, J=5.3 Hz), 2.20 (s, 3H). Mass spectrum (LCMS, ESI) calcd. for $C_{18}H_{21}N_6O_5SF_3$: 491.2 (M+H). Found: 491.2.

EXAMPLE 66

3-(3-Cyanophenylsulfonyl)amino-6-methyl-1-[(2-guanidinooxyethyl) aminocarbonylmethyl]-2-pyridinone trifluoroacetate

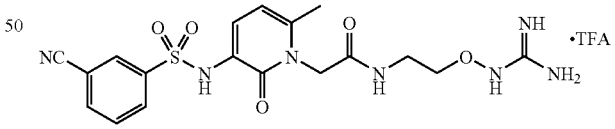

The title compound was prepared as in Example 35 starting with 3-cyanobenzenesulfonyl chloride (0.020 g, 0.10 mmol). $^1$H NMR (300 MHz, DMSO-$d_6$) δ 10.91 (br s, 1H), 9.73 (br s, 1H), 8.40 (t, 1H, J=5.6 Hz), 8.27 (t, 1H, J=1.6 Hz), 8.09 (dd, 1H, J=7.9 Hz, 1.6 Hz), 7.72 (m, 5H), 7.33 (d, 1H, J=7.5 Hz), 6.12 (d, 1H, J=7.6 Hz), 4.59 (s, 2H), 4.10 (br s, 2H), 3.79 (t, 2H, J=5.3 Hz), 3.38 (m, 2H), 2.21 (s, 3H). Mass spectrum (LCMS, ESI) calcd. for $C_{18}H_{21}N_7O_5S$: 448.2 (M+H). Found: 449.2.

EXAMPLE 67

3-(4-Methylsulfonylphenylsulfonyl)amino-6-methyl-1-[(2-guanidinooxyethyl) aminocarbonylmethyl]-2-pyridinone trifluoroacetate

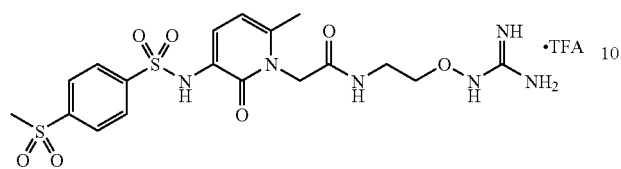

The title compound was prepared as in Example 35 starting with 4-(methylsulfonyl)benzenesulfonyl chloride (0.024 g, 0.10 mmol). $^1$H NMR (300 MHz, DMSO-d$_6$) δ 10.87 (s, 1H), 9.78 (s, 1H), 8.40 (t, 1H, J=5.4 Hz), 8.06 (s, 4H), 7.66 (br s, 4H), 7.32 (d, 1H, J=7.5 Hz), 6.12 (d, 1H, J=7.8 Hz), 4.59 (s, 2H), 3.78 (t, 2H, J=5.2 Hz), 3.40 (m, 2H), 3.28 (s, 3H), 2.20 (s, 3H). Mass spectrum (LCMS, ESI) calcd. for $C_{18}H_{24}N_6O_7S_2$: 501.2 (M+H). Found: 501.1.

EXAMPLE 68

3-Dansylamino-6-methyl-1-[(2-guanidinooxyethyl) aminocarbonylmethyl]-2-pyridinone trifluoroacetate

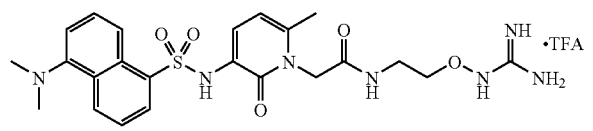

The title compound was prepared as in Example 35 starting with dansyl chloride (0.027 g, 0.10 mmol). $^1$H NMR (300 MHz, DMSO-d$_6$) δ 10.98 (s, 1H), 9.66 (s, 1H), 8.39 (m, 3H), 8.20 (d, 1H, J=7.3 Hz), 7.75 (br s, 4H), 7.58 (m, 2H), 7.25 (d, 1H, J=7.6 Hz), 7.16 (d, 1H, J=7.6 Hz), 6.04 (d, 1H, J=7.7 Hz), 4.59 (s, 2H), 3.79 (t, 2H, J=5.1 Hz), 3.35 (m, 2H), 2.82 (s, 6H), 2.15 (s, 3H). Mass spectrum (LCMS, ESI) calcd. for $C_{23}H_{29}N_7O_5S$: 516.7 (M+H). Found: 516.2.

EXAMPLE 69

3-(Pentafluorophenylsulfonyl)amino-6-methyl-1-[(2-guanidinooxyethyl) aminocarbonylmethyl]-2-pyridinone trifluoroacetate

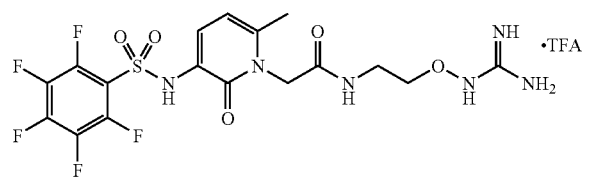

The title compound was prepared as in Example 35 starting with pentafluorobenzenesulfonyl chloride (0.028 g, 0.11 mmol). $^1$H NMR (300 MHz, CD$_3$OD) δ 7.55 (d, 1H, J=7.6 Hz), 6.27 (d, 1H, J=7.6 Hz), 4.68 (s, 2H), 3.94 (t, 2H, J=5.0 Hz), 3.48 (t, 2H, J=5.0 Hz), 2.33 (s, 3H). Mass spectrum (LCMS, ESI) calcd. for $C_{16}H_{17}N_6O_5SF_5$: 513.5 (M+H). Found: 513.1.

EXAMPLE 70

3-(2,5-Dichlorophenylsulfonyl)amino-6-methyl-1-[(2-guanidinooxyethyl) aminocarbonylmethyl]-2-pyridinone trifluoroacetate

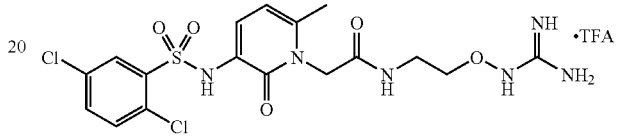

The title compound was prepared as in Example 35 starting with 2,5-dichlorobenzenesulfonyl chloride (0.025 g, 0.10 mmol). $^1$H NMR (300 MHz, DMSO-d$_6$) δ 10.89 (s, 1H), 9.68 (s, 1H), 8.44 (t, 1H, J=5.5 Hz), 8.03 (d, 1H, J=2.1 Hz), 7.70 (m, 6H), 7.29 (d, 1H, J=7.6 Hz), 6.13 (d, 1H, J=7.9 Hz), 4.65 (s, 2H), 3.80 (t, 2H, J=5.2 Hz), 3.39 (m, 2H), 2.22 (s, 3H). Mass spectrum (LCMS, ESI) calcd. for $C_{17}H_{20}N_6O_5SCl_2$: 491.0 (M+H). Found: 491.1.

EXAMPLE 71

3-(4-Nitrophenylsulfonyl)amino-6-methyl-1-[(2-guanidinooxyethyl) aminocarbonylmethyl]-2-pyridinone trifluoroacetate

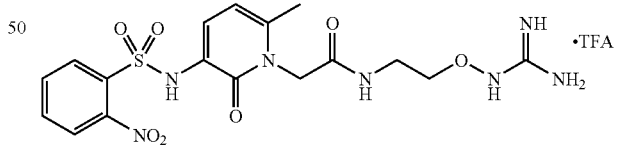

The title compound was prepared as in Example 35 starting with 2-nitrobenzenesulfonyl chloride (0.023 g, 0.10 mmol). $^1$H NMR (300 MHz, CD$_3$OD) δ 8.00 (dd, 1H, J=7.6 Hz, 1.7 Hz), 7.91 (dd, 1H, J=7.8 Hz, 1.4 Hz), 7.77 (m, 2H), 7.59 (d, 1H, J=7.6 Hz), 6.26 (dd, 1H, J=7.7 Hz, 0.8 Hz), 4.70 (s, 2H), 3.92 (t, 2H, J=5.2 Hz), 3.48 (t, 2H, J=5.2 Hz), 2.31 (s, 3H). Mass spectrum (LCMS, ESI) calcd. for $C_{17}H_{21}N_7O_7S$: 468.5 (M+H). Found: 468.1.

EXAMPLE 72

3-Di(4-nitrophenylsulfonyl)amino-6-methyl 1-[(2-guanidinooxyethyl) aminocarbonylmethyl]-2-pyridinone trifluoroacetate

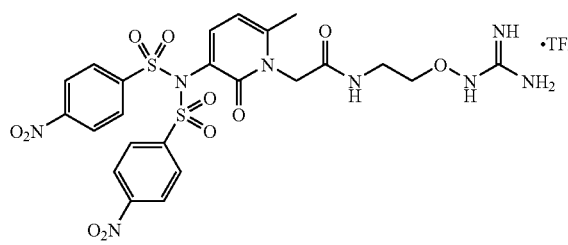

The title compound was prepared as in Example 35 starting with 4-nitrobenzenesulfonyl chloride (0.022 g, 0.10 mmol). $^1$H NMR (300 MHz, DMSO-$d_6$) δ 11.17 (s, 1H), 8.43 (d, 4H, J=8.9 Hz), 8.12 (d, 4H, J=8.9 Hz), 7.84 (m, 4H), 7.60 (d, 1H, J=7.6 Hz), 6.34 (d, 1H, J=7.8 Hz), 4.63 (s, 2H), 3.82 (m, 2H), 3.38 (m, 2H), 2.29 (s, 3H). Mass spectrum (LCMS, ESI) calcd. for $C_{23}H_{24}N_8O_{11}S_2$: 653.6 (M+H). Found: 653.1.

EXAMPLE 73

3-(2,5-Dimethoxyphenylsulfonyl)amino-6-methyl-1-[(2-guanidinooxyethyl) aminocarbonylmethyl]-2-pyridinone trifluoroacetate

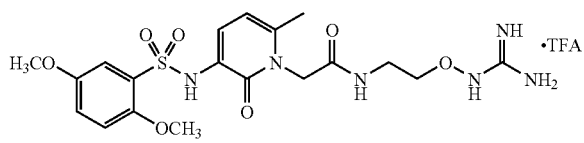

The title compound was prepared as in Example 35 starting with 2,5-dimethoxybenzenesulfonyl chloride (0.023 g, 0.10 mmol). $^1$H NMR (300 MHz, CD$_3$OD) δ 7.38 (d, 1H, J=7.7 Hz), 7.35 (d, 1H, J=2.8 Hz), 7.12 (dd, 1H, J=9.0 Hz, 2.8 Hz), 7.04 (d, 1H, J=9.0 Hz), 6.13 (d, 1H, J=7.7 Hz), 4.73 (s, 2H), 3.95 (t, 2H, J=5.0 Hz), 3.83 (s, 3H), 3.76 (s, 3H), 3.50 (t, 2H, J=5.1 Hz), 2.26 (s, 3H). Mass spectrum (LCMS, ESI) calcd. for $C_{19}H_{26}N_6O_7S$: 483.6 (M+H). Found: 483.1.

EXAMPLE 74

3-(4-Propylphenylsulfonyl)amino-6-methyl-1-[(2-guanidinooxyethyl) aminocarbonylmethyl]-2-pyridinone trifluoroacetate

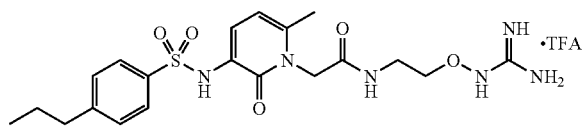

The title compound was prepared as in Example 35 starting with 4-n-propylbenzenesulfonyl chloride (0.022 g, 0.10 mmol). $^1$H NMR (300 MHz, CD$_3$OD) δ 7.70 (m, 2H), 7.47 (d, 1H, J=7.6 Hz), 7.30 (d, 2H, J=7.9 Hz), 6.19 (d, 1H, J=7.7 Hz), 4.70 (s, 2H), 3.93 (t, 2H, J=5.0 Hz), 3.48 (t, 2H, J=5.0 Hz), 2.63 (t, 2H, J=7.6 Hz), 2.29 (s, 3H), 1.63 (sextet, 2H, J=7.5 Hz), 0.92 (t, 3H, J=7.3 Hz). Mass spectrum (LCMS, ESI) calcd. for $C_{20}H_{28}N_6O_5S$: 465.6 (M+H). Found: 465.2.

EXAMPLE 75

3-(2-Methyl-5-nitrophenylsulfonyl)amino-6-methyl-1-[(2-guanidinooxyethyl)aminocarbonylmethyl]-2-pyridinone trifluoroacetate

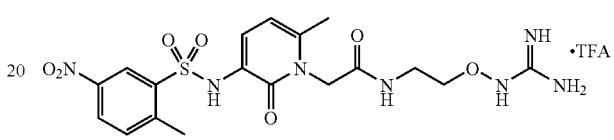

The title compound was prepared as in Example 35 starting with 2-methyl-5-nitrobenzenesulfonyl chloride (0.024 g, 0.10 mmol). $^1$H NMR (300 MHz, DMSO-$d_6$) δ 11.04 (s, 1H), 9.87 (s, 1H), 8.45 (d, 1H, J=2.5 Hz), 8.38 (t, 1H, J=5.5 Hz), 8.30 (dd, 1H, J=8.4 Hz, 2.5 Hz), 7.77 (br s, 4H), 7.65 (d, 1H, J=8.5 Hz), 7.32 (d, 1H, J=7.5 Hz), 6.12 (d, 1H, J=7.6 Hz), 4.55 (s, 2H), 3.78 (t, 2H, J=5.3 Hz), 3.32 (m, 2H), 2.75 (s, 3H), 2.19 (s, 3H). Mass spectrum (LCMS, ESI) calcd. for $C_{18}H_{23}N_7O_7S$: 482.5 (M+H). Found: 482.1.

EXAMPLE 76

3-(2-trifluoromethylphenylsulfonyl)amino-6-methyl-1-[(2-guanidinooxyethyl) aminocarbonylmethyl]-2-pyridinone trifluoroacetate

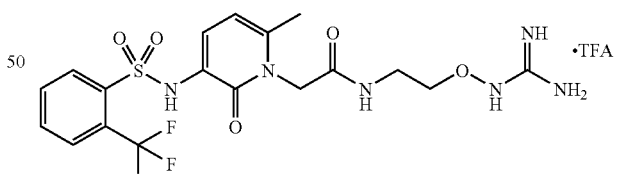

The title compound was prepared as in Example 35 starting with 2-(trifluoromethyl)benzenesulfonyl chloride (0.025 g, 0.10 mmol). $^1$H NMR (300 MHz, DMSO-$d_6$) δ 10.95 (s, 1H), 9.50 (s, 1H), 8.45 (t, 1H, J=5.4 Hz), 8.15 (m, 1H), 7.98 (m, 1H), 7.80 (m, 2H), 7.73 (br s, 4H), 7.28 (d, 1H, J=7.6 Hz), 6.12 (d, 1H, J=7.7 Hz), 4.63 (s, 2H), 3.80 (t, 2H, J=5.2 Hz), 3.36 (m, 2H), 2.21 (s, 3H). Mass spectrum (LCMS, ESI) calcd. for $C_{18}H_{21}N_6O_5SF_3$: 491.5 (M+H). Found: 491.1.

EXAMPLE 77

3-(2,3-Dichlorophenylsulfonyl)amino-6-methyl-1-[(2-guanidinooxyethyl) aminocarbonylmethyl]-2-pyridinone trifluoroacetate

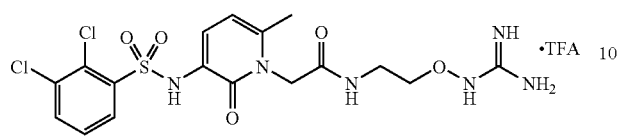

The title compound was prepared as in Example 35 starting with 2,3-dichlorobenzenesulfonyl chloride (0.023 g, 0.09 mmol). $^1$H NMR (300 MHz, DMSO-$d_6$) δ 11.02 (s, 1H), 9.58 (s, 1H), 8.45 (t, 1H, J=. 5.5 Hz), 7.97 (dd, 1H, J=8.0 Hz, 1.3 Hz), 7.91 (dd, 1H, J=8.1 Hz, 1.3 Hz), 7.77 (br s, 4H), 7.50 (t, 1H, J=8.0 Hz), 7.24 (d, 1H, J=7.5 Hz), 6.10 (d, 1H, J=7.7 Hz), 4.63 (s, 2H), 3.80 (t, 2H, J=5.2 Hz), 3.36 (m, 2H), 2.21 (s, 3H). Mass spectrum (LCMS, ESI) calcd. for $C_{17}H_{20}N_6O_5SCl_2$: 491.0 (M+H). Found: 491.1.

EXAMPLE 78

3-(2-Trifluoromethoxyphenylsulfonyl)amino-6-methyl-1-[(2-guanidinooxyethyl)aminocarbonylmethyl]-2-pyridinone trifluoroacetate

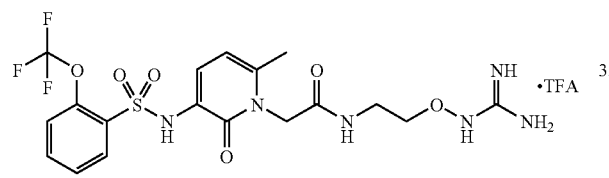

The title compound was prepared as in Example 35 starting with 2-(trifluoromethoxy)benzenesulfonyl chloride (0.025 g, 0.10 mmol). $^1$H NMR (300 MHz, DMSO-$d_6$) δ 10.93 (s, 1H), 9.31 (s, 1H), 8.44 (t, 1H, J=5.5 Hz), 7.98 (dd, 1H, J=7.9 Hz, 1.6 Hz), 7.75 (m, 5H), 7.51 (m, 2H), 7.26 (d, 1H, J=7.5 Hz), 6.11 (d, 1H, J=7.7 Hz), 4.63 (s, 2H), 3.80 (t, 2H, J=5.3 Hz), 3.36 (m, 2H), 2.21 (s, 3H). Mass spectrum (LCMS, ESI) calcd. for $C_{18}H_{21}N_6O_6SF_3$: 507.5 (M+H). Found: 507.1.

EXAMPLE 79

3-(4-(3-Chloro-2-cyanophenoxy)phenylsulfonyl)amino-6-methyl-1-[(2-guanidinooxyethyl)aminocarbonylmethyl]-2-pyridinone trifluoroacetate

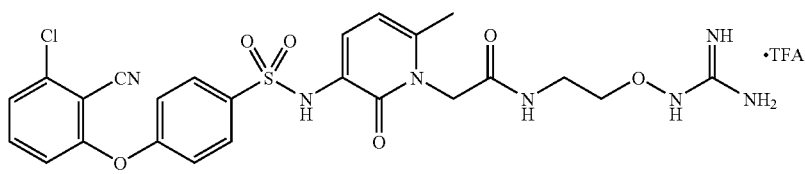

The title compound was prepared as in Example 35 starting with 4-(3-chloro-2-cyanophenoxy)benzenesulfonyl chloride (0.032 g, 0.10 mmol). $^1$H NMR (300 MHz, DMSO-$d_6$) δ 10.95 (s, 1H), 9.43 (s, 1H), 8.43 (t, 1H, J=5.3 Hz), 7.89 (d, 2H, J=8.7 Hz), 7.72 (m, 5H), 7.57 (d, 1H, J=8.1 Hz), 7.30 (m, 3H), 7.11 (d, 1H, J=8.4 Hz), 6.11 (d, 1H, J=7.7 Hz), 4.61 (s, 2H), 3.79 (t, 2H, J=5.0 Hz), 3.34 (m, 2H), 2.20 (s, 3H). Mass spectrum (LCMS, ESI) calcd. for $C_{24}H_{24}N_7O_6SCl$: 574.0 (M+H). Found: 574.1.

EXAMPLE 80

3-(2-Chloro-4-fluorophenylsulfonyl)amino-6-methyl-1-[(2-guanidinooxy ethyl) aminocarbonylmethyl]-2-pyridinone trifluoroacetate

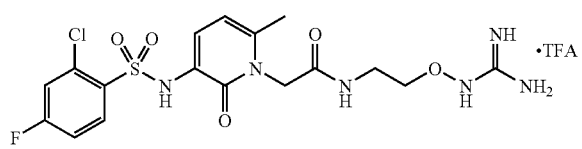

The title compound was prepared as in Example 35 starting with 2-chloro-4-fluorobenzenesulfonyl chloride (0.023 g, 0.10 mmol). $^1$H NMR (300 MHz, DMSO-$d_6$) δ 10.92 (m, 1H), 9.34 (s, 1H), 8.44 (t, 1H, J=5.5 Hz), 8.04 (dd, 1H, J=8.9 Hz, 5.9 Hz), 7.69 (m, 5H), 7.36 (m, 1H), 7.23 (d, 1H, J=7.6 Hz), 6.10 (d, 1H, J=7.7 Hz), 4.63 (s, 2H), 3.80 (t, 2H, J=5.0 Hz), 3.37 (m, 2H), 2.20 (s, 3H). Mass spectrum (LCMS, ESI) calcd. for $C_{17}H_{20}N_6O_5ClF$: 475.0 (M+H). Found: 475.1.

EXAMPLE 81

3-(5-Chloro-2-methoxyphenylsulfonyl)amino-6-methyl-1-[(2-guanidinooxyethyl)aminocarbonylmethyl]-2-pyridinone trifluoroacetate

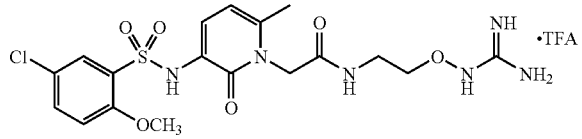

The title compound was prepared as in Example 35 starting with 5-chloro-2-methoxybenzenesulfonyl chloride (0.025 g, 0.11 mmol). $^1$H NMR (300 MHz, DMSO-$d_6$) δ 10.89 (s, 1H), 8.67 (s, 1H), 8.44 (t, 1H, J=5.4 Hz), 7.68 (m, 6H), 7.23 (m, 2H), 6.10 (d, 1H, J=7.8 Hz), 4.65 (s, 2H), 3.79 (m, 5H), 3.38

(m, 2H), 2.19 (s, 3H). Mass spectrum (LCMS, ESI) calcd. for $C_{18}H_{23}N_6O_6SCl$: 487.0 (M+H). Found: 487.1.

EXAMPLE 82

3-(2-Methoxy-5-methylphenylsulfonyl)amino-6-methyl-1-[(2-guanidinooxyethyl)aminocarbonylmethyl]-2-pyridinone trifluoroacetate

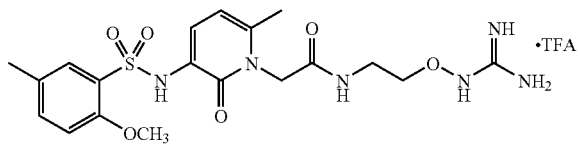

The title compound was prepared as in Example 35 starting with 2-methoxy-5-methylbenzenesulfonyl chloride (0.023 g, 0.11 mmol). $^1$H NMR (300 MHz, DMSO-$d_6$) δ 10.88 (s, 1H), 8.45 (t, 1H, J=5.5 Hz), 8.29 (s, 1H), 7.68 (br s, 4H), 7.58 (d, 1H, J=1.9 Hz), 7.40 (dd, 1H, J=8.5 Hz, 1.9 Hz), 7.20 (d, 1H, J=7.6 Hz), 7.07 (d, 1H, J=8.5 Hz), 7.16 (d, 1H, J=8.9 Hz), 6.07 (d, 1H, J=7.7 Hz), 4.65 (s, 2H), 3.80 (m, 5H), 3.39 (m, 2H), 2.27 (s, 3H), 2.17 (s, 3H). Mass spectrum (LCMS, ESI) calcd. for $C_{19}H_{26}N_6O_6S$: 467.6 (M+H). Found: 467.1.

EXAMPLE 83

3-(4-Phenylphenylsulfonyl)amino-6-methyl-1-[(2-guanidinooxyethyl) aminocarbonylmethyl]-2-pyridinone trifluoroacetate

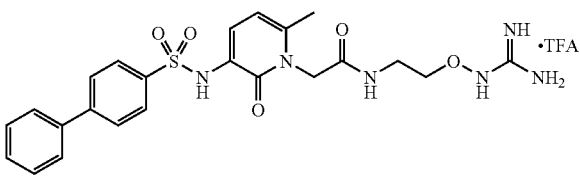

The title compound was prepared as in Example 35 starting with 4-phenylbenzenesulfonyl chloride (0.026 g, 0.10 mmol). $^1$H NMR (300 MHz, DMSO-$d_6$) δ 10.90 (s, 1H), 9.41 (s, 1H), 8.42 (t, 1H, J=5.4 Hz), 7.91 (d, 2H, J=8.5 Hz), 7.83 (d, 2H, J=8.5 Hz), 7.71 (m, 6H), 7.46 (m, 3H), 7.31 (d, 1H, J=7.6 Hz), 6.11 (d, 1H, J=7.7 Hz), 4.61 (s, 2H), 3.76 (t, 2H, J=5.0 Hz), 3.37 (m, 2H), 2.19 (s, 3H). Mass spectrum (LCMS, ESI) calcd. for $C_{23}H_{26}N_6O_5S$: 499.6 (M+H). Found: 499.2.

EXAMPLE 84

3-(5-Chlorothiophene-2-sulfonyl)amino-6-methyl-1-[(2-guanidinooxyethyl)aminocarbonylmethyl]-2-pyridinone trifluoroacetate

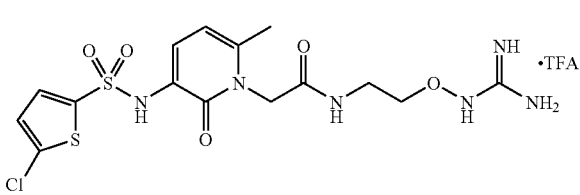

The title compound was prepared as in Example 35 starting with 5-chlorothiophene-2-sulfonyl chloride (0.023 g, 0.11 mmol). $^1$H NMR (300 MHz, DMSO-$d_6$) δ 10.93 (s, 1H), 9.76 (s, 1H), 8.44 (t, 1H, J=5.5 Hz), 7.67 (br s, 4H), 7.46 (d, 1H, J=4.1 Hz), 7.34 (d, 1H, J=7.5 Hz), 7.18 (d, 1H, J=4.1 Hz), 6.16 (d, 1H, J=7.7 Hz), 4.64 (s, 2H), 3.80 (t, 2H, J=5.2 Hz), 3.38 (m, 2H), 2.24 (s, 3H). Mass spectrum (LCMS, ESI) calcd. for $C_{15}H_{19}N_6O_5S_2Cl$: 463.0 (M+H). Found: 463.1.

EXAMPLE 85

3-(6-Chloronaphthalene-2-sulfonyl)amino-6-methyl-1-[(2-guanidinooxyethyl)aminocarbonylmethyl]-2-pyridinone trifluoroacetate

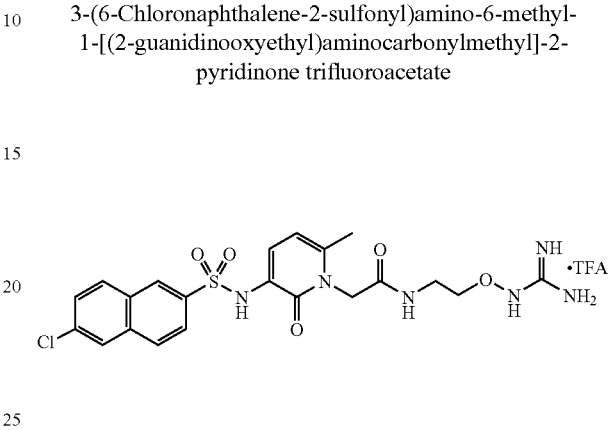

The title compound was prepared as in Example 35 starting with 2-(6-chloro)naphthalenesulfonyl chloride (0.026 g, 0.10 mmol). $^1$H NMR (300 MHz, DMSO-$d_6$) δ 10.87 (s, 1H), 9.53 (s, 1H), 8.53 (s, 1H), 8.38 (t, 1H, J=5.5 Hz), 8.17 (m, 2H), 8.05 (d, 1H, J=8.8 Hz), 7.91 (dd, 1H, J=8.7 Hz, 1.8 Hz), 7.68 (m, 5H), 7.32 (d, 1H, J=7.6 Hz), 6.09 (d, 1H, J=7.9 Hz), 4.56 (s, 2H), 3.76 (t, 2H, J=5.2 Hz), 3.36 (m, 2H), 2.17 (s, 3H). Mass spectrum (LCMS, ESI) calcd. for $C_{21}H_{23}N_6O_5SCl$: 507.0 (M+H). Found: 507.1.

EXAMPLE 86

3-(6-Bromonaphthalene-2-sulfonyl)amino-6-methyl-1-[(2-guanidinooxyethyl)aminocarbonylmethyl]-2-pyridinone trifluoroacetate

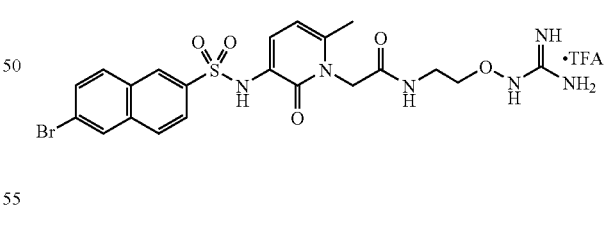

The title compound was prepared as in Example 35 starting with 2-(6-bromo)naphthalenesulfonyl chloride (0.033 g, 0.11 mmol). $^1$H NMR (300 MHz, DMSO-$d_6$) δ 10.85 (s, 1H), 9.53 (s, 1H), 8.52 (s, 1H), 8.38 (t, 1H, J=5.4 Hz), 8.33 (s, 1H), 8.11 (d, 1H, J=8.8 Hz), 8.04 (d, 1H, J=8.8 Hz), 7.90 (dd, 1H, J=8.7 Hz, 1.6 Hz), 7.79 (dd, 1H, J=8.8 Hz, 1.8 Hz), 7.66 (br s, 4H), 7.32 (d, 1H, J=7.6 Hz), 6.08 (d, 1H, J=7.7 Hz), 4.56 (s, 2H), 3.76 (t, 2H, J=5.2 Hz), 3.39 (m, 2H), 2.17 (s, 3H). Mass spectrum (LCMS, ESI) calcd. for $C_{21}H_{23}N_6O_5SBr$: 553.0 (M+H). Found: 553.0.

EXAMPLE 87

3-(3-Bromophenylsulfonyl)amino-6-methyl-1-[(2-guanidinooxyethyl) aminocarbonylmethyl]-2-pyridinone trifluoroacetate

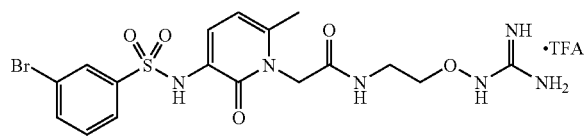

The title compound was prepared as in Example 2 starting with 3-bromobenzenesulfonyl chloride (0.128 g, 0.501 mmol). $^1$H-NMR (300 MHz, CD$_3$OD) δ 7.98 (t, 1H, J=1.8 Hz), 7.75 (m, 2H), 7.50 (d, 1H, J=7.6 Hz), 7.40 (t, 1H, J=8.0 Hz), 6.22 (d, 1H, J=7.6 Hz), 4.69 (s, 2H), 3.93 (t, 2H, J=5.2 Hz), 3.49 (t, 2H, J=5.2 Hz), 2.31 (s, 3H). Mass spectrum (LCMS, ESI) calcd. for C$_{17}$H$_{20}$N$_6$O$_5$SBr: 501.5 (M+H). Found: 501.3.

EXAMPLE 88

3-(Quinoline-8-sulfonyl)amino-6-methyl-1-[(2-guanidinooxyethyl) aminocarbonylmethyl]-2-pyridinone trifluoroacetate

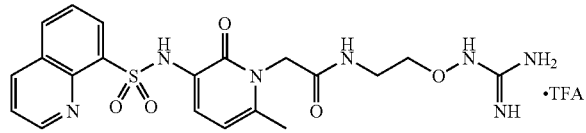

The title compound was prepared in a manner analogous to Example 30. $^1$H-NMR (300 Hz, CD$_3$OD) δ 9.06-9.05 (m, 1H), 8.40-8.37 (m, 2H), 8.16 (d, J=7.0 Hz, 1H), 7.68-7.59 (m. 3H), 6.06 (d, J=7.6 Hz, 1H), 4.57 (s, 2H), 3.71 (t, J=10.5 Hz, 2H), 3.34-3.33 (m, 2H), 2.17 (s, 3H). Mass spectrum (LCMS, ESI) calcd. for C$_{20}$H$_{23}$SO$_5$N$_7$: 474.4 (M+H); Found: 474.3.

EXAMPLE 89

3-(Quinoline-5-sulfonyl)amino-6-methyl-1-[(2-guanidinooxyethyl) aminocarbonylmethyl]-2-pyridinone trifluoroacetate

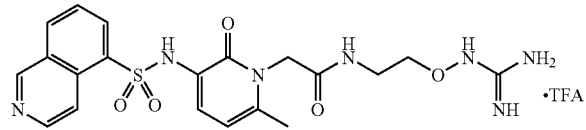

The title compound was prepared in a manner analogous to Example 30. $^1$H-NMR (300 Hz, CD$_3$OD) δ 9.32 (br s, 1H), 8.62-8.30 (m, 4H), 7.73-7.70 (m, 1H), 7.28 (br s, 1H), 6.12 (d, J=6.6 Hz, 1H), 4.62 (s, 2H), 3.64 (br s, 2H), 3.37 (br s, 2H), 2.23 (s, 3H). Mass spectrum (LCMS, ESI) calcd. for C$_{20}$H$_{23}$SO$_5$N$_7$: 474.4 (M+H); Found: 474.3.

EXAMPLE 90

3-(1-Methylimidazole-4-sulfonyl)amino-6-methyl-1-[(2-guanidinooxyethyl) aminocarbonylmethyl]-2-pyridinone trifluoroacetate

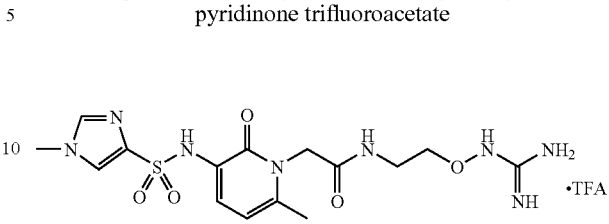

The title compound was prepared in a manner analogous to Example 30. $^1$H-NMR (300 Hz, CD$_3$OD) δ 7.73 (br s, 2H), 7.36 (d, 1H), 6.37-6.35 (m, 2H), 4.89 (s, 2H), 3.86 (bs, 2H), 3.43 (br s, 2H), 3.34 (s, 3H), 2.34 (s, 3H). Mass spectrum (LCMS, ESI) calcd for C$_{15}$H$_{22}$SO$_5$N$_8$: 427.4 (M+H); Found 427.4.

EXAMPLE 91

3-(3-Methylquinoline-8-sulfonyl)amino-6-methyl-1-[(2-guanidinooxyethyl) aminocarbonylmethyl]-2-pyridinone trifluoroacetate

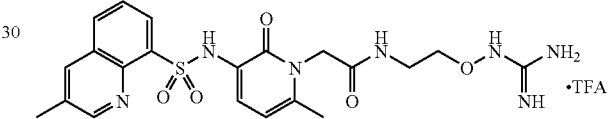

The title compound was prepared in a manner analogous to Example 30. $^1$H-NMR (300 Hz, CD$_3$OD) δ 8.89 (d, J=2.2 Hz, 1H), 8.30 (dd, J=1.3, 7.3 Hz, 1H), 8.17-8.16 (m, 1H), 8.10 (dd, J=1.3, 7.0 Hz, 1H), 7.62 (t, J=7.4 Hz, 1H), 7.50 (d, J=7.6 Hz, 1H), 6.09 (d, J=7.1 Hz, 1H), 4.59 (s, 2H), 3.90 (t, J=5.1 Hz, 2H), 2.55 (s, 3H), 2.19 (S, 3H). Mass spectrum (LCMS, ESI) calcd. for C$_{21}$H$_{26}$SO$_5$N$_7$: 488.5 (M+H); Found 488.5.

EXAMPLE 92

3-(2-Pyridinylsulfonyl)amino-6-methyl-1-[(2-guanidinooxyethyl) aminocarbonylmethyl]-2-pyridinone trifluoroacetate

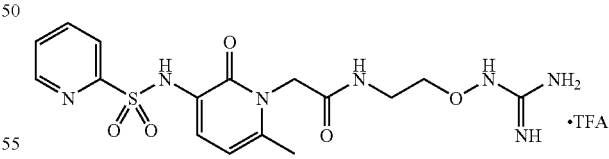

1. 3-(2-Pyridinylsulfonyl)amino-6-methyl-1-{[N,N'-di(tert-butoxycarbonyl)] [2-(guanidinooxyethyl)aminocarbonylmethyl]}-2-pyridinone To a stirred reaction mixture of 2-mercaptopyridine (500 mg, 4.5 mmol) and 1N HCl (5 mL) at 0° C., was bubbled in chlorine gas for 1 hr. The reaction mixture was extracted with methylene chloride (3×50 mL), dried (Na$_2$SO$_4$), and concentrated to yield a clear oil, which was used immediately. N,N-Dimethylaminopyridine (200 mg) is added to a stirred reaction mixture of 2-pyridinesulfonyl chloride (50 mg, 0.178 mmol), and 3-amino-6-methyl-1-{[N,N'-di(tert-butoxycarbonyl)] [3-(guanidinooxyethyl)aminocarbonyl]}-2-pyridinone (78 mg, 0.162 mmol), as prepared in step 3 of Example 30, in methylene chloride (2 mL). Reaction mixture was stirred 16 hrs, concentrated in vacuo and purified on silica gel column chromatrography (4% methanol/96% methylene chloride) to give the title compound as a white solid (34 mg, 30% yield). Mass spectrum (LCMS, ESI) calcd. for $C_{26}H_{37}SO_9N_7$: 624.6 (M+H); Found 624.1.

2. 3-(2-Pyridinylsulfonyl)amino-6-methyl-1-[(2-guanidinooxyethyl) aminocarbonylmethyl]-2-pyridinone trifluoroacetate To a stirred reaction mixture of 3-(2-pyridinylsulfonyl)amino-6-methyl-1-{[N,N'-di(tert-butoxycarbonyl)] [2-(guanidinooxyethyl)aminocarbonylmethyl])}-2-pyridinone (34 mg, 0.055 mmol) in methylene chloride (1 mL) was added trifluoroacetic acid (0.5 mL). The reaction was stirred at ambient temperature for 2 hr, and was purified on a Waters Sep-Pak (2 g) (10% methanol/89% methylene chloride, 1% trifluoroacetic acid), to yield the title compound as a yellow solid (9 mg, 39% yield). $^1$H-NMR (300 Hz, CD$_3$OD) δ 8.92 (s, 1H), 8.70 (br s, 1H), 8.15 (d, J=8.0 Hz, 1H), 7.57-7.49 (m, 2H), 6.23 (d, J=7.6 Hz, 1H), 4.67 (s, 1H), 3.91 (t, J=5.0 Hz, 2H), 3.47 (t, J=5.0 Hz, 2H), 2.30 (s, 3H). Mass spectrum (LCMS, ESI) calcd. for $C_{16}H_{21}SO_5N_7$: 424.4 (M+H); Found 424.1.

EXAMPLE 93

3-(3-Pyridinylsulfonyl)amino-6-methyl-1-[(2-guanidinooxypropyl) aminocarbonylmethyl]-2-pyridinone trifluoroacetate The title compound was prepared in a manner analogous to Example 92. $^1$H-NMR (300 Hz, CD$_3$OD) δ 8.92 (br s, 1H), 8.70 (br s, 1H), 8.16 (d, J=8.0 Hz, 1H), 7.57-7.49 (m, 2H), 6.23 (d, J=7.6 Hz, 1H), 4.67 (s, 2H), 3.9 (t, J=5.0 Hz, 2H), 3.47 (t, J=5.0 Hz, 2H), 2.30 (s, 3H). Mass spectrum (LCMS, ESI) calcd. for $C_{16}H_{21}SO_5N_7$: 424.4 (M+H); Found 424.1.

EXAMPLE 94

3-(4-Ethylphenylsulfonyl)amino-6-methyl-1-[(2-guanidinooxyethyl) aminocarbonylmethyl]-2-pyridinone trifluoroacetate The title compound was prepared as in Example 2 starting with 4-ethylbenzenesulfonyl chloride (0.102 g, 0.498 mmol).

$^1$H NMR (300 MHz, CD$_3$OD) δ 7.71 (d, 2H, J=8.4 Hz), 7.47 (d, 1H, J=7.6 Hz), 7.31 (d, 2H, J=8.4 Hz), 6.19 (dd, 1H, J=7.7 Hz, 0.5 Hz), 4.71 (s, 2H), 3.93 (t, 2H, J=5.1 Hz), 3.48 (t, 2H, J=5.1 Hz), 2.68 (q, 2H, J=7.6 Hz), 2.29 (s, 3H), 1.22 (t, 3H, J=7.6 Hz). Mass spectrum (LCMS, ESI) calcd. for $C_{19}H_{25}N_6O_5S$: 450.5 (M+H). Found: 451.2.

EXAMPLE 95

3-(3-Methylphenylsulfonyl)amino-6-methyl-1-[(2-guanidinooxyethyl)-N-methylaminocarbonylmethyl]-2-pyridinone trifluoroacetate

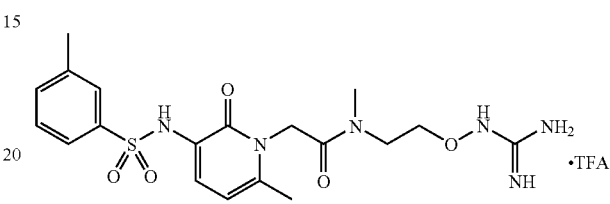

The title compound was prepared from 2-(methylamino)ethanol using the procedures in steps 6-10 of Example 1 and steps 5 & 6 of Example 2. $^1$H-NMR (300 Hz, CD$_3$OD) δ 7.65 (m, 2H), 7.35 (m, 2H), 6.16 (m, 1H), 5.04-5.01 (m, 2H), 3.97-3.92 (m, 2H), 3.69-3.63 (m, 2H) 3.29 (s, 3H), 2.36 (s, 3H). Mass spectrum (LCMS, ESI) calcd. for $C_{19}H_{26}SO_5N_6$: 451.4 (M+H); Found: 451.4.

EXAMPLE 96

3-(3-Methylphenylsulfonyl)amino-6-isopropyl-1-[(2-guanidinooxyethyl) aminocarbonylmethyl]-2-pyridinone hydrochloride

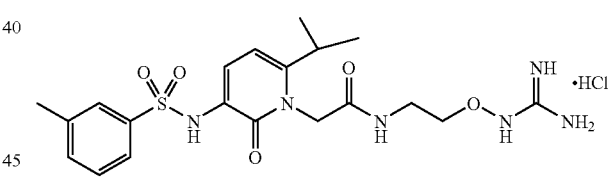

1. 3-Cyano-6-isopropyl-2(1H)-pyridinone

A solution of 3-cyano-6-methyl-2(1H)-pyridinone (10.0 g, 74.6 mmol) in anhydrous tetrahydrofuran (100 mL) was cooled to −78° C. under nitrogen and reacted slowly with lithium diisopropylamide solution (40 mL of 1.4 M and 85 mL of 2.0 M, 226 mmol total) via syringe. After warring to 0° C. and stirring 2 hours, methyl iodide (10 mL, 160 mmol) was added and the reaction stirred 18 hours at ambient temperature. The reaction was poured into 0.67 N NaOH (300 mL), the phases separated, the aqueous layer washed with diethyl ether, and the combined organic layers extracted with water. The combined aqueous layers were acidified to pH 4 with 6 N HCl and extracted with methylene chloride, and the methylene chloride layer was washed with brine, dried over Na$_2$SO$_4$, and filtered. The filtrate was concentrated in vacuo and the residue purified by flash column chromatography (1:1 methylene chloride:ethyl acetate) giving the title compound as a light yellow solid (2.15 g, 18%). $^1$H NMR (300 MHz, CDCl$_3$)

δ 13.25 (br s, 1H), 7.84 (d, 1H, J=7.5 Hz), 6.23 (d, 1H, J=7.5 Hz), 3.00 (septet, 1H, J=7.0 Hz), 1.36 (s, 3H), 1.34 (s, 3H). Also recovered from the column was the mono-methylated side-product 3-cyano-6-ethyl-2(1H)pyridinone (5.50 g, 50%), which was used to make the title compound in Example 97. $^1$H NMR (300 MHz, CDCl$_3$) δ 7.84 (d, J=7.5 Hz, 1H), 6.23 (d, J=7.4 Hz, 1H), 2.76 (q, J=7.6 Hz, 2H), 1.35 (t, J=7.5 Hz, 3H).

2. 3-Carboxy-6-isopropyl-2 (1H)-pyridinone

3-Cyano-6-isopropyl-2(1H)-pyridinone (2.92 g, 18.0 mmol), as prepared in the preceding step, was dissolved in hot 50% v/v sulfuric acid (45 mL) and refluxed for 3 hours. After cooling to ambient temperature, the reaction mixture was poured into 200 mL of ice water and the resulting precipitate collected by filtration, washed with water, then air and vacuum dried giving the title compound (2.83 g, 87%) as a white solid. $^1$H NMR (300 MHz, CDCl$_3$) δ 13.67 (s, 1H), 12.75 (br s, 1H), 8.56 (d, 1H, J=7.5 Hz), 6.56 (dd, 1H, J=7.6 Hz, 1.6 Hz), 3.02 (septet, 1H, J=6.9 Hz), 1.41 (s, 3H), 1.39 (s, 3H).

3. 3-(Benzyloxycarbonyl)amino-6-isopropyl-2(1H)-pyridinone

3-Carboxy-6-isopropyl-2(1H)-pyridinone (2.82 g, 15.6 mmol), as prepared in the preceding step, diphenylphosphoryl azide (3.50 mL, 16.2 mmol), and triethylamine (2.30 mL, 16.5 mmol) were refluxed in 1,4-dioxane (100 mL) for 16 hours. Benzyl alcohol (1.65 mL, 15.9 mmol) and additional triethylamine (2.40 mL, 17.2 mmol) were added and the reaction refluxed another 24 hours. After concentrating the reaction mixture in vacuo, the residue was dissolved in methylene chloride, washed with pH 1 brine, saturated NaHCO$_3$, and pH 7 brine, dried over MgSO$_4$, and filtered. The evaporated filtrate was then purified by flash column chromatography (gradient elution, 10% to 25% ethyl acetate in methylene chloride) giving the title compound as a light yellow solid (1.10 g, 25%). $^1$H NMR (300 MHz, CDCl$_3$) δ 11.61 (br s, 1H), 8.05 (br d, 1H, J=7.2 Hz), 7.67 (s, 1H), 7.39 (m, 5H), 6.08 (d, 1H, J=7.7 Hz), 5.21 (s, 2H), 2.80 (septet, 1H, J=6.9 Hz), 1.28 (s, 3H), 1.26 (s, 3H).

4. 3-(Benzyloxycarbonyl)amino-6-isopropyl-1-(tert-butoxycarbonylmethyl)-2-pyridinone 3-(Benzyloxycarbonyl)amino-6-isopropyl-2 (1H)-pyridinone (1.10 g, 3.84 mmol), as prepared in the preceding step, was dissolved in anhydrous tetrahydrofuran (30 mL) and cooled to 0° C. under nitrogen. A 1.0 M solution of lithium bis(trimethylsilyl)amide in hexanes (4.2 mL, 4.2 mmol) was added via syringe and the reaction stirred for one hour. tert-Butylbromoacetate (0.70 mL, 4.3 mmol) was then added-via syringe and the reaction stirred at ambient temperature for 16 hours. After concentration in vacuo, the crude product was purified by flash column chromatography (1:1 hexane:ethyl acetate) giving the title compound as a pale yellow oil (1.38 g, 90%). $^1$H NMR (300 MHz, CDCl$_3$) δ 8.00 (br d, 1H, J=7.8 Hz), 7.78 (s, 1H), 7.36 (m, 5H), 6.15 (d, 1H, J=7.9 Hz), 5.19 (s, 2H), 4.79 (s, 2H), 2.72 (m, 1H), 1.46 (s, 9H), 1.26 (s, 3H), 1.23 (s, 3H). Mass spectrum (MALDI-TOF, gentisic acid matrix) calcd. for C$_{22}$N$_{28}$N$_2$O$_5$: 423.2 (M+Na). Found: 423.6.

5. 3-Amino-6-isopropyl-1-(tert-butoxycarbonylmethyl)-2-pyridinone 3-(Benzyloxycarbonyl)amino-6-isopropyl-1-(tert-butoxycarbonylmethyl)-2-pyridinone (1.35, 3.37 mmol), as prepared in the preceding step, and 10% palladium (0) on activated carbon (0.12 g) were dissolved in methanol (50 mL), degassed, backfilled with nitrogen, and stirred under hydrogen gas at ambient pressure and temperature for 2 hours. The reaction mixture was then filtered through Celite and the filtrate evaporated giving the title compound as a golden oil, which was used without further purification.

6. 3-(3-Methylphenylsulfonyl)amino-6-isopropyl-1-(tert-butoxycarbonylmethyl)-2-pyridinone 3-Amino-6 isopropyl-1-(tert-butoxycarbonylmethyl)-2-pyridinone (assumed to be 3.37 mmol), as prepared in the preceding step, and N-methylmbrpholine (1.0 mL, 9.1 mmol) were dissolved in methylene chloride (20 mL) and cooled to 0° C. A solution of m-toluenesulfonyl chloride (0.67 g, 3.5 mmol) in methylene chloride (5 mL) was added and the reaction stirred at ambient temperature for 16 hours. After evaporation in vacuo, the crude product was dissolved in methylene chloride, washed with 10% aqueous citric acid, saturated NaHCO$_3$, and brine, dried over MgSO$_4$, and filtered. The evaporated filtrate gave the title compound (1.24 g, 88%) as a tan solid. $^1$H NMR (300 MHz, CDCl$_3$) δ 7.65 (m, 2H), 7.58 (br s, 1H), 7.46 (d, 1H, J=7.8 Hz), 7.33 (m, 2H), 6.08 (d, 1H, J=7.9 Hz), 4.69 (s, 2H), 2.67 (m, 1H), 2.38 (s, 3H), 1.41 (s, 9H), 1.22 (s, 3H), 1.19 (s, 3H).

7. 3-(3-Methylphenylsulfonyl)amino-6-isopropyl-1-(carboxymethyl)-2-pyridinone 3-(3-Methylphenylsulfonyl)amino-6-isopropyl-1-(tert-butoxycarbonylmethyl)-2-pyridinone (1.24 g, 2.95 mmol), as prepared in the preceding step, was dissolved in methylene chloride (20 mL) and reacted with trifluoroacetic acid (8 mL) at ambient temperature for 2 hours. After evaporation in vacuo, the crude product was dissolved in methylene chloride, washed with pH 7 buffer and brine, dried over MgSO$_4$, and filtered. Evaporation of the filtrate gave the title compound (0.72 g, 67%) as a light yellow solid. Mass spectrum (LCMS, ESI) calcd. for C$_{17}$H$_{20}$N$_2$O$_5$S: 365.4 (M+H). Found: 365.1.

8. 3-(3-Methylphenylsulfonyl)amino-6-isopropyl-1-{[N,N'-di(tert-butoxycarbonyl)]-2-(guanidinyloxyethyl)aminocabonylmethyl}-2-pyridinone 3-(3-Methylphenylsulfonyl)amino-6-isopropyl-1-(carboxymethyl)-2-pyridinone (0.71 g, 1.95 mmol), as prepared in the preceding step, Castro's reagent (BOP, p. 905 g, 2.05 mmol), and [N,N'-di(tert-butoxycarbonyl)] 2-aminoethoxyguanidine (0.710 g, 2.00 mmol), as prepared in step 4 of Example 2, were dissolved in methylene chloride (40 mL) and reacted with triethylamine (0.75 mL, 5.4 mmol) at ambient temperature for 3 days. After concentration in vacuo, the crude product was dissolved in methylene chloride, washed with 10% aqueous citric acid, saturated NaHCO$_3$, and brine, dried over Na$_2$SO$_4$, and filtered. The evaporated filtrate was purified by flash column chromatography (5% methanol in methylene chloride) giving the title compound as a light yellow solid (0.70 g, 54%). $^1$H NMR (300 MHz, CDCl$_3$) δ 9.15 (s, 1H), 8.34 (br t, 1H, J=5.0 Hz), 7.67 (m, 3H), 7.59 (s, 1H), 7.40 (d, 1H, J=7.9 Hz), 7.34 (m, 2H), 6.06 (d, 1H, J=7.9

Hz), 4.86 (s, 2H), 4.09 (m, 2H), 3.58 (dd, 2H, J=8.8 Hz, 5.0 Hz), 2.86 (m, 1H), 2.38 (s, 3H), 1.52 (s, 9H), 1.47 (s, 9H), 1.20 (s, 3H), 1.17 (s, 3H).

9. 3-(3-Methylphenylsulfonyl)amino-6-isopropyl-1-{2-(guanidinyloxyethyl)aminocabonylmethyl}-2-pyridin one hydrochloride 3-(3-Methylphenylsulfonyl)amino-6-isopropyl-1-{[N,N'-di(tert-butoxycarbonyl)]-2-(guanidinyloxyethyl)aminocabonylmethyl}-2-pyridinone (0.70 g, 1.05 mmol), as prepared in the preceding step, was dissolved in methylene chloride (10 mL) and reacted with trifluoroacetic acid (5 mL) at ambient temperature for 2.5 hours. The evaporated crude product was lyophilized from acetonitrile/water, purified by flash column chromatography (gradient elution, 10% to 0.20% methanol in methylene chloride saturated with gaseous ammonia), and evaporated from 4 N HCl in ethanol (20 mL) giving the title compound as a white solid (0.36 g, 68%). $^1$H NMR (300 MHz, DMSO-$d_6$) δ 10.91 (br s, 1H), 9.34 (brd s, 1H), 8.49 (t, 1H, J=5.5 Hz), 7.65 (m, 6H), 7.43 (m, 2H), 7.28 (d, 1H, J=7.8 Hz), 6.14 (d, 1H, J=7.9 Hz), 4.69 (s, 2H), 3.79 (t, 2H, J=5.3 Hz), 3.38 (m, 2H), 2.79 (m, 1H), 2.35 (s, 3H). 1.13 (s, 3H), 1.08 (s, 3H). Mass spectrum (LCMS, ESI) calcd. for $C_{20}H_{28}N_6O_5S$: 465.5 (M+H). Found: 465.1.

EXAMPLE 97

3-(3-Methylphenylsulfonyl)amino-6-ethyl-1-[(2-guanidinooxyethyl)aminocarbonylmethyl]-2-pyridinone trifluoroacetate

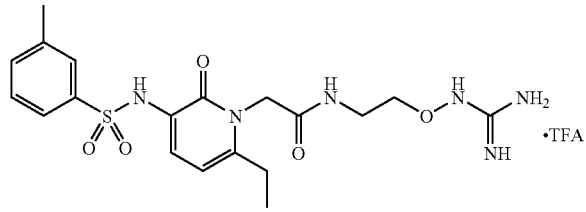

The title compound was prepared in a manner analogous to Example 96. $^1$H-NMR (300 MHz, DMSO-$d_6$) δ 10.92 (s, 1H), 9.32 (s, 1H), 8.42 (t, J=5.6 Hz, 1H), 7.71 (br s, 4H), 7.67 (s, 1H), 7.64 (t, J=3.0 Hz, 1H), 7.42 (d, J=6.1 Hz, 1H), 7.29 (d, J=7.7 Hz, 1H), 6.07 (d, J=7.8 Hz, 1H), 4.62 (s, 2H), 3.79 (t, J=5.4 Hz, 2H), 3.34 (t, J=5.6 Hz, 2H), 2.24 (s, 3H). Mass spectrum (MALDI-TOF, α-cyano-4-hydroxycinnamic acid matrix) calcd. for $C_{19}H_{26}N_6O_5S$: 451.2 (M+H), 473.2 (M+Na); Found: 451.1, 473.0.

EXAMPLE 98

3-(3-Methylphenylsulfonyl)amino-6-propyl-1-{2-(guanidinyloxyethyl) aminocabonylmethyl}-2-pyridinone trifluoroacetate

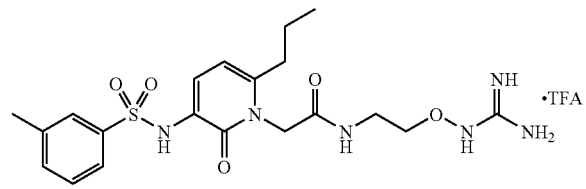

The title compound was prepared in a manner analogous to Example 96. $^1$H NMR (300 MHz, DMSO-$d_6$) δ 11.25 (s, 1H), 9.32 (s, 1H), 8.48 (t, 1H, J=5.5 Hz), 7.91 (br s, 4H), 7.63 (m, 2H), 7.42 (m, 2H), 7.29 (d, 1H, J=7.7 Hz), 6.07 (d, 1H, J=7.7 Hz), 4.61 (s, 2H), 3.81 (t, 2H, J=5.3 Hz), 3.35 (m, 2H), 2.45 (t, 2H, J=7.7 Hz), 2.35 (s, 3H), 1.50 (sextet, 2H, J=7.5 Hz), 0.89 (t, 3H, J=7.3 Hz). Mass spectrum (LCMS, ESI) calcd. for $C_{20}H_{28}N_6O_5S$: 465.5 (M+H). Found: 465.1.

EXAMPLE 99

3-(3-Methylphenylsulfonyl)amino-6-methyl-1-[(2-N''-methylguanidinooxyethyl)aminocarbonylmethyl]-2-pyridinone hydrochloride

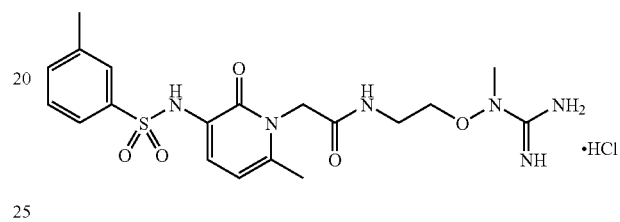

A solution of 3-(3-methylphenylsulfonyl)amino-6-methyl-1-[(2-guanidinooxyethyl) aminocarbonylmethyl]-2-pyridinone hydrochloride (0.2 g, 0.42 mmol), as prepared in step 5 of Example 5, in N,N-dimethylformamide (6 mL) was treated with sodium bicarbonate (0.78 g, 9.2 mmol) followed by methyl iodide (0.32 mL, 5 mmol) and allowed to stir at room temperature for 2.5 h. The reaction mixture was evaporated under high vacuum and the residue was treated with brine and adjusted to pH 1 with 1M HCl. The insoluble material was collected by filtration. The aqueous layer was extracted with methylene chloride (5×). The combined methylene chloride extracts were extracted with saturated sodium bicarbonate (2×). The combined aqueous bicarbonate extracts were adjusted to pH 1 with 1M HCl. The insoluble material was collected by filtration and combined with the previous solids from the acidic brine treatment. The solids were dried under high vacuum overnight, then treated with methanol and filtered to remove insoluables. Evaporation of the filtrate gave the title compound as a white solid (154 mg, 75%). $^1$H-NMR (300 MHz, DMSO-$d_6$) δ 9.30 (s, 1H), 8.85 (t, J=5.3 Hz, 1H), 8.14 (s, 4H), 7.61-7.66 (m, 2H), 7.39-7.44 (m, 2H), 7.23 (d, J=7.6 Hz, 1H), 6.08 (d, J=8.2 Hz, 1H), 4.67 (m, 2H), 3.91 (t, J=5.1 Hz, 2H), 3.39 (m, 2H), 3.28 (s, 3H), 2.35 (s, 3H), 2.19 (s, 3H). Mass spectrum (LCMS, ESI) clacd. for $C_{19}H_{26}N_6O_5S$: 451 (M+H); Found: 451.2. MS-MS of 451.2 peak gave 408.9 (M–C(=NH)NH).

EXAMPLE 100

3-(3-Methylphenylsulfonyl)amino-6-methyl-1-[(2-N''-ethylguanidinooxyethyl)aminocarbonylmethyl]-2-pyridinone hydrochloride

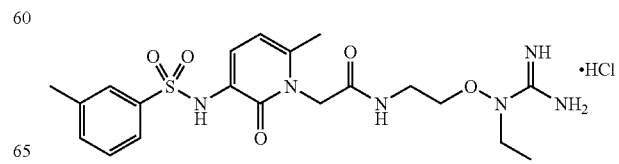

The title compound was prepared in a manner analogous to Example 99. ¹H NMR (300 MHz, DMSO-$d_6$) δ 9.26 (br s, 1H), 8.55 (t, 1H, J=5.2 Hz), 7.95 (br s, 4H), 7.64 (m, 2H), 7.42 (m, 2H), 7.24 (d, 1H, J=7.5 Hz), 6.08 (d, 1H, J=7.7 Hz), 4.63 (s, 2H), 3.87 (br t, 2H, J=5.0 Hz), 3.66 (q, 2H, J=6.9 Hz), 2.35 (s, 3H), 2.19 (s, 3H), 1.09 (t, 3H, J=6.9 Hz). Mass spectrum (LCMS, ESI) calcd. for $C_{20}H_{28}N_6O_5S$: 465.5 (M+H). Found: 465.1. MS-MS of 465.1 peak gave 423.0 (M−C(=NH)NH).

EXAMPLE 101

3-(3-Methylphenylsulfonyl)amino-6-methyl-1-[(2-N"-benzylguanidinooxyethyl)aminocarbonylmethyl]-2-pyridinone hydrochloride

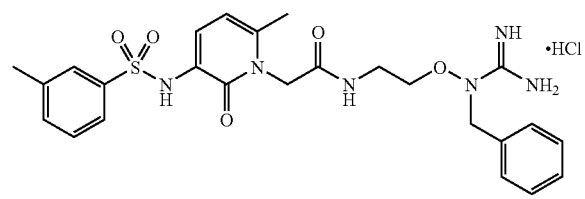

The title compound was prepared in a manner analogous to Example 99. Mass spectrum (LCMS, ESI) calcd. for $C_{25}H_{30}N_6O_5S$: 527.6 (M+H). Found: 527.0. MS-MS of 527.0 peak gave 485.0 (M−C(=NH)NH).

EXAMPLE 102

3-(3-Methylphenylsulfonyl)amino-6-methyl-1-[(2-N"-butylguanidinooxyethyl)aminocarbonylmethyl]-2-pyridinone hydrochloride

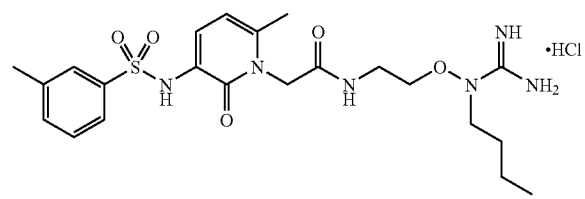

The title compound was prepared in a manner analogous to Example 99. ¹H NMR (300 MHz, CDCl₃/CD₃OD) δ 7.64 (m, 2H), 7.42 (d, 1H, J=7.7 Hz), 7.36 (m, 2H), 6.11 (d, 1H, J=7.7 Hz), 4.70 (s, 2H), 3.58 (t, 2H, J=7.3 Hz), 3.49 (t, 2H, J=4.9 Hz), 2.39 (s, 3H), 2.30 (s, 3H), 1.64 (m, 2H), 1.36 (m, 4H), 0.95 (t, 3H, J=7.2 Hz). Mass spectrum (LCMS, ESI) calcd. for $C_{22}H_{32}N_6O_5S$: 493.6 (M+H). Found: 493.3. MS-MS of 493.3 peak gave 452.0 (M−C(=NH)NH).

EXAMPLE 103

3-(3-Methylphenylsulfonyl)amino-6-methyl-1-[(2-N-methylguanidinooxyethyl)aminocarbonylmethyl]-2-pyridinone trifluoroacetate

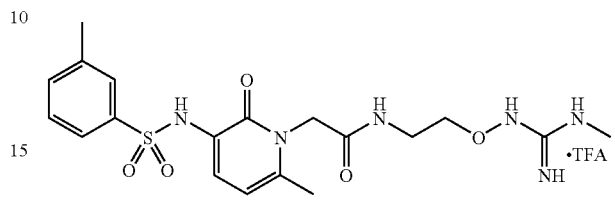

1. [N,N'-Di(tert-butoxycarbonyl)] 2-(benzyloxycarbonylamino)ethoxy-N-methylguanidine To a solution of [N,N'-di(tert-butoxycarbonyl)] 2-(benzyloxycarbonylamino) ethoxyguanidine (905 mg, 2.0 mmol), as prepared in step 3 of Example 2, methanol (121 µL, 3.0 mmol) and triphenylphosphine (790 mg, 3.0 mmol) in tetrahydrofuran (30 mL) was added diethyl azodicarboxylate (520 mg, 3.0 mmol). The mixture was stirred at ambient temperature overnight. Ethyl acetate (50 mL) was added, washed with saturated NaHCO₃ (40 mL), brine (2×40 mL) and dried over Na₂SO₄. After evaporating the solvent, the residue was purified by flash chromatography (0-4% ethyl acetate in methylene chloride) to give the title compound as a white solid (385 mg, 41%). ¹H-NMR (300 MHz, CDCl₃) δ 7.36 (m, 5H), 5.30 (br s, 1H), 5.11 (s, 2H), 4.12 (t, J=5.0 Hz, 2H), 3.50 (t, J=5.0 Hz, 2H), 3.07 (s, 3H), 1.48 (s, 9H), 1.43 (s, 9H).

2. [N,N'-Di(tert-butoxycarbonyl)] 2-aminoethoxy-N-methylguanidine

A mixture of [N,N'-di(tert-butoxycarbonyl)] 2-(benzyloxycarbonylamino)ethoxy-N-methylguanidine (700 mg, 1.5 mmol), as prepared in the preceding step, 10% Pd/C (70 mg) in methanol (20 mL) and chloroform (5 mL) was hydrogenated under hydrogen (balloon) for 1 h. The catalyst was removed by filtration through Celite, the filtrate was concentrated in vacuo. The residue was purified by flash chromatography (95:5 methylene chloride:methanol saturated with ammonia) to give the title compound as a colorless foam (250 mg, 50%). ¹H-NMR (300 MHz, CDCl₃) δ 4.14 (t, J=5.0 Hz, 2H), 3.09 (s, 3H), 3.06 (q, J=5.0 Hz, 2H), 1.50 (s, 9H), 1.46 (s, 9H).

3. 3-(3-Methylphenylsulfonyl)amino-6-methyl-1-{[N,N'-di(tert-butoxycarbonyl)] [2-(N-methylguanidinooxyethyl)aminocarbonylmethyl]}-2-pyridinone To a solution of 3-(3-methylphenylsulfonyl)amino-6-methyl-1-carboxymethyl-2-pyridinone (253 mg, 0.75 mmol), as prepared in step 2 of Example 5, [N,N'-di(tert-butoxycarbonyl)] 2-aminoethoxy-N-methylguanidine (250 mg, 0.75 mmol), as prepared in the preceding step, diisopropylethylamine (180 µL, 1.0 mmol) in N,N-dimethylformamide (10 mL) was added Castro's reagent (BOP) (355 mg, 0.8 mmol). The mixture was stirred at room temperature overnight. Ethyl acetate (50 mL) was added, washed with saturated NaHCO$_3$ (2×20 mL), 10% citric acid (2×20 mL) and brine (20 mL), and dried over Na$_2$SO$_4$. After evaporating the solvent in vacuo, the residue was purified twice by column chromatography (2:1 ethyl acetate:hexane; then 2% methanol in methylene chloride) to give the title compound as a white solid (380 mg, 78%). $^1$H-NMR (300 MHz, CDCl$_3$) δ 8.12 (s, 1H), 7.67 (m, 3H), 7.48 (d, J=7.6 Hz, 1H), 7.34 (s, 1H), 7.31 (s, 1H), 7.09 (m, 1H), 6.08 (d, J=7.8 Hz, 1H), 4.61 (s, 2H), 4.02 (t, J=5.1 Hz, 2H), 3.46 (q, J=5;3 Hz, 2H), 3.09 (s, 3H), 2.39 (s, 3H), 2.37 (s, 3H), 1.53 (s, 9H), 1.47 (s, 9H).

4. 3-(3-Methylphenylsulfonyl)amino-6-methyl-1-[(2-N-methylguanidinooxyethyl)aminocarbonylmethyl]-2-pyridinone trifluoroacetate A mixture of 3-(3-methylphenylsulfonyl)amino-6-methyl-1-{[N,N'-di(tert-butoxycarbonyl)] [2-(N-methylguanidinooxypropyl)aminocarbonylmethyl]}-2-pyridinone (370 mg, 0.57 mmol), as prepared in the preceding step, and trifluoroacetic acid (2 mL) in methylene chloride (3 mL) was stirred at room temperature for 2 h. After evaporating the solvent in vacuo, the residue was purified by Waters Sep-Pak (10 g, 10% methanol in methylene chloride) to give the title compound as a colorless foam (310 mg, 96%). $^1$H-NMR (300 MHz, DMSO-d$_6$) δ 10.91 (s, 1H), 9.28 (s, 1H), 8.43 (t, J=5.5 Hz, 1H), 8.09 (d, J=5.0 Hz, 1H), 7.93 (br s, 2H), 7.66 (s, 1H), 7.62 (m, 1H), 7.43 (m, 2H), 7.24 (d, 1H, J=7.6 Hz), 6.09 (d, 1H, J=7.7 Hz), 4.62 (s, 2H), 3.79 (t, 2H, J=5.2 Hz), 3.35 (q, 2H, J=5.4 Hz), 2.77 (d, J=4.8 Hz, 3H), 2.35 (s, 3H), 2.19 (s, 3H). Mass spectrum (LCMS, ESI) calcd. for C$_{19}$H$_{26}$SN$_6$O$_5$: 451.0 (M+H); found: 451.1. MS-MS of 451.1 peak gave 394.9 (M−C(=NH)NCH$_3$).

EXAMPLE 104

3-(Benzylsulfonyl)amino-6-methyl-1-[(2-N-methylguanidinooxyethyl) aminocarbonylmethyl]-2-pyridinone trifluoroacetate

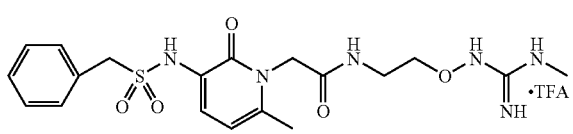

The title compound was prepared in a manner analogous to Example 103. $^1$H-NMR (300 MHz, DMSO-d$_6$) δ 10.89 (s, 1H), 8.57 (s, 1H), 8.47 (t, J=5.5 Hz, 1H), 8.09 (br s, 1H), 7.93 (s, 2H), 7.34 (m, 5H), 7.13 (d, J=7.5 Hz, 1H), 6.10 (d, J=7.7 Hz, 1H), 4.73 (s, 2H), 4.51 (s, 2H), 3.83 (t, J=5.4 Hz, 2H), 3.41 (m, 2H), 2.77 (d, J=4.9 Hz, 3H), 2.25 (s, 3H). Mass spectrum (MALDI-TOF, α-cyano-4-hydroxycinnamic acid matrix) calcd. for C$_{19}$H$_{26}$N$_6$O$_5$S: 451.2 (M+H), 473.2 (M+Na); Found: 451.4, 473.5. MS-MS of 451.4 peak gave 394.9 (M−C(=NH)NCH$_3$).

EXAMPLE 105

3-(3-Methylphenylsulfonyl)amino-6-methyl-1-[(2-(N-methoxycarbonyl) guanidinooxyethyl)aminocarbonylmethyl]-2-pyridinone

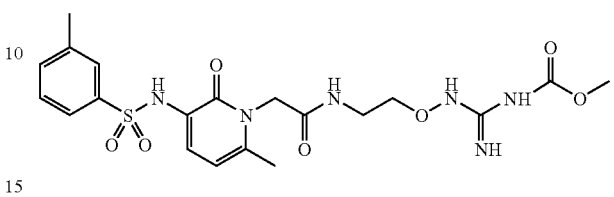

A suspension of 3-(3-methylphenylsulfonyl)amino-6-methyl-1-[(2-guanidinooxyethyl) aminocarbonylmethyl]-2-pyridinone hydrochloride (0.2 g, 0.42 mmol), as prepared in step 5 of Example 5, in acetonitrile (10 mL) was treated with N,N-diisopropylethylamine (0.08 mL, 0.46 mmol) and dimethyl pyrocarbonate (0.05 mL, 0.46 mmol). The reaction mixture was allowed to stir at room temperature overnight. An additional solvent, N,N-dimethylformamide (5 mL) was added to effect solution. Additional dimethyl pyrocarbonate (0.30 mL, 2.76 mmol) was added and the reaction mixture was stirred for 2 days. The reaction mixture was evaporated to dryness under high vacuum and the residue was purified on a silica gel column (5 g SepPak) using 4% methanol in methylene chloride as eluting solvent to give 0.071 g (29% yield) of desired product as a white solid. $^1$H-NMR (300 MHz, DMSO-d$_6$) δ 9.65 (s, 1H), 9.30 (s, 1H), 8.28 (t, J=5.5 Hz, 1H), 7.60-7.67 (m, 2H), 7.38-7.44 (m, 2H), 7.23 (d, J=7.5 Hz, 1H), 6.20 (s, 2H), 6.06 (d, J=7.6 Hz, 1H), 4.61 (m, 2H), 3.73 (t, J=5.5 Hz, 2H), 3.61 (s, 3H), 3.27-3.31 (m, 2H), 2.35 (s, 3H), 2.18 (s, 3H). Mass spectrum (LCMS, ESI) calcd. for C$_{20}$H$_{26}$N$_6$O$_7$S: 495 (M+H); Found: 495.0.

EXAMPLE 106

3-(3-Methylphenylsulfonyl)amino-6-methyl-1-[(2-(N,N',N''-triethoxycarbonyl)guanidinooxyethyl)aminocarbonylmethyl]-2-pyridinone

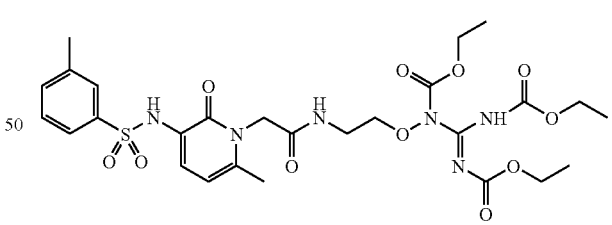

To a solution of 3-(3-methylphenyl)sulfonylamino-6-methyl-1-[(2-guanidinooxyethyl) aminocarbonylmethyl]-2-pyridinone hydrochloride (237 mg, 0.5 mmol), as prepared in step. 5 of Example 5, and N,N'-diiso-propylethylamine (180 µL, 1.0 mmol) in N,N-dimethylformamide (10 mL) was added diethyl pyrocarbonate (150 µL, 1.0 mmol). The mixture was stirred at ambient temperature overnight. The N,N-dimethylformamide was evaporated under high vacuum, the residue was dissolved in methylene chloride (50 mL), washed with 10% citric acid (2×20 mL), brine (20 mL) and dried over Na$_2$SO$_4$. After evaporating the solvent, the residue was purified by Waters Sep-Pak (10 g, 30 —40% ethyl acetate in methylene chloride) to give the title compound as a white solid (210 mg, 65%). $^1$H-NMR (300 MHz, CDCl$_3$) δ 9.33 (br s, 1H), 8.64 (s, 1H), 8.58 (br s, 1H), 7.97 (m, 2H), 7.52 (d, J=7.5 Hz, 1H), 7.26 (m, 2H), 6.15 (d, J=7.7 Hz, 1H), 4.70-5.00 (m, 2H), 4.40 (q, J=7.1 Hz, 2H), 4.21 (q, J=7.2 Hz, 2H), 4.07 (q, J=7.1 Hz, 2H), 3.85 (m, 2H), 3.54 (m, 2H), 2.41 (s, 3H), 2.39 (s, 3H), 1.41 (t, J=7.1 Hz, 3H), 1.30 (t, J=7.2 Hz, 3H), 1.09 (t, J=7.1 Hz, 3H). Mass spectrum (LCMS, ESI) calcd. for C$_{27}$H$_{36}$N$_6$O$_{11}$S: 653.0 (M+H); Found: 653.0.

EXAMPLE 107

3-(3-Methylphenylsulfonyl)amino-6-methyl-1-[(2-(N,N'-diethoxycarbonyl) guanidinooxyethyl)aminocarbonylmethyl]-2-pyridinone

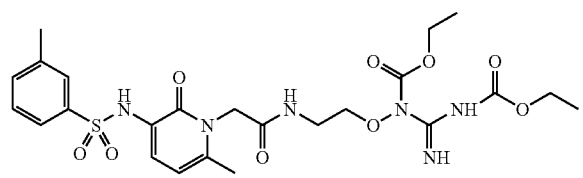

and 3-(3-Methylphenylsulfonyl)amino-6-methyl-1-[(2-(N-ethoxycarbonyl) guanidinooxyethyl)aminocarbonylmethyl]-2-pyridinone

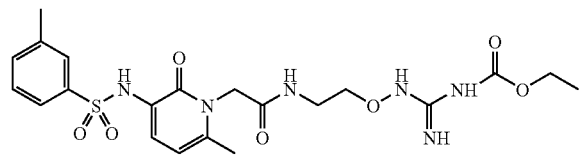

To a solution of 3-(3-methylphenyl)sulfonylamino-6-methyl-1-[(2-guanidinooxyethyl) aminocarbonylmethyl]-2-pyridinone hydrochloride (475 mg, 1.0 mmol), as prepared in step 5 of Example 5, and N-methylmorpholine (220 μL, 2.0 mmol) in N,N'-dimethylformamide (10 mL) was added diethyl pyrocarbonate (150 μL, 1.0 mmol). The mixture was stirred at ambient temperature overnight. The N,N-dimethylformamide was evaporated under high vacuum, the residue was dissolved in methylene chloride (50 mL), washed with 10% citric acid (2×20 mL), brine (20 mL) and dried over Na$_2$SO$_4$. After evaporating the solvent, the residue was purified by Waters Sep-Pak (10 g, 30-40% ethyl acetate in methylene chloride then 25 methanol in methylene chloride) to give 3-(3-methylphenylsulfonyl)amino-6-methyl-1-[(2-(N,N'-diethoxycarbonyl)guanidinooxyethyl) aminocarbonylmethyl]-2-pyridinone as a white solid (320 mg, 55%). $^1$H-NMR (300 MHz, CDCl$_3$) δ 9.34 (br s, 1H), 8.74 (s, 1H), 8.59 (br s, 1H), 7.67 (s, 1H), 7.64 (m, 1H), 7.60 (s, 1H), 7.38 (d, J=7.5 Hz, 1H), 7.32 (d, J=5.2 Hz, 2H), 6.01 (d, J=7.6 Hz, 1H), 4.97+4.67 (m, 2H), 4.40 (q, J=7.1 Hz, 2H), 4.14 (q, J=7.1 Hz, 2H), 4.36+3.91 (m, 2H), 3.52 (m, 2H), 2.38 (s, 3H), 2.26 (s, 3H), 1.42 (t, J=7.1 Hz, 3H), 1.21 (t, J=7.1 Hz, 3H). Mass spectrum (LCMS, ESI) calcd. for C$_{24}$H$_{32}$N$_6$O$_9$S: 581.2 (M+H); Found: 581.0. 3-(3-Methylphenylsulfonyl)amino-6-methyl-1-[(2-(N-ethoxycarbonyl)guanidinooxyethyl) aminocarbonylmethyl]-2-pyridinone as a white solid (80 mg, 16%). $^1$H-NMR (300 MHz, CDCl$_3$) δ 8.30 (br s, 1H), 8.17 (br s, 1H), 7.56 (m, 4H), 7.33 (m, 2H), 6.14 (d, J=7.7 Hz, 1H), 5.77 (br s, 2H), 4.67 (br s, 2H), 4.35 (q, J=7.1 Hz, 2H), 3.85 (m, 2H), 3.42 (m, 2H), 2.44 (s, 3H), 2.36 (s, 3H), 1.39 (t, J=7.1 Hz, 3H). Mass spectrum (LCMS, ESI) calcd. for C$_{21}$H$_{28}$N$_6$O$_7$S: 509.1 (M+H); Found: 509.1.

EXAMPLE 108

3-(3-Methylphenylsulfonyl)amino-6-methyl-1-{[2-N"-(3-phenylpropyl) guanidinooxyethyl]aminocarbonylmethyl}-2-pyridinone hydrochloride

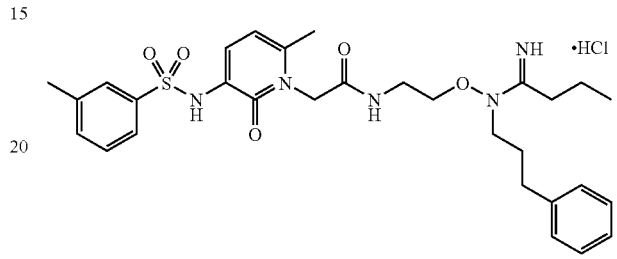

The title compound was prepared in a manner analogous to Example 99. $^1$H NMR (300 MHz, DMSO-d$_6$) δ 9.25 (s, 1H0, 8.65 (t, 1H, J=5 Hz), 8.03 (br s, 3H), 7.78 (br s, 1H), 7.64 (m, 2H), 7.26 (m, 10H), 6.07 (m, 1H), 4.63 (br s, 2H), 3.89 (t, 2H, J=4.9 Hz), 3.71 (t, 2H, J=7 Hz), 2.58 (m, 2H), 2.34 (s, 3H), 2.16 (s, 3H), 1.87 (m, 2H). Mass spectrum (LCMS, ESI) calcd. for C$_{27}$H$_{34}$N$_6$O$_5$S: 555.0 (M+H). Found: 555.1. MS-MS of 555.1 peak gave 513.0 (M–C(=NH)NH).

EXAMPLE 109

Tablet Preparation

Tablets containing 25.0, 50.0, and 100.0 mg, respectively, of the following active compounds are prepared as illustrated below:

a. 3-benzylsulfonylamino-6-methyl-1-[(3-guanidinooxypropyl) aminocarbonylmethyl]-2-pyridinone; and b. 3-benzylsulfonylamino-6-methyl-1-[(2-guanidinooxyethyl) aminocarbonylmethyl]-2-pyridinone

| TABLET FOR DOSES CONTAINING FROM 25-100 MG OF THE ACTIVE COMPOUND | | | |
|---|---|---|---|
| | Amount-mg | | |
| Active Compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 110

Intravenous Solution Preparation

An intravenous dosage form of the above-indicated active compounds is prepared as follows:

| | |
|---|---|
| Active Compound | 0.5-10.0 mg |
| Sodium Citrate | 5-50 mg |
| Citric Acid | 1-15 mg |
| Sodium Chloride | 1-8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

EXAMPLE 111

In Vitro Inhibition of Purified Enzymes

Reagents: All buffer salts were obtained from Sigma Chemical Company (St. Louis, Mo.), and were of the highest purity available. The enzyme substrates, N-benzoyl-Phe-Val-Arg-p-nitroanilide (Sigma B7632), N-benzoyl-Ile-Glu-Gly-Arg-p-nitroanilide hydrochloride (Sigma B2291), N-p-Tosyl-Gly-Pro-Lys-p-nitroanilide (Sigma T6140), N-succinyl-Ala-Ala-Pro-Phe-p-nitroanilide (Sigma S7388) and N-CBZ-Val-Gly-Arg-p-nitroanilide (Sigma C7271) were obtained from Sigma N-succinyl-Ala-Ala-Pro-Arg-p-nitroanilide (BACHEM L-1720) and N-succinyl-Ala-Ala-Pro-Val-p-nitroanilide (BACHEM L-1770) were obtained from BACHEM (King of Prussia, Pa.).

Human α-thrombin, human factor Xa and human plasmin were obtained from Enzyme Research Laboratories (South Bend, Ind.). Bovine α-chymotrypsin (Sigma C4129), bovine trypsin (Sigma T8642) and human kidney cell urokinase (Sigma U5004) were obtained from Sigma. Human leukocyte elastase was obtained from Elastin Products (Pacific, Mo.).

$K_i$ Determinations: All assays are based on the ability of the test compound to inhibit the enzyme catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for $K_m$. Test compounds are prepared as a 1.0 mg/ml solution in DMSO. Dilutions are prepared in DMSO yielding 8 final concentrations encompassing a 200 fold concentration range. Enzyme solutions are prepared at the concentrations listed below in assay buffer.

In a typical $K_i$ determination, into each well of a 96 well plate is pipetted 280 mL of substrate solution, 10 mL of test compound solution, and the plate allowed to thermally equilibrate at 37° C. in a Molecular Devices plate reader for >15 minutes. Reactions were initiated by the addition of a 10 mL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined $K_i$ value.

Thrombin: Thrombin activity was assessed as the ability to hydrolyze the substrate N-succinyl-Ala-Ala-Pro-Arg-p-nitroanilide. Substrate solutions were prepared at a concentration of 32 mM (32 mM<<Km=180 mM) in assay buffer. Final DMSO concentration was 4.3%. Purified human a-thrombin was diluted into assay buffer to a concentration of 15 nM. Final reagent concentrations were: [thrombin]=0.5 nM, [substrate N-succinyl-Ala-Ala-Pro-Arg-p-nitroanilide]=32 mM.

Factor X [FXa]: FXa activity was assessed as the ability to hydrolyze the substrate N-benzoyl-Ile-Glu-Gly-Arg-p-nitroanilide hydrochloride. Substrate solutions were prepared at a concentration of 51 mM (51<<$K_m$=1.3 mM) in assay buffer. Final DMSO concentration was 4.3%. Purified activated human Factor X was diluted into assay buffer to a concentration of 300 nM. Final reagent concentrations were: [FXa]=10 nM, [N-benzoyl-Ile-Glu-Gly-Arg-p-nitroanilide hydrochloride]=51 mM.

Plasmin: Plasmin activity was assessed as the ability to hydrolyze the N-p-Tosyl-Gly-Pro-Lys-p-nitroanilide. Substrate solutions were prepared at a concentration of 37 mM (37 mM<<$K_m$=243 mM) in assay buffer. Final DMSO concentration was 4.3%. Purified human plasmin was diluted into assay buffer to a concentration of 240 nM. Final reagent concentrations were: [Plasmin]=8 nM, [N-p-Tosyl-Gly-Pro-Lys-p-nitroanilide]=37 mM.

Chymotrypsin: Chymotrypsin activity was assessed as the ability to hydrolyze N-succinyl-Ala-Ala-Pro-Phe-p-nitroanilide. Substrate solutions were prepared at a concentration of 14 mM (14 mM<<$K_m$=62 mM) in assay buffer. Final DMSO'concentration was 4.3%. Purified bovine chymotrypsin was diluted into assay buffer to a concentration of 81 nM. Final reagent concentrations were: [Chymotrypsin]=2.7 nM, [N-succinyl-Ala-Ala-Pro-Phe-p-nitroanilide]=14 mM.

Trypsin: Trypsin activity was assessed as the ability to hydrolyze N-benzoyl-Phe-Val-Arg-p-nitroanilide. Substrate solutions were prepared at a concentration of 13 mM (13 mM<<$K_m$=291 mM) in assay buffer. Final DMSO concentration was 4.3%. Purified bovine trypsin was diluted into assay buffer to a concentration of 120 nM. Final reagent concentrations were: [Trypsin]=4 nM, [N-benzoyl-Phe-Val-Arg-p-nitroanilide]=13 mM.

Elastase: Elastase activity was assessed as the ability to hydrolyze N-succinyl-Ala-Ala-Pro-Val-p-nitroanilide. Substrate solutions were prepared at a concentration of 19 mM (19 mM<<$K_m$=89 mM) in assay buffer. Final DMSO concentration was 4.3%. Purified human leukocyte elastase was diluted into assay buffer to a concentration of 750 nM. Final reagent concentrations were: [Elastase]=25 nM, [N-succinyl-Ala-Ala-Pro-Val-p-nitroanilide]=19 mM.

Urokinase: Urokinase activity was assessed as the ability to hydrolyze N-CBZ-Val-Gly-Arg-p-nitroanilide. Substrate solutions were prepared at a concentration of 100 mM (100 mM<$K_m$=1.2 mM) in assay buffer. Final DMSO concentration was 4.3%. Purified human kidney urokinase was diluted into assay buffer to a concentration of 1.2 mM. Final reagent concentrations were: [Urokinase]=40 nM, and [N-CBZ-Val-Gly-Arg-p-nitroanilide]=100 mM.

The results of compounds of the invention are shown in the following table.

TABLE 1

| Eg. No. | Assay, $K_i$ (nM) or (% Inhibition at (nM)) | | | | | |
|---|---|---|---|---|---|---|
| | Thrombin | FXa | Chymo. | Elastase | Plasmin | Trypsin |
| 1 | 53 | 0@24,000 | 0@24,000 | 0@24,000 | 0@24,000 | 0@24,000 |
| 2 | 7.9 | 24,000 | 14,000 | 0@24,500 | 0@24,500 | 0@24,500 |
| 4 | 29 | 7,900 | | 0@79,000 | | |
| 5 | 6.0 | | 0@24,600 | 0@24,600 | 0@24,600 | 0@24,600 |
| 8 | 43 | | | 0@56,000 | | 0@56,000 |
| 16 | 2.0 | 2,200 | | 0@19,000 | | 4,000 |
| 24 | 2.0 | 2,200 | | 0@18,000 | | 7,600 |
| 30 | 61 | 7.600 | 0@23,500 | 0@23,500 | 0@23,500 | 0@23,500 |
| 38 | 51 | 420 | 0@20,000 | 0@20,000 | 0@20,000 | 0@20,000 |
| 55 | 220 | 2,100 | | | | 2,300 |
| 71 | 580 | 8,700 | 0@12,000 | 0@12,000 | 0@12,000 | 0@12,000 |
| 85 | 290 | 1,300 | 0@18,000 | 0@18,000 | 0@18,000 | 1,600 |

Chymo. = chymotrypsin

The results indicate that the compounds of the present invention are potent and highly selective inhibitors of thrombin.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having Formula VII:

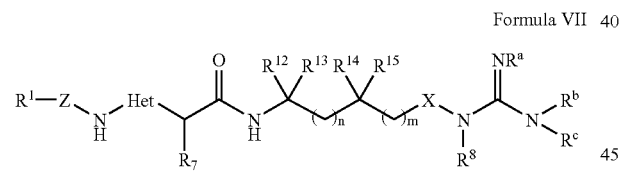

Formula VII or a pharmaceutically acceptable salt thereof; wherein:

$R^1$ is alkyl, cycloalkyl, cycloalkylalkyl, alkenyl, alkynyl, aryl, aralkyl, heterocycle or heterocycloalkyl, any of which may be optionally substituted;

Z is $NR^2CO—$ or a covalent bond, where $R^2$ is hydrogen, alkyl, aralkyl, aryl, hydroxy($C_{2-10}$) alkyl, amino($C_{2-10}$)alkyl, monoalkylamino($C_{2-10}$)alkyl, dialkylamino($C_{2-10}$)alkyl or carboxyalkyl;

Het is selected from the group consisting of

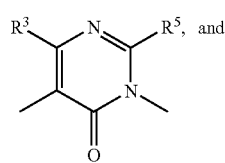

B

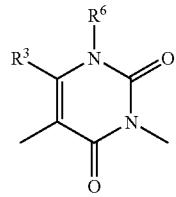

-continued

C where $R^3$ and $R^5$ are independently hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, alkoxycarbonylmethyl, carboxymethyl, $—CO_2R^x$, $—CH_2OR^x$ or $—OR^x$, where $R^x$, in each instance, is independently one of hydrogen, alkyl or cycloalkyl wherein said alkyl or cycloalkyl groups may optionally have one or more unsaturations;

$R^6$ is hydrogen, alkyl, aralkyl, aryl, cyano($C_{2-10}$)alkyl, hydroxy($C_{2-10}$)alkyl, alkoxy($C_{2-10}$)alkyl, mono- and di-alkylamino($C_{2-10}$)alkyl, or carboxyalkyl;

$R^7$ is hydrogen, $C_{1-4}$alkyl, or $C_{2-4}$ alkenyl;

$R^8$ is hydrogen, alkyl, alkenyl, aralkyl, aryl, hydroxyalkyl, aminoalkyl, monoalkylamino ($C_{2-10}$)alkyl, dialkylamino($C_{2-10}$)alkyl or carboxyalkyl;

$R^{12}$, $R^{13}$, $R^{14}$ and $R^{15}$ are independently hydrogen, alkyl, aralkyl, aryl, hydroxyalkyl, aminoalkyl, monoalkylaminoalkyl, dialkylaminoalkyl or carboxyalkyl;

or $R^{12}$ and $R^{13}$ are taken together to form $—(CH_2)_y—$, where y is 2 to 7, while $R^{14}$ and $R^{15}$ are defined as above;

or $R^{14}$ and $R^{15}$ are taken together to form $—(CH_2)_q—$, where q is 2 to 7, while $R^{12}$ and $R^{13}$ are defined as above;

or $R^{12}$ and $R^{14}$ are taken together to form $—(CH_2)_r—$, where r is 0 (a bond) or 1 to 7, while $R^{13}$ and $R^{15}$ are defined as above;

X is oxygen or $NR^9$, where $R^9$ is hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl;

$R^a$, $R^b$ and $R^c$ are independently hydrogen, alkyl, hydroxy, alkoxy, aryloxy, aralkoxy, alkoxycarbonyloxy, cyano or —$CO_2R^w$, where $R^w$ is alkyl, cycloalkyl, phenyl, benzyl,

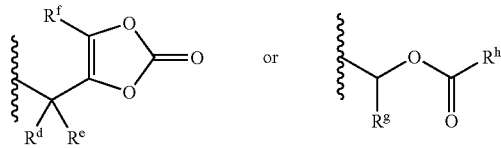

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n is from zero to 8; m is from zero to 6.

2. A compound of claim 1, wherein $R^1$ is $C_{6-10}$ ar($C_{1-4}$) alkyl, $C_{6-10}$ aryl, $C_{4-7}$ cycloalkyl($C_{1-4}$)alkyl, heterocycle or heterocyclo($C_{1-4}$)alkyl, any of which is optionally substituted; and wherein the heterocycle of said heterocycle or heterocyclo($C_{1-4}$)alkyl is a 5- to 7-member mono-cyclic, or 9- to 10-member bi-cyclic heterocyclic ring that is saturated or unsaturated, and contains 1 to 3 heteroatoms selected from N, O and S.

3. A compound of claim 2, wherein $R^1$ is $C_{6-10}$ ar($C_{1-4}$) alkyl, $C_{6-10}$ aryl, $C_{4-7}$ cycloalkyl($C_{1-4}$)alkyl, any of which is optionally substituted by 1-5 of hydroxy, nitro, trifluoromethyl, halogen, $C_{1-6}$ alkyl, $C_{2-6}$ alkenyl, $C_{6-10}$ aryl, $C_{1-6}$ alkoxy, $C_{6-10}$ ar($C_{1-6}$)alkoxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, ($C_{1-6}$)alkoxy($C_{2-6}$)alkoxy, mono- and di-$C_{1-4}$ alkylamino ($C_{2-6}$)alkoxy, $C_{2-10}$ mono(carboxyalkyl) amino, bis($C_{2-10}$ carboxyalkyl) amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{6-10}$ arylsulfonyl, $C_{6-10}$ ar($C_{1-6}$) alkylsulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, or perfluoroethoxy.

4. A compound of claim 1, wherein Het is

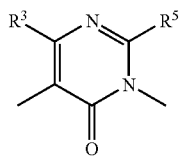

where $R^3$ and $R^5$ are independently hydrogen, $C_{1-4}$ alkyl, $C_{3-7}$ cycloalkyl, $C_{6-14}$ aryl, $C_{6-10}$ ar($C_{1-4}$)alkyl, trifluoromethyl, cyano, halogen, hydroxyalkyl, cyano, nitro, carboxamido, carboxy, alkoxycarbonyl, carboxymethyl, alkoxycarbonylmethyl, alkoxy, hydroxy, or cycloalkyloxycarbonyl.

5. A compound of claim 4, wherein $R^3$ and $R^5$ are independently hydrogen, methyl, ethyl, propyl, chloro, bromo, trifluoromethyl, cyano hydroxymethyl, methoxy, ethoxy, carboxamido, nitro, phenyl, cyclopropyl, hydroxy, isopropyl, methoxycarbonyl, ethoxycarbonyl and benzyl.

6. A compound of claim 1, wherein $R_3$ is independently hydrogen, $C_{1-12}$ alkyl, or $C_{2-6}$ alkenyl.

7. A compound of claim 6, wherein $R^3$ is hydrogen.

8. A compound of claim 1, wherein $R^5$ is hydrogen, halogen, cyano, $C_{1-5}$ alkyl, $C_{3-6}$ alkenyl, $C_{3-5}$ cycloalkyl, trifluoromethyl, or $C_{1-4}$ alkoxy.

9. A compound of claim 1, wherein Z a covalent bond.

10. A compound of claim 1, wherein $R^7$ is hydrogen.

11. A compound of claim 1, wherein X is oxygen.

12. A compound of claim 1, wherein X is $NR^9$.

13. A compound of claim 1, wherein $R^9$ is hydrogen or $C_{1-6}$ alkyl, optionally substituted by one, two or three, of amino, monoalkylamino, dialkylamino, alkoxy, hydroxy, alkoxycarbonyl, aryloxycarbonyl, aralkoxycarbonyl, carboalkoxy, phenyl, cyano, trifluoromethyl, acetylamino, pyridyl, thiophenyl, furyl, pyrrolyl or imidazolyl.

14. A compound of claim 1, wherein $R^9$ is hydrogen, methyl, ethyl, propyl, n-butyl, benzyl, phenethyl, 2-hydroxyethyl, 3-hydroxypropyl, 4-hydroxybutyl, carboxymethyl or carboxyethyl.

15. A compound of claim 1, wherein $R^8$ is hydrogen, $C_{1-6}$ alkyl or $C_{6-10}$ aryl ($C_{1-6}$)alkyl.

16. A compound of claim 1, wherein
$R^{12}$, $R^{13}$, $R^{14}$ and $R^{15}$ are independently one of hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl.

17. A compound of claim 1, wherein
$R^{12}$, $R^{13}$, $R^{14}$ and $R^{15}$ are independently hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl.

18. A compound of claim 1, wherein
$R^a$, $R^b$ and $R^c$ are independently hydrogen, hydroxy, $C_{1-6}$ alkyl, $C_{1-6}$ alkoxy, cyano or —$CO_2R^w$, where $R^w$, in each instance, is one of $C_{1-4}$alkyl, $C_{4-7}$cycloalkyl, benzyl,

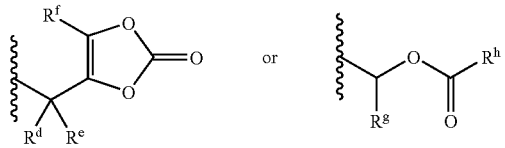

where $R^d$, $R^e$ and $R^g$ are hydrogen,
$R^f$ is methyl, and
$R^h$ is benzyl or tert-butyl.

19. A compound of claim 18, wherein
$R^a$, $R^b$ and $R^c$ are hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$.

20. A compound of claim 19, wherein $R^a$, $R^b$ and $R^c$ are each hydrogen.

21. A compound of claim 1, wherein n is zero to 6, and m is zero to 4.

22. A compound of claim 21, wherein n is zero to 4 and m is zero, 1 or 2.

23. A compound of claim 1, wherein
$R^1$ is phenyl, benzyl, 1-naphtylmethyl, 2-naphthylmethyl, pyridyl, pyridylmethyl, quinolinyl or quinolinylmethyl, any of which is optionally substituted by 1-5 of chloro, methoxy, methyl, trifluoromethyl, cyano, nitro, methylsulfonyl, amino or dimethylamino.

24. A compound of claim 1, wherein
$R^1$ is 8-quinolinyl, 5-methyl-8-quinolinyl, 8-quinolinylmethyl, 5-methyl-8-quinolinylmethyl, 4-benzo-2,1,3- thiadiazolyl, 5-chloro-2-thiophenyl, 5-chloro-1,3-dimethyl-4-pyrazolyl, pyridyl, isoquinolinyl, pyridylmethyl, isoquinolinylmethyl, tetrahydroquinolinyl and tetrahydroquinolinylmethyl.

25. A compound of claim 1, wherein m and n are each zero and $R^{12}$, $R^{13}$, $R^{14}$ and $R^{15}$ are each hydrogen.

26. A diagnostic composition comprising a compound having Formula VII:

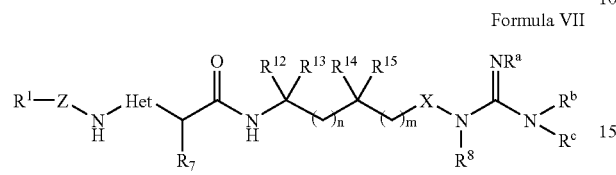

Formula VII or a pharmaceutically acceptable salt thereof; wherein:
$R^1$ is alkyl, cycloalkyl, cycloalkylalkyl, alkenyl, alkynyl, aryl, aralkyl, heterocycle or heterocycloalkyl, any of which may be optionally substituted;

Z is —$SO_2$—, —OCO—, —CO—, —$NR^2CO$— or a covalent bond,
where $R^2$ is hydrogen, alkyl, aralkyl, aryl, hydroxy($C_{2-10}$)alkyl, amino($C_{2-10}$)alkyl, monoalkylamino($C_{2-10}$)alkyl, dialkylamino($C_{2-10}$)alkyl or carboxyalkyl;

Het is selected from the group consisting of

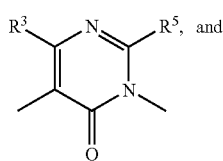  B

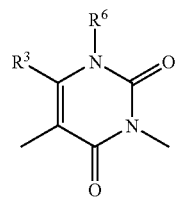  C where
$R^3$ and $R^5$ are independently hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, alkoxycarbonylmethyl, carboxymethyl, —$CO_2R^x$, —$CH_2OR^x$ or —$OR^x$,
where $R^x$, in each instance, is independently one of hydrogen, alkyl or cycloalkyl wherein said alkyl or cycloalkyl groups may optionally have one or more unsaturations;

$R^6$ is hydrogen, alkyl, aralkyl, aryl, cyano($C_{2-10}$)alkyl, hydroxy($C_{2-10}$)alkyl, alkoxy($C_{2-10}$)alkyl, mono- and di-alkylamino($C_{2-10}$)alkyl, or carboxyalkyl;

$R^7$ is hydrogen, $C_{1-4}$alkyl, or $C_{2-4}$ alkenyl;

$R^8$ is hydrogen, alkyl, alkenyl, aralkyl, aryl, hydroxyalkyl, aminoalkyl, monoalkylamino ($C_{2-10}$)alkyl, dialkylamino($C_{2-10}$)alkyl or carboxyalkyl;

$R^{12}$, $R^{13}$, $R^{14}$ and $R^{15}$ are independently hydrogen, alkyl, aralkyl, aryl, hydroxyalkyl, aminoalkyl, monoalkylaminoalkyl, dialkylaminoalkyl or carboxyalkyl;

or $R^{12}$ and $R^{13}$ are taken together to form —$(CH_2)_y$—, where y is 2 to 7, while $R^{14}$ and $R^{15}$ are defined as above;

or $R^{14}$ and $R^{15}$ are taken together to form —$(CH_2)_q$—, where q is 2 to 7, while $R^{12}$ and $R^{13}$ are defined as above;

or $R^{12}$ and $R^{14}$ are taken together to form —$(CH_2)_r$—, where r is 0 (a bond) or 1 to 7, while $R^{13}$ and $R^{15}$ are defined as above;

X is oxygen or $NR^9$,
where $R^9$ is hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl;

$R^a$, $R^b$ and $R^c$ are independently hydrogen, alkyl, hydroxy, alkoxy, aryloxy, aralkoxy, alkoxycarbonyloxy, cyano or —$CO_2R^w$, where
$R^w$ is alkyl, cycloalkyl, phenyl, benzyl,

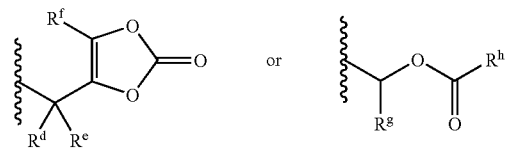

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n is from zero to 8; m is from zero to 6; and wherein said compound comprises a detectable label; and a pharmaceutically acceptable carrier or diluent.

27. The composition of claim 26, wherein said detectably label is a radioactive atom or a paramagnetic atom.

28. The composition of claim 26, wherein the $R^1$ group of said compound is substituted with a radioactive iodine atom selected from the group consisting of I-125, I-131 and I-123.

29. The composition of claim 26, wherein said detectable label comprises:
(a) an organic group L that is attached to the $R^1$ substituent of said compound, either directly or via a divalent linking group A", wherein L is an organic group capable of covalently bonding to or noncovalently binding to either a radioactive or paramagnetic atom; and A" is a group capable of covalently bonding with said organic group L; and
(b) a radioactive or paramagnetic atom.

30. The composition of claim 29, wherein A" is —C(=S)—, —C(=O)—, —C(=NH)—$(CH_2)_6$—C(=NH)—,

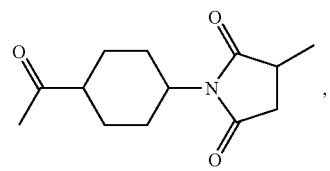

or —C(=O)—$(CH_2)_6$—C(=O)—.

31. The composition of claim 29, wherein L contains 3 to 12 methylene phosphonic acid groups, methylene carbohydroxamic acid groups, carboxyethylidene groups or carboxymethylene groups, which are bonded to a nitrogen atom.

32. The composition of claim 29, wherein L is diethylenetriamine-N, N, N', N", N"-pentaacetic acid (DTPA) or 1-(p-aminobenzyl)-diethylenetriaminepentaacetic acid.

33. The composition of claim 29, wherein said radioactive atom is selected from the group consisting of Co-57, Cu-67, Ga-67, Ga-68, Ru-97, Tc-99m, In-111, In-113m, Hg-197, Au-198, and Pb-203.

34. The composition of claim 29, wherein said paramagnetic atom is a divalent or trivalent ion of an element with an atomic number of 21 to 29, 58 to 70, 42, or 44.

35. The composition of claim 29, wherein said paramagnetic atom is selected from the group consisting of chromium (III), manganese(II), iron(III), iron(II), cobalt(II), nickel(II), copper(II), praseodymium(III), neodymium(III), samarium (III) and ytterbium(III).

36. The composition of claim 26, wherein said detectable label is a radioactive or paramagnetic chelate comprising:
(a) a group A"-L which substitutes for the groups -Z-$R^1$ in said compound, wherein
L is an organic group capable of covalently bonding to or noncovalently binding to either a radioactive or paramagnetic atom; and A" is a divalent linking group capable of covalently bonding with said organic group L; and
(b) a radioactive or paramagnetic atom.

37. The composition of claim 36, wherein A" is —C(=S), —C(=O)—, —C(=NH)—($CH_2$)$_6$—C(=NH)—,

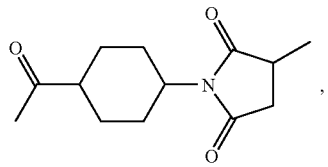

or —C(=O)—($CH_2$)$_6$—C(=O)—.

38. The composition of claim 36, wherein L contains 3 to 12 methylene phosphonic acid groups, methylene carbohydroxamic acid groups, carboxyethylidene groups or carboxymethylene groups, which are bonded to a nitrogen atom.

39. The composition of claim 36, wherein L is diethylenetriamine-N, N, N', N", N"-pentaacetic acid (DTPA) or 1-(p-aminobenzyl)-diethylenetriaminepentaacetic acid.

40. The composition of claim 36, wherein said radioactive atom is selected from the group consisting of Co-57, Cu-67, Ga-67, Ga-68, Ru-97, Tc-99m, In-111, In-113m, Hg-197, Au-198, and Pb-203.

41. The composition of claim 26, wherein $R^1$ is $C_{6-10}$ ar($C_{1-4}$) alkyl, $C_{6-10}$ aryl, $C_{4-7}$ cycloalkyl($C_{1-4}$)alkyl, heterocycle or heterocyclo($C_{1-4}$)alkyl, any of which is optionally substituted; and wherein the heterocycle of said heterocycle or heterocyclo($C_{1-4}$)alkyl is a 5- to 7-member mono-cyclic, or 9- to 10-member bi-cyclic heterocyclic ring that is saturated or unsaturated, and contains 1 to 3 heteroatoms selected from N, O and S.

42. The composition of claim 41, wherein $R^1$ is $C_{6-10}$ ar($C_{1-4}$) alkyl, $C_{6-10}$ aryl, $C_{4-7}$ cycloalkyl($C_{1-4}$)alkyl, any of which is optionally substituted by 1-5 of hydroxy, nitro, trifluoromethyl, halogen, $C_{1-6}$ alkyl, $C_{2-6}$ alkenyl, $C_{6-10}$ aryl, $C_{1-6}$ alkoxy, $C_{6-10}$ ar($C_{1-6}$)alkoxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, ($C_{1-6}$)alkoxy($C_{2-6}$)alkoxy, mono- and di-$C_{1-4}$ alkylamino ($C_{2-6}$)alkoxy, $C_{2-10}$ mono(carboxyalkyl) amino, bis($C_{2-10}$ carboxyalkyl) amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{6-10}$ arylsulfonyl, $C_{6-10}$ ar($C_{1-6}$) alkylsulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, or perfluoroethoxy.

43. The composition of claim 26, wherein Het is

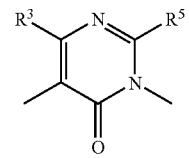

where $R^3$ and $R^5$ are independently hydrogen, $C_{1-4}$ alkyl, $C_{3-7}$ cycloalkyl, $C_{6-14}$ aryl, $C_{6-10}$ ar($C_{1-4}$)alkyl, trifluoromethyl, cyano, halogen, hydroxyalkyl, cyano, nitro, carboxamido, carboxy, alkoxycarbonyl, carboxymethyl, alkoxycarbonylmethyl, alkoxy, hydroxy, or cycloalkyloxycarbonyl.

44. The composition of claim 43, wherein $R^3$ and $R^5$ are independently hydrogen, methyl, ethyl, propyl, chloro, bromo, trifluoromethyl, cyano hydroxymethyl, methoxy, ethoxy, carboxamido, nitro, phenyl, cyclopropyl, hydroxy, isopropyl, methoxycarbonyl, ethoxycarbonyl and benzyl.

45. The composition of claim 26, wherein $R^3$ is independently hydrogen, $C_{1-12}$ alkyl, or $C_{2-6}$ alkenyl.

46. The composition of claim 45, wherein $R^3$ is hydrogen.

47. The composition of claim 26, wherein $R^5$ is hydrogen, halogen, cyano, $C_{1-5}$ alkyl, $C_{3-6}$ alkenyl, $C_{3-5}$ cycloalkyl, trifluoromethyl, or $C_{1-4}$ alkoxy.

48. The composition of claim 26, wherein Z is —$SO_2$— or a covalent bond.

49. The composition of claim 26, wherein $R^7$ is hydrogen.

50. The composition of claim 26, wherein X is oxygen.

51. The composition of claim 26, wherein X is $NR^9$.

52. The composition of claim 26, wherein $R^9$ is hydrogen or $C_{1-6}$ alkyl, optionally substituted by one, two or three, of amino, monoalkylamino, dialkylamino, alkoxy, hydroxy, alkoxycarbonyl, aryloxycarbonyl, aralkoxycarbonyl, carboalkoxy, phenyl, cyano, trifluoromethyl, acetylamino, pyridyl, thiophenyl, furyl, pyrrolyl or imidazolyl.

53. The composition of claim 26, wherein $R^9$ is hydrogen, methyl, ethyl, propyl, n-butyl, benzyl, phenethyl, 2-hydroxyethyl, 3-hydroxypropyl, 4-hydroxybutyl, carboxymethyl or carboxyethyl.

54. The composition of claim 26, wherein $R^8$ is hydrogen, $C_{1-6}$ alkyl or $C_{6-10}$ aryl ($C_{1-6}$)alkyl.

55. The composition of claim 26, wherein
$R^{12}$, $R^{13}$, $R^{14}$ and $R^{15}$ are independently one of hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl.

56. The composition of claim 55, wherein
$R^{12}$, $R^{13}$, $R^{14}$ and $R^{15}$ are independently hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl.

57. The composition of claim 26, wherein
R$^a$, R$^b$ and R$^c$ are independently hydrogen, hydroxy, C$_{1-6}$ alkyl, C$_{1-6}$ alkoxy, cyano or —CO$_2$R$^w$, where R$^w$, in each instance, is one of C$_{1-4}$alkyl, C$_{4-7}$cycloalkyl, benzyl,

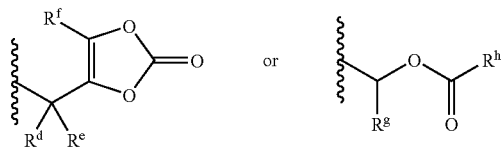

where R$^d$, R$^e$ and R$^g$ are hydrogen,
R$^f$ is methyl, and
R$^h$ is benzyl or tert-butyl.

58. The composition of claim 57, wherein
R$^a$, R$^b$ and R$^c$ are hydrogen, methyl, ethyl, propyl, n-butyl, hydroxy, methoxy, ethoxy, cyano, —CO$_2$CH$_3$, —CO$_2$CH$_2$CH$_3$ and —CO$_2$CH$_2$CH$_2$CH$_3$.

59. The composition of claim 58, wherein R$^a$, R$^b$ and R$^c$ are each hydrogen.

60. The composition of claim 26, wherein n is zero to 6, and m is zero to 4.

61. The composition of claim 60, wherein n is zero to 4 and m is zero, 1 or 2.

62. The composition of claim 26, wherein
R$^1$ is phenyl, benzyl, 1-naphtylmethyl, 2-naphthylmethyl, pyridyl, pyridylmethyl, quinolinyl or quinolinylmethyl, any of which is optionally substituted by 1-5 of chloro, methoxy, methyl, trifluoromethyl, cyano, nitro, methylsulfonyl, amino or dimethylamino.

63. The composition of claim 26, wherein said compound is:
R$^1$ is 8-quinolinyl, 5-methyl-8-quinolinyl, 8-quinolinylmethyl, 5-methyl-8-quinolinylmethyl, 4-benzo-2,1,3-thiadiazolyl, 5-chloro-2-thiophenyl, 5-chloro-1,3-dimethyl-4-pyrazolyl, pyridyl, isoquinolinyl, pyridylmethyl, isoquinolinylmethyl, tetrahydroquinolinyl and tetrahydroquinolinylmethyl.

64. The composition of claim 26, wherein m and n are each zero and R$^{12}$, R$^{13}$, R$^{14}$ and R$^{15}$ are each hydrogen.

* * * * *

UNITED STATES PATENT AND TRADEMARK OFFICE
CERTIFICATE OF CORRECTION

PATENT NO. : 7,402,586 B2
APPLICATION NO. : 11/254086
DATED : July 22, 2008
INVENTOR(S) : Tianbao Lu et al.

It is certified that error appears in the above-identified patent and that said Letters Patent is hereby corrected as shown below:

Title Page,
Item (56) References Cited:
OTHER PUBLICATIONS
Page 2,
"Jeong, J.H. et al.," reference, delete "4427" and insert -- 4227 --.

Column 7,
Line 58, delete "ar($C_1$)" and insert -- ar($C_{1-6}$) --.

Column 10,
Line 57, delete "–CO, $R^w$," and insert -- –$CO_2R^w$, --.

Column 14,
Line 1, delete "aminomethyl-1" and insert -- amino-6-methyl-1 --.

Column 15,
Line 1, delete "amino-methyl-1" and insert -- amino-6-methyl-1 --.
Lines 32-33, delete "amino-methyl-1" and insert -- amino-6-methyl-1 --.

Column 53,
Lines 27-28, delete "α-cyanohydroxycinnamic acid matrix)" and insert
-- α-cyano-4-hydroxycinnamic acid matrix) --.

UNITED STATES PATENT AND TRADEMARK OFFICE
CERTIFICATE OF CORRECTION

PATENT NO.         : 7,402,586 B2
APPLICATION NO.    : 11/254086
DATED              : July 22, 2008
INVENTOR(S)        : Tianbao Lu et al.

It is certified that error appears in the above-identified patent and that said Letters Patent is hereby corrected as shown below:

Column 65,
Line 54, delete "[(22 guanidinooxyethyl)" and insert
-- [(2-guanidinooxyethyl) --.

Signed and Sealed this

Twenty-second Day of December, 2009

David J. Kappos
*Director of the United States Patent and Trademark Office*